US012760300B2

(12) United States Patent
Nozaki et al.

(10) Patent No.: US 12,760,300 B2
(45) Date of Patent: Oct. 13, 2026

(54) VECTOR SET FOR MEASURING TRANSPOSASE ACTIVITY, KIT, TRANSPOSASE ACTIVITY MEASURING METHOD, AND CELL SEPARATION METHOD

(71) Applicant: KABUSHIKI KAISHA TOSHIBA, Tokyo (JP)

(72) Inventors: Emi Nozaki, Shinagawa (JP); Eiichi Akahoshi, Shinagawa (JP); Mitsuko Ishihara, Setagaya (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 953 days.

(21) Appl. No.: 17/930,961

(22) Filed: Sep. 9, 2022

(65) Prior Publication Data

US 2023/0102794 A1 Mar. 30, 2023

Related U.S. Application Data

(63) Continuation of application No. PCT/JP2021/033368, filed on Sep. 10, 2021.

(30) Foreign Application Priority Data

Jan. 13, 2021 (JP) ................................ 2021-003669

(51) Int. Cl.
*C12N 15/00* (2006.01)
*C12N 15/10* (2006.01)
(Continued)

(52) U.S. Cl.
CPC ......... *C12N 15/1055* (2013.01); *C12N 15/85* (2013.01); *C12Q 1/485* (2013.01); *C12N 2800/107* (2013.01)

(58) Field of Classification Search
USPC .............. 435/6.1, 6.11, 91.1, 320.1; 436/94; 536/23.1
See application file for complete search history.

(56) References Cited

U.S. PATENT DOCUMENTS

2006/0121509 A1 6/2006 Hermiston et al.
2020/0283794 A1 * 9/2020 Kotin .................... C12N 15/63

FOREIGN PATENT DOCUMENTS

EP 2 441 831 A1 4/2012
JP 2020-146014 A 9/2020
(Continued)

OTHER PUBLICATIONS

Scheuermann et al., Evolution-guided evaluation of the inverted terminal repeats of the synthetic transposon Sleeping Beauty. Nature Scientific Reports, 9,1171, 2019.*
(Continued)

*Primary Examiner* — Frank W Lu
(74) *Attorney, Agent, or Firm* — Oblon, McClelland, Maier & Neustadt, L.L.P.

(57) ABSTRACT

According to one embodiment, a vector set includes a first vector and a second vector. The first vector includes a transposase target sequence, a first promoter sequence ligated to downstream of the transposase target sequence, and a first reporter gene ligated to downstream of the first promoter sequence. The second vector includes a 5'-side transposase recognition sequence, a 3'-side transposase recognition sequence, and a first enhancer sequence arranged therebetween.

17 Claims, 13 Drawing Sheets

Specification includes a Sequence Listing.

(51) Int. Cl.
*C12N 15/85* (2006.01)
*C12Q 1/48* (2006.01)

(56) References Cited

FOREIGN PATENT DOCUMENTS

| | | | |
|---|---|---|---|
| JP | 2020-146016 | A | 9/2020 |
| WO | WO 2010/143698 | A1 | 12/2010 |
| WO | WO 2019/219947 | A1 | 11/2019 |

OTHER PUBLICATIONS

"Xcml cutting site". Printed on Aug. 22, 2025.*
Stratagene Catalog (1988), p. 39. Published by Stratgene, 11011 North Torrey Pines Road, La Jolla, CA 92037, USA.*
Japanese Decision to Grant a Patent issued Aug. 6, 2024 in Japanese Application 2021-003669, (with unedited computer-generated English translation), citing documents 1,15 and 17 therein, 5 pages.
Written Opinion issued Feb. 23, 2022 in PCT/JP2021/033368 filed on Sep. 10, 2021, Citing reference 16, 6 pages.
Pulkkinen, E. et al. "An assay to monitor the activity of DNA transposition complexes yields a general quality control measure for transpositional recombination reactions", Mobile Genetic Elements (vol. 4 No. 5), 2014, pp. 1-8, DOI: 10.4161/21592543.2014.969576. (8 pages).

* cited by examiner

SEQUENCE LISTING

```
Sequence total quantity: 19
SEQ ID NO: 1            moltype = DNA  length = 56
FEATURE                 Location/Qualifiers
source                  1..56
                        mol_type = other DNA
                        organism = Trichoplusia ni
SEQUENCE: 1
agacgcttaa agacgcttaa agacgcttaa agacgcttaa agacgcttaa agacgc      56
```

```
SEQ ID NO: 2            moltype = DNA  length = 654
FEATURE                 Location/Qualifiers
source                  1..654
                        mol_type = other DNA
                        organism = Cytomegalovirus sp.
SEQUENCE: 2
cgatgtacgg gccagatata cgcgttgaca ttgattattg actagttatt aatagtaatc  60
aattacgggg tcattagttc atagcccata tatggagttc cgcgttacat aacttacggt  120
aaatggcccg cctggctgac cgcccaacga cccccgccca ttgacgtcaa taatgacgta  180
tgttcccata gtaacgccaa tagggacttt ccattgacgt caatgggtgg agtatttacg  240
gtaaactgcc cacttggcag tacatcaagt gtatcatatg ccaagtacgc cccctattga  300
cgtcaatgac ggtaaatggc ccgcctggca ttatgcccag tacatgacct tatgggactt  360
tcctacttgg cagtacatct acgtattagt catcgctatt accatggtga tgcggttttg  420
gcagtacatc aatgggcgtg gatagcggtt tgactcacgg ggatttccaa gtctccaccc  480
cattgacgtc aatgggagtt tgttttggca ccaaaatcaa cgggactttc caaaatgtcg  540
taacaactcc gccccattga cgcaaatggg cggtaggcgt gtacggtggg aggtctatat  600
aagcagagct ctctggctaa ctagagaacc cactgcttac tggcttatcg aaat        654

SEQ ID NO: 3            moltype = DNA  length = 1188
FEATURE                 Location/Qualifiers
source                  1..1188
                        mol_type = other DNA
                        organism = Homo sapiens
SEQUENCE: 3
cgtgaggctc cggtgcccgt cagtgggcag agcgcacatc gcccacagtc cccgagaagt  60
tggggggagg ggtcggcaat tgaaccggtg cctagagaag gtggcgcggg gtaaactggg  120
aaagtgatgt cgtgtactgg ctccgccttt ttcccgaggg tgggggagaa ccgtatataa  180
gtgcagtagt cgccgtgaac gttctttttc gcaacgggtt tgccgccaga acacaggtaa  240
gtgccgtgtg tggttcccgc gggcctggcc tctttacggg ttatggccct tgcgtgcctt  300
gaattacttc cacgcccctg gctgcagtac gtgattcttg atcccgagct tcgggttgga  360
agtgggtggg agagttcgag gccttgcgct taaggagccc cttcgcctcg tgcttgagtt  420
gaggcctggc ttgggcgctg gggccgccgc gtgcgaatct ggtggcacct tcgcgcctgt  480
ctcgctgctt tcgataagtc tctagccatt taaaattttt gatgacctgc tgcgacgctt  540
tttttctggc aagatagtct tgtaaatgcg ggccaagatc tgcacactgg tatttcggtt  600
tttggggccg cgggcggcga cggggcccgt gcgtcccagc gcacatgttc ggcgaggcgg  660
ggcctgcgag cgcggccacc gagaatcgga cgggggtagt ctcaagctgg ccggcctgct  720
ctggtgcctg gcctcgcgcc gccgtgtatc gccccgccct gggcggcaag gctggcccgg  780
tcggcaccag ttgcgtgagc ggaaagatgg ccgcttcccg gccctgctgc agggagctca  840
aaatggagga cgcggcgctc gggagagcgg gcgggtgagt cacccacaca aaggaaaagg  900
gcctttccgt cctcagccgt cgcttcatgt gactccacgg agtaccgggc gccgtccagg  960
cacctcgatt agttctcgag cttttggagt acgtcgtctt taggttgggg ggaggggttt  1020
tatgcgatgg agtttcccca cactgagtgg gtggagactg aagttaggcc agcttggcac  1080
ttgatgtaat tctccttgga atttgccctt tttgagtttg gatcttggtt cattctcaag  1140
cctcagacag tggttcaaag tttttttctt ccatttcagg tgtcgtga               1188

SEQ ID NO: 4            moltype = DNA  length = 1653
FEATURE                 Location/Qualifiers
source                  1..1653
                        mol_type = other DNA
                        note = Firefly
                        organism = synthetic construct
SEQUENCE: 4
atggaagacg ccaaaaacat aaagaaaggc ccggcgccat tctatccgct ggaagatgga  60
accgctggag agcaactgca taaggctatg aagagatacg ccctggttcc tggaacaatt  120
gcttttacag atgcacatat cgaggtggac atcacttacg ctgagtactt cgaaatgtcc  180
gttcggttgg cagaagctat gaaacgatat gggctgaata caaatcacag aatcgtcgta  240
tgcagtgaaa actctcttca attctttatg ccggtgttgg gcgcgttatt tatcggagtt  300
gcagttgcgc ccgcgaacga catttataat gaacgtgaat tgctcaacag tatgggcatt  360
tcgcagccta ccgtggtgtt cgtttccaaa aaggggttgc aaaaaatttt gaacgtgcaa  420
aaaaagctcc caatcatcca aaaaattatt atcatggatt ctaaaacgga ttaccaggga  480
tttcagtcga tgtacacgtt cgtcacatct catctacctc ccggttttaa tgaatacgat  540
tttgtgccag agtccttcga tagggacaag acaattgcac tgatcatgaa ctcctctgga  600
tctactggtc tgcctaaagg tgtcgctctg cctcatagaa ctgcctgcgt gagattctcg  660
catgccagag atcctatttt tggcaatcaa atcattccgg atactgcgat tttaagtgtt  720
gttccattcc atcacggttt tggaatgttt actacactcg gatatttgat atgtggattt  780
cgagtcgtct taatgtatag atttgaagaa gagctgtttc tgaggagcct tcaggattac  840
aagattcaaa gtgcgctgct ggtgccaacc ctattctcct tcttcgccaa aagcactctg  900
attgacaaat acgatttatc taatttacac gaaattgctt ctggtggcgc tcccctctct  960
aaggaagtcg gggaagcggt tgccaagagg ttccatctgc caggtatcag gcaaggatat  1020
gggctcactg agactacatc agctattctg attacacccg agggggatga taaaccgggc  1080
gcggtcggta aagttgttcc atttttttgaa gcgaaggttg tggatctgga taccgggaaa  1140
acgctgggcg ttaatcaaag aggcgaactg tgtgtgagag gtcctatgat tatgtccggt  1200
tatgtaaaca atccggaagc gaccaacgcc ttgattgaca aggatggatg gctacattct  1260
ggagacatag cttactggga cgaagacgaa cacttcttca tcgttgaccg cctgaagtct  1320
ctgattaagt acaaaggcta tcaggtggct cccgctgaat tggaatccat cttgctccaa  1380
caccccaaca tcttcgacgc aggtgtcgca ggtcttcccg acgatgacgc cggtgaactt  1440
cccgccgccg ttgttgtttt ggagcacgga aagacgatga cggaaaaaga gatcgtggat  1500
tacgtcgcca gtcaagtaac aaccgcgaaa aagttgcgcg gaggagttgt gtttgtggac  1560
```

-continued

```
gaagtaccga aaggtcttac cggaaaactc gacgcaagaa aaatcagaga gatcctcata  1620
aaggccaaga agggcggaaa gatcgccgtg taa                               1653

SEQ ID NO: 5           moltype = DNA  length = 550
FEATURE                Location/Qualifiers
source                 1..550
                       mol_type = other DNA
                       organism = Oplophorus gracilirostris
SEQUENCE: 5
agcttggcaa tccggtactg ttggtaaagc caccatggtc ttcacactcg aagatttcgt  60
tggggactgg cgacagacag ccggctacaa cctggaccaa gtccttgaac agggaggtgt  120
gtccagtttg tttcagaatc tcggggtgtc cgtaactccg atccaaagga ttgtcctgag  180
cggtgaaaat gggctgaaga tcgacatcca tgtcatcatc ccgtatgaag gtctgagcgg  240
cgaccaaatg ggccagatcg aaaaaatttt taaggtggtg taccctgtgg atgatcatca  300
ctttaaggtg atcctgcact atggcacact ggtaatcgac ggggttacgc cgaacatgat  360
cgactatttc ggacggccgt atgaaggcat cgccgtgttc gacggcaaaa agatcactgt  420
aacagggacc ctgtggaacg gcaacaaaat tatcgacgag cgcctgatca accccgacgg  480
ctccctgctg ttccgagtaa ccatcaacgg agtgaccggc tggcggctgt gcgaacgcat  540
tctggcgtaa                                                         550

SEQ ID NO: 6           moltype = DNA  length = 228
FEATURE                Location/Qualifiers
source                 1..228
                       mol_type = other DNA
                       note = Bovine
                       organism = synthetic construct
SEQUENCE: 6
gtttaaaccc gctgatcagc ctcgactgtg ccttctagtt gccagccatc tgttgtttgc  60
ccctcccccg tgccttcctt gaccctggaa ggtgccactc ccactgtcct ttcctaataa  120
aatgaggaaa ttgcatcgca ttgtctgagt aggtgtcatt ctattctggg gggtggggtg  180
gggcaggaca gcaaggggga ggattgggaa gacaatagca ggcatgct                228

SEQ ID NO: 7           moltype = DNA  length = 131
FEATURE                Location/Qualifiers
source                 1..131
                       mol_type = other DNA
                       organism = Simian virus 40
SEQUENCE: 7
cagacatgat aagatacatt gatgagtttg gacaaaccac aactagaatg cagtgaaaaa  60
aatgctttat ttgtgaaatt tgtgatgcta ttgctttatt tgtaaccatt ataagctgca  120
ataaacaagt t                                                       131

SEQ ID NO: 8           moltype = DNA  length = 311
FEATURE                Location/Qualifiers
source                 1..311
                       mol_type = other DNA
                       organism = Trichoplusia ni
SEQUENCE: 8
ttaaccctag aaagatagtc tgcgtaaaat tgacgcatgc attcttgaaa tattgctctc  60
tctttctaaa tagcgcgaat ccgtcgctgt gcatttagga catctcagtc gccgcttgga  120
gctcccgtga ggcgtgcttg tcaatgcggt aagtgtcact gattttgaac tataacgacc  180
gcgtgagtca aaatgacgca tgattatctt ttacgtgact tttaagattt aactcatacg  240
ataattatat tgttatttca tgttctactt acgtgataac ttattatata tatattttct  300
tgttatagat a                                                       311

SEQ ID NO: 9           moltype = DNA  length = 236
FEATURE                Location/Qualifiers
source                 1..236
                       mol_type = other DNA
                       organism = Trichoplusia ni
SEQUENCE: 9
ttttgttact ttatagaaga aattttgagt ttttgttttt ttttaataaa taaataaaca  60
taaataaatt gtttgttgaa tttattatta gtatgtaagt gtaaatataa taaaacttaa  120
tatctattca aattaataaa taaacctcga tatacagacc gataaaacac atgcgtcaat  180
tttacgcatg attatcttta acgtacgtca caatatgatt atctttctag ggttaa       236

SEQ ID NO: 10          moltype = DNA  length = 246
FEATURE                Location/Qualifiers
misc_feature           1..246
                       note = SleepingBeauty recognition sequence
source                 1..246
                       mol_type = other DNA
                       organism = synthetic construct
SEQUENCE: 10
tatacagttg aagtcggaag tttacataca cytwagccaa atacatttaa actcactttt  60
tcacaattcc tgacatttaa tcctagtaaa aattccctgt cttaggtcag ttaggatcac  120
cactttattt taagaatgtg aaatatcaga ataatagtag agagaatgat gtktacakac  180
asdtcatttc agcttttatt tctttcatca cattyccagt gggtcagaag tgtacataca  240
cgvkct                                                             246
```

```
SEQ ID NO: 11          moltype = DNA  length = 307
FEATURE                Location/Qualifiers
source                 1..307
                       mol_type = other DNA
                       organism = Oplophorus gracilirostris
SEQUENCE: 11
gcgttacata acttacggta aatggcccgc ctggctgacc gcccaacgac ccccgcccat  60
tgacgtcaat aatgacgtat gttcccatag taacgccaat agggactttc cattgacgtc  120
aatgggtgga gtatttacgg taaactgccc acttggcagt acatcaagtg tatcatatgc  180
caagtacgcc ccctattgac gtcaatgacg gtaaatggcc cgcctggcat tatgcccagt  240
acatgacctt atgggacttt cctacttggc agtacatcta cgtattagtc atcgctatta  300
ccatggt                                                            307

SEQ ID NO: 12          moltype = DNA  length = 526
FEATURE                Location/Qualifiers
source                 1..526
                       mol_type = other DNA
                       note = Firefly
                       organism = synthetic construct
SEQUENCE: 12
atggaagacg ccaaaaacat aaagaaaggc ccggcgccat tctatccgct ggaagatgga  60
accgctggag agcaactgca taaggctatg aagagatacg ccctggttcc tggaacaatt  120
gcttttacag atgcacatat cgaggtggac atcacttacg ctgagtactt cgaaatgtcc  180
gttcggttgg cagaagctat gaaacgatat gggctgaata caaatcacag aatcgtcgta  240
tgcagtgaaa actctcttca attctttatg ccggtgttgg gcgcgttatt tatcggagtt  300
gcagttgcgc ccgcgaacga catttataat gaacgtgaat tgctcaacag tatgggcatt  360
tcgcagccta ccgtggtgtt cgtttccaaa aaggggttgc aaaaaatttt gaacgtgcaa  420
aaaaagctcc caatcatcca aaaaattatt atcatggatt ctaaaacgga ttaccaggga  480
tttcagtcga tgtacacgtt cgtcacatct catctacctc ccggtt                 526

SEQ ID NO: 13          moltype = DNA  length = 1123
FEATURE                Location/Qualifiers
source                 1..1123
                       mol_type = other DNA
                       note = Firefly
                       organism = synthetic construct
SEQUENCE: 13
tgaatacgat tttgtgccag agtccttcga tagggacaag acaattgcac tgatcatgaa  60
ctcctctgga tctactggtc tgcctaaagg tgtcgctctg cctcatagaa ctgcctgcgt  120
gagattctcg catgccagag atcctatttt tggcaatcaa atcattccgg atactgcgat  180
tttaagtgtt gttccattcc atcacggttt tggaatgttt actacactcg gatatttgat  240
atgtggattt cgagtcgtct taatgtatag atttgaagaa gagctgtttc tgaggagcct  300
tcaggattac aagattcaaa gtgcgctgct ggtgccaacc ctattctcct tcttcgccaa  360
aagcactctg attgacaaat acgatttatc taatttacac gaaattgctt ctggtggcgc  420
tcccctctct aaggaagtcg gggaagcggt tgccaagagg ttccatctgc caggtatcag  480
gcaaggatat gggctcactg agactacatc agctattctg attacacccg agggggatga  540
taaaccgggc gcggtcggta aagttgttcc atttttttgaa gcgaaggttg tggatctgga  600
taccgggaaa acgctgggcg ttaatcaaag aggcgaactg tgtgtgagag gtcctatgat  660
tatgtccggt tatgtaaaca atccggaagc gaccaacgcc ttgattgaca aggatggatg  720
gctacattct ggagacatag cttactggga cgaagacgaa cacttcttca tcgttgaccg  780
cctgaagtct ctgattaagt acaaaggcta tcaggtggct cccgctgaat tggaatccat  840
cttgctccaa caccccaaca tcttcgacgc aggtgtcgca ggtcttcccg acgatgacgc  900
cggtgaactt cccgccgccg ttgttgtttt ggagcacgga aagacgatga cggaaaaaga  960
gatcgtggat tacgtcgcca gtcaagtaac aaccgcgaaa aagttgcgcg gaggagttgt  1020
gtttgtggac gaagtaccga aaggtcttac cggaaaactc gacgcaagaa aaatcagaga  1080
gatcctcata aaggccaaga agggcggaaa gatcgccgtg taa                    1123

SEQ ID NO: 14          moltype = DNA  length = 615
FEATURE                Location/Qualifiers
misc_feature           1..615
                       note = multiple cloning sequence
source                 1..615
                       mol_type = other DNA
                       organism = synthetic construct
SEQUENCE: 14
ccctagaaag atagtctgcg taaaattgac gcatgcattc ttgaaatatt gctctctctt  60
tctaaatagc gcgaatccgt cgctgtgcat ttaggacatc tcagtcgccg cttggagctc  120
ccgtgaggcg tgcttgtcaa tgcggtaagt gtcactgatt ttgaactata acgaccgcgt  180
gagtcaaaat gacgcatgat tatcttttac gtgactttta agatttaact catacgataa  240
ttatattgtt atttcatgtt ctacttacgt gataacttat tatatatata ttttcttgtt  300
atagatatct ggcctaactg gccggtacct gagctcgcta gcctcgagga tatcaagatc  360
tggcctcggc ggccaagctt ggcttttgtt actttataga agaaattttg agtttttgtt  420
ttttttttaat aaataaataa acataaataa attgtttgtt gaatttatta ttagtatgta  480
agtgtaaata taataaaact taatatctat tcaaattaat aaataaacct cgatatacag  540
accgataaaa cacatgcgtc aattttacgc atgattatct ttaacgtacg tcacaatatg  600
attatctttc taggg                                                   615

SEQ ID NO: 15          moltype = DNA  length = 6878
```

-continued

```
FEATURE                 Location/Qualifiers
misc_feature            1..6878
                        note = pCMV-LuIRuC
source                  1..6878
                        mol_type = other DNA
                        organism = synthetic construct
SEQUENCE: 15
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
gtttaaactt aagcttggca ttccggtact gttggtaaag ccaccatgga agacgccaaa  960
aacataaaga aaggcccggc gccattctat ccgctggaag atggaaccgc tggagagcaa  1020
ctgcataagg ctatgaagag atacgccctg gttcctggaa caattgcttt tacagatgca  1080
catatcgagg tggacatcac ttacgctgag tacttcgaaa tgtccgttcg gttggcagaa  1140
gctatgaaac gatatgggct gaatacaaat cacagaatcg tcgtatgcag tgaaaactct  1200
cttcaattct ttatgccggt gttgggcgcg ttatttatcg gagttgcagt tgcgcccgcg  1260
aacgacattt ataatgaacg tgaattgctc aacagtatgg gcatttcgca gcctaccgtg  1320
gtgttcgttt ccaaaaaggg gttgcaaaaa attttgaacg tgcaaaaaaa gctcccaatc  1380
atccaaaaaa ttattatcat ggattctaaa acggattacc agggatttca gtcgatgtac  1440
acgttcgtca catctcatct acctcccggt tttaatccta gaaagatagt ctgcgtaaaa  1500
ttgacgcatg cattcttgaa atattgctct ctctttctaa atagcgcgaa tccgtcgctg  1560
tgcatttagg acatctcagt cgccgcttgg agctcccgtg aggcgtgctt gtcaatgcgg  1620
taagtgtcac tgattttgaa ctataacgac cgcgtgagtc aaaatgacgc atgattatct  1680
tttacgtgac ttttaagatt taactcatac gataattata ttgttatttc atgttctact  1740
tacgtgataa cttattatat atatattttc ttgttataga tatctggcct aactggccgg  1800
tacctgagct cgctagcctc gaggatatca agatctggcc tcggcggcca agcttggctt  1860
ttgttacttt atagaagaaa ttttgagttt ttgttttttt ttaataaata aataaacata  1920
aataaattgt ttgttgaatt tattattagt atgtaagtgt aaatataata aaacttaata  1980
tctattcaaa ttaataaata aacctcgata tacagaccga taaaacacat gcgtcaattt  2040
tacgcatgat tatctttaac gtacgtcaca atatgattat ctttctaggg aatttgaata  2100
cgattttgtg ccagagtcct tcgataggga caagacaatt gcactgatca tgaactcctc  2160
tggatctact ggtctgccta aaggtgtcgc tctgcctcat agaactgcct gcgtgagatt  2220
ctcgcatgcc agagatccta tttttggcaa tcaaatcatt ccggatactg cgattttaag  2280
tgttgttcca ttccatcacg gttttggaat gtttactaca ctcggatatt tgatatgtgg  2340
atttcgagtc gtcttaatgt atagatttga agaagagctg tttctgagga gccttcagga  2400
ttacaagatt caaagtgcgc tgctggtgcc aaccctattc tccttcttcg ccaaaagcac  2460
tctgattgac aaatacgatt tatctaattt acacgaaatt gcttctggtg gcgctcccct  2520
ctctaaggaa gtcggggaag cggttgccaa gaggttccat ctgccaggta tcaggcaagg  2580
atatgggctc actgagacta catcagctat tctgattaca cccgaggggg atgataaacc  2640
gggcgcggtc ggtaaagttg ttccattttt tgaagcgaag gttgtggatc tggataccgg  2700
gaaaacgctg ggcgttaatc aaagaggcga actgtgtgtg agaggtccta tgattatgtc  2760
cggttatgta aacaatccgg aagcgaccaa cgccttgatt gacaaggatg gatggctaca  2820
ttctggagac atagcttact gggacgaaga cgaacacttc ttcatcgttg accgcctgaa  2880
gtctctgatt aagtacaaag gctatcaggt ggctcccgct gaattggaat ccatcttgct  2940
ccaacacccc aacatcttcg acgcaggtgt cgcaggtctt cccgacgatg acgccggtga  3000
acttcccgcc gccgttgttg ttttggagca cggaaagacg atgacggaaa aagagatcgt  3060
ggattacgtc gccagtcaag taacaaccgc gaaaaagttg cgcggaggag ttgtgtttgt  3120
ggacgaagta ccgaaaggtc ttaccggaaa actcgacgca agaaaaatca gagagatcct  3180
cataaaggcc aagaagggcg gaaagatcgc cgtgtaattc tagagggccc gcggttcgaa  3240
ggtaagccta tccctaaccc tctcctcggt ctcgattcta cgcgtaccgg tcatcatcac  3300
catcaccatt gagtttaaac ccgctgatca gcctcgactg tgccttctag ttgccagcca  3360
tctgttgttt gcccctcccc cgtgccttcc ttgaccctgg aaggtgccac tcccactgtc  3420
ctttcctaat aaaatgagga aattgcatcg cattgtctga gtaggtgtca ttctattctg  3480
gggggtgggg tggggcagga cagcaagggg gaggattggg aagacaatag caggcatgct  3540
ggggatgcgg tgggctctat ggcttctgag gcggaaagaa ccagctgggg ctctaggggg  3600
tatccccacg cgccctgtag cggcgcatta agcgcggcgg gtgtggtggt tacgcgcagc  3660
gtgaccgcta cacttgccag cgccctagcg cccgctcctt tcgctttctt cccttccttt  3720
ctcgccacgt tcgccggctt tccccgtcaa gctctaaatc gggggctccc tttagggttc  3780
cgatttagtg ctttacggca cctcgacccc aaaaaacttg attagggtga tggttcacgt  3840
agtgggccat cgccctgata gacggttttt cgccctttga cgttggagtc cacgttcttt  3900
aatagtggac tcttgttcca aactggaaca acactcaacc ctatctcggt ctattctttt  3960
gatttataag ggattttgcc gatttcggcc tattggttaa aaaatgagct gatttaacaa  4020
aaatttaacg cgaattaatt ctgtggaatg tgtgtcagtt agggtgtgga aagtccccag  4080
gctccccagc aggcagaagt atgcaaagca tgcatctcaa ttagtcagca accaggtgtg  4140
gaaagtcccc aggctcccca gcaggcagaa gtatgcaaag catgcatctc aattagtcag  4200
caaccatagt cccgccccta actccgccca tcccgcccct aactccgccc agttccgccc  4260
attctccgcc ccatggctga ctaatttttt ttatttatgc agaggccgag gccgcctctg  4320
```

```
cctctgagct attccagaag tagtgaggag gcttttttgg aggcctaggc ttttgcaaaa  4380
agctcccggg agcttgtata tccattttcg gatctgatca gcacgtgcta cgagatttcg  4440
attccaccgc cgccttctat gaaaggttgg gcttcggaat cgttttccgg gacgccggct  4500
ggatgatcct ccagcgcggg gatctcatgc tggagttctt cgcccacccc aacttgttta  4560
ttgcagctta taatggttac aaataaagca atagcatcac aaatttcaca aataaagcat  4620
tttttcact gcattctagt tgtggtttgt ccaaactcat caatgtatct tatcatgtct  4680
gtataccgtc gacctctagc tagagcttgg cgtaatcatg gtcatagctg tttcctgtgt  4740
gaaattgtta tccgctcaca attccacaca acatacgagc cggaagcata aagtgtaaag  4800
cctggggtgc ctaatgagtg agctaactca cattaattgc gttgcgctca ctgcccgctt  4860
tccagtcggg aaacctgtcg tgccagctgc attaatgaat cggccaacgc gcggggagag  4920
gcggtttgcg tattgggcgc tcttccgctt cctcgctcac tgactcgctg cgctcggtcg  4980
ttcggctgcg gcgagcggta tcagctcact caaaggcggt aatacggtta tccacagaat  5040
caggggataa cgcaggaaag aacatgtgag caaaaggcca gcaaaaggcc aggaaccgta  5100
aaaaggccgc gttgctggcg tttttccata ggctccgccc ccctgacgag catcacaaaa  5160
atcgacgctc aagtcagagg tggcgaaacc cgacaggact ataaagatac caggcgtttc  5220
cccctggaag ctccctcgtg cgctctcctg ttccgaccct gccgcttacc ggatacctgt  5280
ccgcctttct cccttcggga agcgtggcgc tttctcatag ctcacgctgt aggtatctca  5340
gttcggtgta ggtcgttcgc tccaagctgg gctgtgtgca cgaacccccc gttcagcccg  5400
accgctgcgc cttatccggt aactatcgtc ttgagtccaa cccggtaaga cacgacttat  5460
cgccactggc agcagccact ggtaacagga ttagcagagc gaggtatgta ggcggtgcta  5520
cagagttctt gaagtggtgg cctaactacg gctacactag aagaacagta tttggtatct  5580
gcgctctgct gaagccagtt accttcggaa aaagagttgg tagctcttga tccggcaaac  5640
aaaccaccgc tggtagcggt ggtttttttg tttgcaagca gcagattacg cgcagaaaaa  5700
aaggatctca agaagatcct ttgatctttt ctacggggtc tgacgctcag tggaacgaaa  5760
actcacgtta agggattttg gtcatgagat tatcaaaaag gatcttcacc tagatccttt  5820
taaattaaaa atgaagtttt aaatcaatct aaagtatata tgagtaaact tggtctgaca  5880
gttaccaatg cttaatcagt gaggcaccta tctcagcgat ctgtctattt cgttcatcca  5940
tagttgcctg actccccgtc gtgtagataa ctacgatacg ggagggctta ccatctggcc  6000
ccagtgctgc aatgataccg cgagacccac gctcaccggc tccagattta tcagcaataa  6060
accagccagc cggaagggcc gagcgcagaa gtggtcctgc aactttatcc gcctccatcc  6120
agtctattaa ttgttgccgg gaagctagag taagtagttc gccagttaat agtttgcgca  6180
acgttgttgc cattgctaca ggcatcgtgg tgtcacgctc gtcgtttggt atggcttcat  6240
tcagctccgg ttcccaacga tcaaggcgag ttacatgatc ccccatgttg tgcaaaaaag  6300
cggttagctc cttcggtcct ccgatcgttg tcagaagtaa gttggccgca gtgttatcac  6360
tcatggttat ggcagcactg cataattctc ttactgtcat gccatccgta agatgctttt  6420
ctgtgactgg tgagtactca accaagtcat tctgagaata gtgtatgcgg cgaccgagtt  6480
gctcttgccc ggcgtcaata cgggataata ccgcgccaca tagcagaact ttaaaagtgc  6540
tcatcattgg aaaacgttct tcggggcgaa aactctcaag gatcttaccg ctgttgagat  6600
ccagttcgat gtaacccact cgtgcaccca actgatcttc agcatctttt actttcacca  6660
gcgtttctgg gtgagcaaaa acaggaaggc aaaatgccgc aaaaaaggga ataagggcga  6720
cacggaaatg ttgaatactc atactcttcc tttttcaata ttattgaagc atttatcagg  6780
gttattgtct catgagcgga tacatatttg aatgtattta gaaaaataaa caaatagggg  6840
ttccgcgcac atttccccga aaagtgccac ctgacgtc                         6878

SEQ ID NO: 16           moltype = DNA  length = 7172
FEATURE                 Location/Qualifiers
misc_feature            1..7172
                        note = pCMV-LuEuC
source                  1..7172
                        mol_type = other DNA
                        organism = synthetic construct
SEQUENCE: 16
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
gtttaaactt aagcttggca ttccggtact gttggtaaag ccaccatgga agacgccaaa  960
aacataaaga aaggcccggc gccattctat ccgctggaag atggaaccgc tggagagcaa  1020
ctgcataagg ctatgaagag atacgccctg gttcctggaa caattgcttt tacagatgca  1080
catatcgagg tggacatcac ttacgctgag tacttcgaaa tgtccgttcg gttggcagaa  1140
gctatgaaac gatatgggct gaatacaaat cacagaatcg tcgtatgcag tgaaaactct  1200
cttcaattct ttatgccggt gttgggcgcg ttatttatcg gagttgcagt tgcgcccgcg  1260
aacgacattt ataatgaacg tgaattgctc aacagtatgg gcatttcgca gcctaccgtg  1320
gtgttcgttt ccaaaaaggg gttgcaaaaa attttgaacg tgcaaaaaaa gctcccaatc  1380
atccaaaaaa ttattatcat ggattctaaa acggattacc agggatttca gtcgatgtac  1440
acgttcgtca catctcatct acctcccggt tttaacccta gaaagatagt ctgcgtaaaa  1500
ttgacgcatg cattcttgaa atattgctct ctctttctaa atagcgcgaa tccgtcgctg  1560
tgcatttagg acatctcagt cgccgcttgg agctcccgtg aggcgtgctt gtcaatgcgg  1620
```

-continued taagtgtcac tgattttgaa ctataacgac cgcgtgagtc aaaatgacgc atgattatct 1680
tttacgtgac ttttaagatt taactcatac gataattata ttgttatttc atgttctact 1740
tacgtgataa cttattatat atatattttc ttgttataga tatctggcct aactggccgg 1800
taccgcgtta cataacttac ggtaaatggc ccgcctggct gaccgcccaa cgacccccgc 1860
ccattgacgt caataatgac gtatgttccc atagtaacgc caatagggac tttccattga 1920
cgtcaatggg tggagtattt acggtaaact gcccacttgg cagtacatca agtgtatcat 1980
atgccaagta cgccccctat tgacgtcaat gacggtaaat ggcccgcctg gcattatgcc 2040
cagtacatga ccttatggga ctttcctact tggcagtaca tctacgtatt agtcatcgct 2100
attaccatgg tctcgaggat atcaagatct ggcctcggcg gccaagcttg gcttttgtta 2160
ctttatagaa gaaattttga gtttttgttt tttttaata aataaataaa cataaataaa 2220
ttgtttgttg aatttattat tagtatgtaa gtgtaaatat aataaaactt aatatctatt 2280
caaattaata aataaacctc gatatacaga ccgataaaac acatgcgtca attttacgca 2340
tgattatctt taacgtacgt cacaatatga ttatctttct agggttaatg aatacgattt 2400
tgtgccagag tccttcgata gggacaagac aattgcactg atcatgaact cctctggatc 2460
tactggtctg cctaaaggtg tcgctctgcc tcatagaact gcctgcgtga gattctcgca 2520
tgccagagat cctatttttg gcaatcaaat cattccggat actgcgattt taagtgttgt 2580
tccattccat cacggttttg gaatgtttac tacactcgga tatttgatat gtggatttcg 2640
agtcgtctta atgtatagat ttgaagaaga gctgtttctg aggagccttc aggattacaa 2700
gattcaaagt gcgctgctgg tgccaaccct attctccttc ttcgccaaaa gcactctgat 2760
tgacaaatac gatttatcta atttacacga aattgcttct ggtggcgctc ccctctctaa 2820
ggaagtcggg gaagcggttg ccaagaggtt ccatctgcca ggtatcaggc aaggatatgg 2880
gctcactgag actacatcag ctattctgat tacacccgag gggatgata aaccgggcgc 2940
ggtcggtaaa gttgttccat tttttgaagc gaaggttgtg gatctggata ccgggaaaac 3000
gctgggcgtt aatcaaagag gcgaactgtg tgtgagaggt cctatgatta tgtccggtta 3060
tgtaaacaat ccggaagcga ccaacgcctt gattgacaag gatggatggc tacattctgg 3120
agacatagct tactgggacg aagacgaaca cttcttcatc gttgaccgcc tgaagtctct 3180
gattaagtac aaaggctatc aggtggctcc cgctgaattg gaatccatct tgctccaaca 3240
ccccaacatc ttcgacgcag gtgtcgcagg tcttcccgac gatgacgccg gtgaacttcc 3300
cgccgccgtt gttgttttgg agcacggaaa gacgatgacg gaaaaagaga tcgtggatta 3360
cgtcgccagt caagtaacaa ccgcgaaaaa gttgcgcgga ggagttgtgt ttgtggacga 3420
agtaccgaaa ggtcttaccg gaaaactcga cgcaagaaaa atcagagaga tcctcataaa 3480
ggccaagaag ggcggaaaga tcgccgtgta attctagagg gcccgcggtt cgaaggtaag 3540
cctatcccta accctctcct cggtctcgat tctacgcgta ccggtcatca tcaccatcac 3600
cattgagttt aaacccgctg atcagcctcg actgtgcctt ctagttgcca gccatctgtt 3660
gtttgcccct cccccgtgcc ttccttgacc ctggaaggtg ccactcccac tgtcctttcc 3720
taataaaatg aggaaattgc atcgcattgt ctgagtaggt gtcattctat tctggggggt 3780
ggggtggggc aggacagcaa gggggaggat tgggaagaca atagcaggca tgctggggat 3840
gcggtgggct ctatggcttc tgaggcggaa agaaccagct ggggctctag ggggtatccc 3900
cacgcgccct gtagcggcgc attaagcgcg gcgggtgtgg tggttacgcg cagcgtgacc 3960
gctacacttg ccagcgccct agcgcccgct cctttcgctt tcttcccttc ctttctcgcc 4020
acgttcgccg gctttccccg tcaagctcta aatcgggggc tccctttagg gttccgattt 4080
agtgctttac ggcacctcga ccccaaaaaa cttgattagg gtgatggttc acgtagtggg 4140
ccatcgccct gatagacggt ttttcgccct ttgacgttgg agtccacgtt ctttaatagt 4200
ggactcttgt tccaaactgg aacaacactc aaccctatct cggtctattc ttttgattta 4260
taagggattt tgccgatttc ggcctattgg ttaaaaaatg agctgattta acaaaaattt 4320
aacgcgaatt aattctgtgg aatgtgtgtc agttagggtg tggaaagtcc ccaggctccc 4380
cagcaggcag aagtatgcaa agcatgcatc tcaattagtc agcaaccagg tgtggaaagt 4440
ccccaggctc cccagcaggc agaagtatgc aaagcatgca tctcaattag tcagcaacca 4500
tagtcccgcc cctaactccg cccatcccgc ccctaactcc gcccagttcc gcccattctc 4560
cgccccatgg ctgactaatt ttttttattt atgcagaggc cgaggccgcc tctgcctctg 4620
agctattcca gaagtagtga ggaggctttt ttggaggcct aggcttttgc aaaaagctcc 4680
cgggagcttg tatatccatt ttcggatctg atcagcacgt gctacgagat ttcgattcca 4740
ccgccgcctt ctatgaaagg ttgggcttcg gaatcgtttt ccgggacgcc ggctggatga 4800
tcctccagcg cggggatctc atgctggagt tcttcgccca ccccaacttg tttattgcag 4860
cttataatgg ttacaaataa agcaatagca tcacaaattt cacaaataaa gcattttttt 4920
cactgcattc tagttgtggt ttgtccaaac tcatcaatgt atcttatcat gtctgtatac 4980
cgtcgacctc tagctagagc ttggcgtaat catggtcata gctgtttcct gtgtgaaatt 5040
gttatccgct cacaattcca cacaacatac gagccggaag cataaagtgt aaagcctggg 5100
gtgcctaatg agtgagctaa ctcacattaa ttgcgttgcg ctcactgccc gctttccagt 5160
cgggaaacct gtcgtgccag ctgcattaat gaatcggcca acgcgcgggg agaggcggtt 5220
tgcgtattgg gcgctcttcc gcttcctcgc tcactgactc gctgcgctcg gtcgttcggc 5280
tgcggcgagc ggtatcagct cactcaaagg cggtaatacg gttatccaca gaatcagggg 5340
ataacgcagg aaagaacatg tgagcaaaag gccagcaaaa ggccaggaac cgtaaaaagg 5400
ccgcgttgct ggcgtttttc cataggctcc gcccccctga cgagcatcac aaaaatcgac 5460
gctcaagtca gaggtggcga aacccgacag gactataaag ataccaggcg tttccccctg 5520
gaagctccct cgtgcgctct cctgttccga ccctgccgct taccggatac ctgtccgcct 5580
ttctcccttc gggaagcgtg gcgctttctc atagctcacg ctgtaggtat ctcagttcgg 5640
tgtaggtcgt tcgctccaag ctgggctgtg tgcacgaacc ccccgttcag cccgaccgct 5700
gcgccttatc cggtaactat cgtcttgagt ccaacccggt aagacacgac ttatcgccac 5760
tggcagcagc cactggtaac aggattagca gagcgaggta tgtaggcggt gctacagagt 5820
tcttgaagtg gtggcctaac tacggctaca ctagaagaac agtatttggt atctgcgctc 5880
tgctgaagcc agttaccttc ggaaaaagag ttggtagctc ttgatccggc aaacaaacca 5940
ccgctggtag cggtggtttt tttgtttgca agcagcagat tacgcgcaga aaaaaaggat 6000
ctcaagaaga tcctttgatc ttttctacgg ggtctgacgc tcagtggaac gaaaactcac 6060
gttaagggat tttggtcatg agattatcaa aaaggatctt cacctagatc cttttaaatt 6120
aaaaatgaag ttttaaatca atctaaagta tatatgagta aacttggtct gacagttacc 6180
aatgcttaat cagtgaggca cctatctcag cgatctgtct atttcgttca tccatagttg 6240
cctgactccc cgtcgtgtag ataactacga tacgggaggg cttaccatct ggccccagtg 6300
ctgcaatgat accgcgagac ccacgctcac cggctccaga tttatcagca ataaaccagc 6360

-continued

```
cagccggaag ggccgagcgc agaagtggtc ctgcaacttt atccgcctcc atccagtcta  6420
ttaattgttg ccgggaagct agagtaagta gttcgccagt taatagtttg cgcaacgttg  6480
ttgccattgc tacaggcatc gtggtgtcac gctcgtcgtt tggtatggct tcattcagct  6540
ccggttccca acgatcaagg cgagttacat gatcccccat gttgtgcaaa aaagcggtta  6600
gctccttcgg tcctccgatc gttgtcagaa gtaagttggc cgcagtgtta tcactcatgg  6660
ttatggcagc actgcataat tctcttactg tcatgccatc cgtaagatgc ttttctgtga  6720
ctggtgagta ctcaaccaag tcattctgag aatagtgtat gcggcgaccg agttgctctt  6780
gcccggcgtc aatacgggat aataccgcgc cacatagcag aactttaaaa gtgctcatca  6840
ttggaaaacg ttcttcgggg cgaaaactct caaggatctt accgctgttg agatccagtt  6900
cgatgtaacc cactcgtgca cccaactgat cttcagcatc ttttactttc accagcgttt  6960
ctgggtgagc aaaaacagga aggcaaaatg ccgcaaaaaa gggaataagg gcgacacgga  7020
aatgttgaat actcatactc ttcctttttc aatattattg aagcatttat cagggttatt  7080
gtctcatgag cggatacata tttgaatgta tttagaaaaa taaacaaata ggggttccgc  7140
gcacatttcc ccgaaaagtg ccacctgacg tc                                 7172

SEQ ID NO: 17          moltype = DNA  length = 5751
FEATURE                Location/Qualifiers
misc_feature           1..5751
                       note = pTTAAx5-EF1alpha-Luc
source                 1..5751
                       mol_type = other DNA
                       organism = synthetic construct
SEQUENCE: 17
accaatgctt aatcagtgag gcacctatct cagcgatctg tctatttcgt tcatccatag  60
ttgcctgact ccccgtcgtg tagataacta cgatacggga gggcttacca tctggcccca  120
gtgctgcaat gataccgcga gacccacgct caccggctcc agatttatca gcaataaacc  180
agccagccgg aagggccgag cgcagaagtg gtcctgcaac tttatccgcc tccatccagt  240
ctattaattg ttgccgggaa gctagagtaa gtagttcgcc agttaatagt ttgcgcaacg  300
ttgttgccat tgctacaggc atcgtggtgt cacgctcgtc gtttggtatg gcttcattca  360
gctccggttc ccaacgatca aggcgagtta catgatcccc catgttgtgc aaaaaagcgg  420
ttagctcctt cggtcctccg atcgttgtca gaagtaagtt ggccgcagtg ttatcactca  480
tggttatggc agcactgcat aattctctta ctgtcatgcc atccgtaaga tgcttttctg  540
tgactggtga gtactcaacc aagtcattct gagaatagtg tatgcggcga ccgagttgct  600
cttgcccggc gtcaatacgg gataataccg cgccacatag cagaacttta aaagtgctca  660
tcattggaaa acgttcttcg gggcgaaaac tctcaaggat cttaccgctg ttgagatcca  720
gttcgatgta acccactcgt gcacccaact gatcttcagc atcttttact ttcaccagcg  780
tttctgggtg agcaaaaaca ggaaggcaaa atgccgcaaa aaagggaata agggcgacac  840
ggaaatgttg aatactcata ctcttccttt ttcaatatta ttgaagcatt tatcagggtt  900
attgtctcat gagcggatac atatttgaat gtatttagaa aaataaacaa ataggggttc  960
cgcgcacatt tccccgaaaa gtgccacctg acgtcgacgg atcgggagat ctcccgatcc  1020
cctatggtgc actctcagta caatctgctc tgatgccgca tagttaagcc agtatctgct  1080
ccctgcttgt gtgttggagg tcgctgagta gtgcgcgagc aaaatttaag ctacaacaag  1140
gcaaggcttg accgacaatt gcatgaagaa tctgcttagg gttaggcgtt ttgcgctgct  1200
tcgcgatttc tagacggagt actgtcctcc gaagacgctt aaagacgctt aaagacgctt  1260
aaagacgctt aaagacgctt aaagacgctc ggaggacagt actccgtctg gtaccagaaa  1320
cgtgaggctc cggtgcccgt cagtgggcag agcgcacatc gcccacagtc cccgagaagt  1380
tggggggagg ggtcggcaat tgaaccggtg cctagagaag gtggcgcggg gtaaactggg  1440
aaagtgatgt cgtgtactgg ctccgccttt ttcccgaggg tgggggagaa ccgtatataa  1500
gtgcagtagt cgccgtgaac gttctttttc gcaacgggtt tgccgccaga acacaggtaa  1560
gtgccgtgtg tggttcccgc gggcctggcc tctttacggg ttatggccct tgcgtgcctt  1620
gaattacttc cacgcccctg gctgcagtac gtgattcttg atcccgagct tcgggttgga  1680
agtgggtggg agagttcgag gccttgcgct taaggagccc cttcgcctcg tgcttgagtt  1740
gaggcctggc ttgggcgctg gggccgccgc gtgcgaatct ggtggcacct tcgcgcctgt  1800
ctcgctgctt tcgataagtc tctagccatt taaaattttt gatgacctgc tgcgacgctt  1860
tttttctggc aagatagtct tgtaaatgcg ggccaagatc tgcacactgg tatttcggtt  1920
tttggggccg cgggcggcga cggggcccgt gcgtcccagc gcacatgttc ggcgaggcgg  1980
ggcctgcgag cgcggccacc gagaatcgga cgggggtagt ctcaagctgg ccggcctgct  2040
ctggtgcctg gcctcgcgcc gccgtgtatc gccccgccct gggcggcaag gctggcccgg  2100
tcggcaccag ttgcgtgagc ggaaagatgg ccgcttcccg gccctgctgc agggagctca  2160
aaatggagga cgcggcgctc gggagagcgg gcgggtgagt cacccacaca aaggaaaagg  2220
gcctttccgt cctcagccgt cgcttcatgt gactccacgg agtaccgggc gccgtccagg  2280
cacctcgatt agttctcgag cttttggagt acgtcgtctt taggttgggg ggaggggttt  2340
tatgcgatgg agtttcccca cactgagtgg gtggagactg aagttaggcc agcttggcac  2400
ttgatgtaat tctccttgga atttgccctt tttgagtttg gatcttggtt cattctcaag  2460
cctcagacag tggttcaaag tttttttctt ccatttcagg tgtcgtgaaa gctagcgttt  2520
aaacttaagc ttggcaatcc ggtactgttg gtaaagccac catggtcttc acactcgaag  2580
atttcgttgg ggactggcga cagacagccg gctacaacct ggaccaagtc cttgaacagg  2640
gaggtgtgtc cagtttgttt cagaatctcg gggtgtccgt aactccgatc caaaggattg  2700
tcctgagcgg tgaaaatggg ctgaagatcg acatccatgt catcatcccg tatgaaggtc  2760
tgagcggcga ccaaatgggc cagatcgaaa aaatttttaa ggtggtgtac cctgtggatg  2820
atcatcactt taaggtgatc ctgcactatg gcacactggt aatcgacggg gttacgccga  2880
acatgatcga ctatttcgga cggccgtatg aaggcatcgc cgtgttcgac ggcaaaaaga  2940
tcactgtaac agggaccctg tggaacggca acaaaattat cgacgagcgc ctgatcaacc  3000
ccgacggctc cctgctgttc cgagtaacca tcaacggagt gaccggctgg cggctgtgcg  3060
aacgcattct ggcgtaaggc cgcgactcta gagggcccgc ggttcgaagg taagcctatc  3120
cctaaccctc tcctcggtct cgattctacg cgtaccggtc atcatcacca tcaccattga  3180
gtttaaaccc gctgatcagc ctcgactgtg ccttctagtt gccagccatc tgttgtttgc  3240
ccctcccccg tgccttcctt gaccctggaa ggtgccactc ccactgtcct ttcctaataa  3300
aatgaggaaa ttgcatcgca ttgtctgagt aggtgtcatt ctattctggg gggtggggtg  3360
```

-continued

```
gggcaggaca gcaaggggga ggattgggaa gacaatagca ggcatgctgg ggatgcggtg  3420
ggctctatgg cttctgaggc ggaaagaacc agctggggct ctagggggta tccccacgcg  3480
ccctgtagcg gcgcattaag cgcggcgggt gtggtggtta cgcgcagcgt gaccgctaca  3540
cttgccagcg ccctagcgcc cgctcctttc gctttcttcc cttcctttct cgccacgttc  3600
gccggctttc cccgtcaagc tctaaatcgg gggctccctt tagggttccg atttagtgct  3660
ttacggcacc tcgaccccaa aaaacttgat tagggtgatg gttcacgtag tgggccatcg  3720
ccctgataga cggtttttcg ccctttgacg ttggagtcca cgttctttaa tagtggactc  3780
ttgttccaaa ctggaacaac actcaaccct atctcggtct attcttttga tttataaggg  3840
attttgccga tttcggccta ttggttaaaa aatgagctga tttaacaaaa atttaacgcg  3900
aattaattct gtggaatgtg tgtcagttag ggtgtggaaa gtccccaggc tccccagcag  3960
gcagaagtat gcaaagcatg catctcaatt agtcagcaac caggtgtgga aagtccccag  4020
gctccccagc aggcagaagt atgcaaagca tgcatctcaa ttagtcagca accatagtcc  4080
cgcccctaac tccgcccatc ccgcccctaa ctccgcccag ttccgcccat tctccgcccc  4140
atggctgact aatttttttt atttatgcag aggccgaggc cgcctctgcc tctgagctat  4200
tccagaagta gtgaggaggc ttttttggag gcctaggctt ttgcaaaaag ctcccgggag  4260
cttgtatatc cattttcgga tctgatcagc acgtgctacg agatttcgat tccaccgccg  4320
ccttctatga aaggttgggc ttcggaatcg ttttccggga cgccggctgg atgatcctcc  4380
agcgcgggga tctcatgctg gagttcttcg cccaccccaa cttgtttatt gcagcttata  4440
atggttacaa ataaagcaat agcatcacaa atttcacaaa taaagcattt ttttcactgc  4500
attctagttg tggtttgtcc aaactcatca atgtatctta tcatgtctgt ataccgtcga  4560
cctctagcta gagcttggcg taatcatggt catagctgtt tcctgtgtga aattgttatc  4620
cgctcacaat tccacacaac atacgagccg gaagcataaa gtgtaaagcc tggggtgcct  4680
aatgagtgag ctaactcaca ttaattgcgt tgcgctcact gcccgctttc cagtcgggaa  4740
acctgtcgtg ccagctgcat taatgaatcg gccaacgcgc ggggagaggc ggtttgcgta  4800
ttgggcgctc ttccgcttcc tcgctcactg actcgctgcg ctcggtcgtt cggctgcggc  4860
gagcggtatc agctcactca aaggcggtaa tacggttatc cacagaatca ggggataacg  4920
caggaaagaa catgtgagca aaaggccagc aaaaggccag gaaccgtaaa aaggccgcgt  4980
tgctggcgtt tttccatagg ctccgccccc ctgacgagca tcacaaaaat cgacgctcaa  5040
gtcagaggtg gcgaaacccg acaggactat aaagatacca ggcgtttccc cctggaagct  5100
ccctcgtgcg ctctcctgtt ccgaccctgc cgcttaccgg atacctgtcc gcctttctcc  5160
cttcgggaag cgtggcgctt tctcatagct cacgctgtag gtatctcagt tcggtgtagg  5220
tcgttcgctc caagctgggc tgtgtgcacg aaccccccgt tcagcccgac cgctgcgcct  5280
tatccggtaa ctatcgtctt gagtccaacc cggtaagaca cgacttatcg ccactggcag  5340
cagccactgg taacaggatt agcagagcga ggtatgtagg cggtgctaca gagttcttga  5400
agtggtggcc taactacggc tacactagaa gaacagtatt tggtatctgc gctctgctga  5460
agccagttac cttcggaaaa agagttggta gctcttgatc cggcaaacaa accaccgctg  5520
gtagcggtgg tttttttgtt tgcaagcagc agattacgcg cagaaaaaaa ggatctcaag  5580
aagatccttt gatcttttct acggggtctg acgctcagtg gaacgaaaac tcacgttaag  5640
ggattttggt catgagatta tcaaaaagga tcttcaccta gatcctttta aattaaaaat  5700
gaagttttaa atcaatctaa agtatatatg agtaaacttg gtctgacagt t           5751

SEQ ID NO: 18          moltype = RNA  length = 1785
FEATURE                Location/Qualifiers
source                 1..1785
                       mol_type = other RNA
                       organism = Trichoplusia ni
SEQUENCE: 18
atgggtagtt ctttagacga tgagcatatc ctctctgctc ttctgcaaag cgatgacgag  60
cttgttggtg aggattctga cagtgaaata tcagatcacg taagtgaaga tgacgtccag  120
agcgatacag aagaagcgtt tatagatgag gtacatgaag tgcagccaac gtcaagcggt  180
agtgaaatat tagacgaaca aaatgttatt gaacaaccag gttcttcatt ggcttctaac  240
agaatcttga ccttgccaca gaggactatt agaggtaaga ataaacattg ttggtcaact  300
tcaaagtcca cgaggcgtag ccgagtctct gcactgaaca ttgtcagatc tcaaagaggt  360
ccgacgcgta tgtgccgcaa tatatatgac ccacttttat gcttcaaact attttttact  420
gatgagataa tttcggaaat tgtaaaatgg acaaatgctg agatatcatt gaaacgtcgg  480
gaatctatga caggtgctac atttcgtgac acgaatgaag atgaaatcta tgctttcttt  540
ggtattctgg taatgacagc agtgagaaaa gataaccaca tgtccacaga tgacctcttt  600
gatcgatctt tgtcaatggt gtacgtctct gtaatgagtc gtgatcgttt tgattttttg  660
atacgatgtc ttagaatgga tgacaaaagt atacggccca cacttcgaga aaacgatgta  720
tttactcctg ttagaaaaat atgggatctc tttatccatc agtgcataca aaattacact  780
ccaggggctc atttgaccat agatgaacag ttacttggtt ttagaggacg gtgtccgttt  840
aggatgtata tcccaaacaa gccaagtaag tatggaataa aaatcctcat gatgtgtgac  900
agtggtacga agtatatgat aaatggaatg ccttatttgg gaagaggaac acagaccaac  960
ggagtaccac tcggtgaata ctacgtgaag gagttatcaa agcctgtgca cggtagttgt  1020
cgtaatatta cgtgtgacaa ttggttcacc tcaatccctt tggcaaaaaa cttactacaa  1080
gaaccgtata agttaaccat tgtgggaacc gtgcgatcaa acaaacgcga gataccggaa  1140
gtactgaaaa acagtcgctc caggccagtg ggaacatcga tgttttgttt tgacggaccc  1200
cttactctcg tctcatataa accgaagcca gctaagatgg tatacttatt atcatcttgt  1260
gatgaggatg cttctatcaa cgaaagtacc ggtaaaccgc aaatggttat gtattataat  1320
caaactaaag gcggagtgga cacgctagac caaatgtgtt ctgtgatgac ctgcagtagg  1380
aagacgaata ggtggcctat ggcattattg tacggaatga taaacattgc ctgcataaat  1440
tcttttatta tatacagcca taatgtcagt agcaagggag aaaaggttca aagtcgcaaa  1500
aaatttatga gaaacccttta catgagcctg acgtcatcgt ttatgcgtaa gcgtttagaa  1560
gctcctactt tgaagagata tttgcgcgat aatatctcta atattttgcc aaatgaagtg  1620
cctggtacat cagatgacag tactgaagag ccagtaatga aaaaacgtac ttactgtact  1680
tactgcccct ctaaaataag gcgaaaggca aatgcatcgt gcaaaaaatg caaaaaagtt  1740
atttgtcgag agcataatat tgatatgtgc caaagttgtt tctga                  1785

SEQ ID NO: 19          moltype = RNA  length = 1869
```

-continued

```
FEATURE              Location/Qualifiers
source               1..1869
                     mol_type = other RNA
                     organism = Trichoplusia ni
SEQUENCE: 19
atgggcggca gaaagaagag aagacagaga agaagacccc ccgccggcac cagcgtgagc  60
ctgaagaaga agagaaaggt gccccccgcc tcctccctcg atgacgagca cattctgtcc  120
gctctgctgc agtccgacga tgagctggtc ggagaagaca gcgatagcga ggtgagcgac  180
cacgtctccg aggacgacgt ccaaagcgac acagaggagg ccttcatcga cgaggtgcac  240
gaggtgcagc ctaccagcag cggctccgag atcctggacg agcagaacgt gatcgagcag  300
cccggcagct ccctggccag caacaggatc ctgaccctgc cccagaggac catcaggggc  360
aagaacaagc actgctggtc cacctccaag cccaccaggc ggagcagggt gtccgccctg  420
aacatcgtga gaagccagag gggccccacc aggatgtgca ggaacatcta cgaccccctg  480
ctgtgcttca agctgttctt caccgacgag atcatcagcg agatcgtgaa gtggaccaac  540
gccgagatca gcctgaagag gcgggagagc atgacctccg ccaccttcag ggacaccaac  600
gaggacgaga tctacgcctt cttcggcatc ctggtgatga ccgccgtgag gaaggacaac  660
cacatgagca ccgacgacct gttcgacaga tccctgagca tggtgtacgt gagcgtgatg  720
agcagggaca gattcgactt cctgatcaga tgcctgagga tggacgacaa gagcatcagg  780
cccaccctgc gggagaacga cgtgttcacc cccgtgagaa agatctggga cctgttcatc  840
caccagtgca tccagaacta caccccctggc gcccacctga ccatcgacga gcagctgctg  900
ggcttcaggg gcaggtgccc cttcagggtc tatatcccca acaagcccag caagtacggc  960
atcaagatcc tgatgatgtg cgacagcggc accaagtaca tgatcaacgg catgccctac  1020
ctgggcaggg gcacccagac caacggcgtg cccctgggcg agtactacgt gaaggagctg  1080
tccaagcccg tccacggcag ctgcagaaac atcacctgcg acaactggtt caccagcatc  1140
cccctggcca agaacctgct gcaggagccc tacaagctga ccatcgtggg caccgtgaga  1200
agcaacaaga gagagatccc cgaggtcctg aagaacagca ggtccaggcc cgtgggcacc  1260
agcatgttct gcttcgacgg ccccctgacc ctggtgtcct acaagcccaa gcccgccaag  1320
atggtgtacc tgctgtccag ctgcgacgag gacgccagca tcaacgagag caccggcaag  1380
ccccagatgg tgatgtacta caaccagacc aagggcggcg tggacaccct ggaccagatg  1440
tgcagcgtga tgacctgcag cagaaagacc aacaggtggc ccatggccct gctgtacggc  1500
atgatcaaca tcgcctgcat caacagcttc atcatctaca gccacaacgt gagcagcaag  1560
ggcgagaagg tgcagagccg gaaaaagttc atgcggaacc tgtacatggg cctgacctcc  1620
agcttcatga ggaagaggct ggaggccccc accctgaaga gatacctgag ggacaacatc  1680
agcaacatcc tgcccaaaga ggtgcccggc accagcgacg acagcaccga ggagcccgtg  1740
atgaagaaga ggacctactg cacctactgt cccagcaaga tcagaagaaa ggccagcgcc  1800
agctgcaaga agtgtaagaa ggtcatctgc cgggagcaca acatcgacat gtgccagagc  1860
tgtttctga                                                          1869
```

VECTOR SET FOR MEASURING TRANSPOSASE ACTIVITY, KIT, TRANSPOSASE ACTIVITY MEASURING METHOD, AND CELL SEPARATION METHOD

CROSS-REFERENCE TO RELATED APPLICATIONS

This application is a Continuation Application of PCT Application No. PCT/JP2021/033368 filed Sep. 10, 2021 and based upon and claiming the benefit of priority from Japanese Patent Application No. 2021-003669, filed Jan. 13, 2021, the entire contents of all of which are incorporated herein by reference.

REFERENCE TO A SEQUENCE LISTING

In accordance with 37 CFR § 1.831, the present specification makes reference to a Sequence Listing submitted electronically as a .xml file named "544837US_ST26.xml". The .xml file was generated on Sep. 22, 2022 and is 51,342 bytes in size. The entire contents of the Sequence Listing are hereby incorporated by reference.

FIELD

Embodiments described herein relate generally to a vector set for measuring transposase activity, a kit, a transposase activity measuring method, and a cell separation method.

BACKGROUND

In a technique of incorporating a nucleic acid into a genome of a cell, a transposase is used. The transposase is an enzyme having an activity of cutting out a DNA sequence in which a transposase recognition sequence is arranged at both ends, and an activity of inserting the cut-out DNA sequence into a transposase target sequence on a genome.

When such an enzyme is used or produced, it is important to confirm whether or not the enzyme works properly, that is, to confirm the activity of the enzyme in a necessary place. Therefore, a method for more easily confirming the activity of a transposase is required.

DETAILED DESCRIPTION

Figure 1:
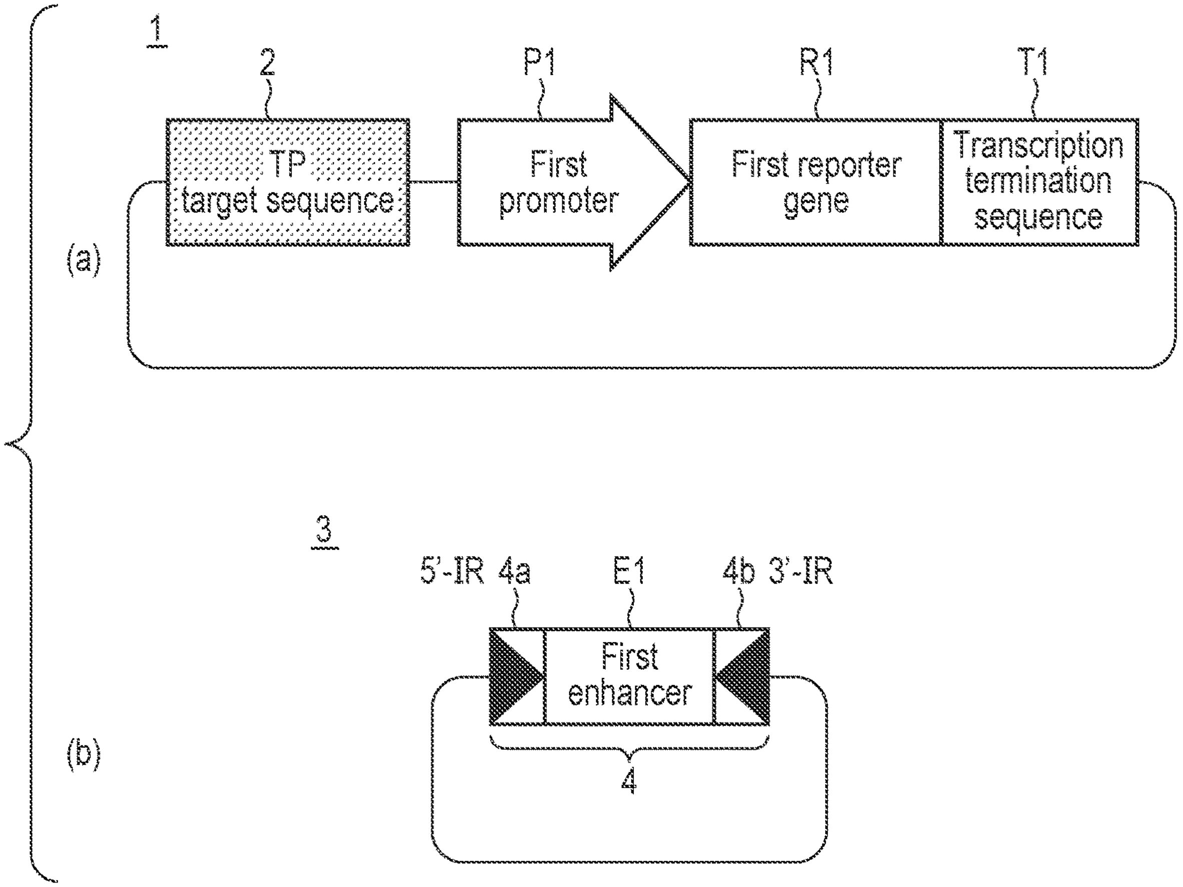
FIG. 1 is a diagram showing an example of a first vector and a second vector of a first embodiment.

In general, according to one embodiment, a vector set includes a first vector and a second vector. The first vector includes a transposase target sequence, a first promoter sequence and a first reporter gene. The second vector includes 5'-side transposase recognition sequence, a 3'-side transposase recognition sequence, and a first enhancer sequence disposed between the two recognition sequences.

Embodiments will be described hereinafter with reference to the accompanying drawings. Note that, in these embodiments, substantially the same structural elements will be designated by the same reference symbols sign and the explanations therefor may be partly omitted. Further, the drawings are only schematic, and therefore, the relation between the thickness of each element and its planar dimension, the ratio in thickness between the elements and the like may be different from those of the actual cases.

According to embodiments, a vector for measuring the activity of a transposase is provided. The transposase to be subjected to activity measurement is, for example, a DNA-type transposase. The DNA-type transposase is, for example, but not limited to, PiggyBac, SleepingBeauty, Frog Prince, Hsma, Minos, Tol1, Tol2, Passport, hAT, Ac/Ds, PIF, Harbinger, Harbinger3-DR, Himarl, Hermes, Tc3, or Mos1. The transposase may be modified from the above-described transposase.

In the present specification, the activity of a transposase means a "cutting activity" for cutting out a sequence having a transposase recognition sequence at both ends from a nucleic acid sequence, and an "incorporating activity" for incorporating the cut-out sequence into a transposase target sequence on a genome.

First Embodiment

Vectors for measuring transposase incorporating activity

A vector for measuring transposase incorporating activity (hereinafter, also referred to as a "first vector") according to an embodiment is described below. As shown in part (a) of FIG. 1, a first vector 1 according to a first embodiment includes: a transposase target sequence 2 (in the drawing, "TP target sequence"); a first promoter sequence P1 ligated to downstream of the transposase target sequence 2; a first reporter gene R1 ligated to downstream of the first promoter sequence P1; and a first transcription termination sequence T1 ligated to downstream of the first reporter gene R1.

The transposase target sequence 2 is a sequence as a target into which a transposase is to incorporate a DNA sequence. In other words, the transposase incorporates the cut-out DNA sequence into the transposase target sequence 2. The transposase target sequence 2 is, for example, a sequence including a plurality of TTAA sequences (T: thymine, A: adenine), and is preferably, for example, a sequence containing five TTAA sequences. Alternatively, a sequence including a plurality of TA sequences can also be used.

For example, the transposase target sequence 2 is preferably a base sequence shown in Table 1 below.

TABLE 1

| Transpose target sequence 2 |
|---|
| (SEQ ID NO: 1) |
| agacgcttaa agacgcttaa agacgcttaa agacgcttaa agacgcttaa agacgc 56 |

As is described in detail below, in a first embodiment, when the first vector 1 is used, a first enhancer sequence E1 can be incorporated into the transposase target sequence 2.

The first promoter sequence P1 is operably ligated to downstream of the transposase target sequence 2 so that gene activation on downstream of the first promoter sequence P1 is promoted when the first enhancer sequence E1 is incorporated into the transposase target sequence 2.

Herein, ligating encompasses a case where two sequences are ligated without other sequences being interposed between the two sequences, and a case where an arbitrary sequence is interposed between the two sequences. The arbitrary sequence is, for example, a spacer sequence. The spacer sequence is a nucleic acid sequence that is different from the sequences of the transposase target sequence 2, the first promoter sequence P1, the first reporter gene R1, the first transcription termination sequence T1, and their complementary sequences, and does not adversely affect the activity of these sequences.

The first promoter sequence P1 may be a base sequence of a known promoter capable of initiating transcription of a gene ligated downstream by its activity. The first promoter sequence P1 may be a promoter capable of expressing a gene by the presence of an enhancer. Alternatively, the first promoter sequence P1 may be a promoter having a low gene expression level when it is alone, but having a high gene expression level by the presence of an enhancer.

The first promoter sequence P1 is preferably, for example, a cytomegalovirus (CMV) promoter, a simian virus 40 (SV40) promoter, a thymidine kinase (TK) promoter, a ubiquitin (UbC) promoter, a human polypeptide chain elongation factor (EF1α) promoter, a hybrid (CAG) promoter of a cytomegalovirus enhancer and a chicken β-actin promoter, a mouse stem cell virus (MSCV) promoter, a Rous sarcoma virus (RSV) promoter, or the like. However, the first promoter sequence P1 is not limited to those listed above as long as it has a promoter function, and may be obtained by substituting or deleting any base in the base sequence of the promoter.

The first promoter sequence P1 is preferably a CMV promoter (SEQ ID NO: 2) having the base sequence shown in Table 2 or a promoter sequence (SEQ ID NO: 3) of the human polypeptide chain elongation factor gene (EF1α) shown in Table 3.

TABLE 2

| CMV promoter sequence (first promoter sequence P1, SEQ ID NO: 2) |
|---|
| cgatgtacgg gccagatata cgcgttgaca ttgattattg actagttatt aatagtaatc 60 |
| aattacgggg tcattagttc atagcccata tatggagttc cgcgttacat aacttacggt 120 |
| aaatggcccg cctggctgac cgcccaacga cccccgccca ttgacgtcaa taatgacgta 180 |
| tgttcccata gtaacgccaa tagggacttt ccattgacgt caatgggtgg agtatttacg 240 |
| gtaaactgcc cacttggcag tacatcaagt gtatcatatg ccaagtacgc cccctattga 300 |
| cgtcaatgac ggtaaatggc ccgcctggca ttatgcccag tacatgacct tatgggactt 360 |
| tcctacttgg cagtacatct acgtattagt catcgctatt accatggtga tgcggttttg 420 |
| gcagtacatc aatgggcgtg gatagcggtt tgactcacgg ggatttccaa gtctccaccc 480 |
| cattgacgtc aatgggagtt tgttttggca ccaaaatcaa cgggactttc caaaatgtcg 540 |
| taacaactcc gccccattga cgcaaatggg cggtaggcgt gtacggtggg aggtctatat 600 |
| aagcagagct ctctggctaa ctagagaacc cactgcttac tggcttatcg aaat 654 |

TABLE 3

| Human polypeptide chain elongation factor gene (EF1α) promoter sequence (first promoter sequence P1, SEQ ID NO: 3) |
|---|
| cgtgaggctc cggtgcccgt cagtgggcag agcgcacatc gcccacagtc cccgagaagt 60 |
| tggggggagg ggtcggcaat tgaaccggtg cctagagaag gtggcgcggg gtaaactggg 20 |
| aaagtgatgt cgtgtactgg ctccgccttt ttcccgaggg tgggggagaa ccgtatataa 180 |
| gtgcagtagt cgccgtgaac gttctttttc gcaacgggtt tgccgccaga acacaggtaa 240 |
| gtgccgtgtg tggttcccgc gggcctggcc tctttacggg ttatggccct tgcgtgcctt 300 |

TABLE 3-continued

| Human polypeptide chain elongation factor gene (EF1α) promoter sequence (first promoter sequence P1, SEQ ID NO: 3) |
|---|
| gaattacttc cacgcccctg gctgcagtac gtgattcttg atcccgagct tcgggttgga 360 |
| agtgggtggg agagttcgag gccttgcgct taaggagccc cttcgcctcg tgcttgagtt 420 |
| gaggcctggc ttgggcgctg gggccgccgc gtgcgaatct ggtggcacct tcgcgcctgt 480 |
| ctcgctgctt tcgataagtc tctagccatt taaaattttt gatgacctgc tgcgacgctt 540 |
| tttttctggc aagatagtct tgtaaatgcg ggccaagatc tgcacactgg tatttcggtt 600 |
| tttggggccg cgggcggcga cggggcccgt gcgtcccagc gcacatgttc ggcgaggcgg 660 |
| ggcctgcgag cgcggccacc gagaatcgga cgggggtagt ctcaagctgg ccggcctgct 720 |
| ctggtgcctg gcctcgcgcc gccgtgtatc gccccgccct gggcggcaag gctggcccgg 780 |
| tcggcaccag ttgcgtgagc ggaaagatgg ccgcttcccg gccctgctgc agggagctca 840 |
| aaatggagga cgcggcgctc gggagagcgg gcgggtgagt cacccacaca aaggaaaagg 900 |
| gcctttccgt cctcagccgt cgcttcatgt gactccacgg agtaccgggc gccgtccagg 960 |
| cacctcgatt agttctcgag cttttggagt acgtcgtctt taggttgggg ggaggggttt 1020 |
| tatgcgatgg agtttcccca cactgagtgg gtggagactg aagttaggcc agcttggcac 1080 |
| ttgatgtaat tctccttgga atttgccctt tttgagtttg gatcttggtt cattctcaag 1140 |
| cctcagacag tggttcaaag tttttttctt ccatttcagg tgtcgtga 1188 |

The first reporter gene R1 is operably ligated to downstream of the first promoter sequence P1 so that its gene expression is regulated by the activity of the first promoter sequence P1.

The first reporter gene R1 may be a base sequence of a gene encoding a known reporter protein. The first reporter gene R1 is, for example, a gene of a fluorescent protein such as a blue fluorescent protein gene, a green fluorescent protein gene, or a red fluorescent protein gene; a gene of luminescent enzyme proteins such as firefly luciferase gene, *renilla* luciferase gene or NanoLuc (registered trademark) luciferase gene; a gene of active oxygen generating enzymes such as xanthine oxidase genes or nitric oxide synthase genes; or a gene of a chromogenic enzyme protein such as a β-galactosidase gene or a chloramphenicol acetyltransferase gene. However, the first reporter gene R1 is not limited to the reporter genes listed above as long as the function as a reporter is not lost, and may be obtained by substituting or deleting any base of the base sequence of the above-described reporter gene.

For example, as the first reporter gene R1, a firefly luciferase gene shown in Table 4, a luciferase gene derived from Oplophorus gracilirostris shown in Table 5, or the like can be used.

TABLE 4

| Firefly luciferase gene |
|---|
| (SEQ ID NO: 4) |
| atggaagacg ccaaaaacat aaagaaaggc ccggcgccat tctatccgct ggaagatgga 60 |
| accgctggag agcaactgca taaggctatg aagagatacg ccctggttcc tggaacaatt 120 |
| gcttttacag atgcacatat cgaggtggac atcacttacg ctgagtactt cgaaatgtcc 180 |
| gttcggttgg cagaagctat gaaacgatat gggctgaata caaatcacag aatcgtcgta 240 |
| tgcagtgaaa actctcttca attctttatg ccggtgttgg gcgcgttatt tatcggagtt 300 |
| gcagttgcgc ccgcgaacga catttataat gaacgtgaat tgctcaacag tatgggcatt 360 |
| tcgcagccta ccgtggtgtt cgtttccaaa aaggggttgc aaaaaatttt gaacgtgcaa 420 |
| aaaaagctcc caatcatcca aaaaattatt atcatggatt ctaaaacgga ttaccaggga 480 |
| tttcagtcga tgtacacgtt cgtcacatct catctacctc ccggttttaa tgaatacgat 540 |
| tttgtgccag agtccttcga tagggacaag acaattgcac tgatcatgaa ctcctctgga 600 |
| tctactggtc tgcctaaagg tgtcgctctg cctcatagaa ctgcctgcgt gagattctcg 660 |
| catgccagag atcctatttt tggcaatcaa atcattccgg atactgcgat tttaagtgtt 720 |

TABLE 4-continued

| Firefly luciferase gene | |
|---|---|
| gttccattcc atcacggttt tggaatgttt actacactcg gatatttgat atgtggattt | 780 |
| cgagtcgtct taatgtatag atttgaagaa gagctgtttc tgaggagcct tcaggattac | 840 |
| aagattcaaa gtgcgctgct ggtgccaacc ctattctcct tcttcgccaa aagcactctg | 900 |
| attgacaaat acgatttatc taatttacac gaaattgctt ctggtggcgc tcccctctct | 960 |
| aaggaagycg gggaagcggt tgccaagagg ttccatctgc caggtatcag gcaaggatat | 1020 |
| gggctcactg agactacatc agctattctg attacacccg agggggatga taaaccgggc | 1080 |
| gcggtcggta aagttgttcc attttttgaa gcgaaggttg tggatctgga taccgggaaa | 1140 |
| acgctgggcg ttaatcaaag aggcgaactg tgtgtgagag gtcctatgat tatgtccggt | 1200 |
| tatgtaaaca atccggaagc gaccaacgcc ttgattgaca aggatggatg gctacattct | 1260 |
| ggagacatag cttactggga cgaagacgaa cacttcttca tcgttgaccg cctgaagtct | 1320 |
| ctgattaagt acaaaggcta tcaggtggct cccgctgaat tggaatccat cttgctccaa | 1380 |
| caccccaaca tcttcgacgc aggtgtcgca ggtcttcccg acgatgacgc cggtgaacgt | 1440 |
| cccgccgccg ttgttgtttt ggagcacgga aagacgatga cggaaaaaga gatcgtggat | 1500 |
| tacgtcgcca gtcaagtaac aaccgcgaaa aagttgcgcg gaggagttgt gtttgtggac | 1560 |
| gaagtaccga aaggtcttac cggaaaactc gacgcaagaa aaatcagaga gatcctcata | 1620 |
| aaggccaaga agggcggaaa gatcgccgtg taa | |

TABLE 5

| Oplophorus gracilirostris luciferase | |
|---|---|
| | (SEQ ID NO: 5) |
| agcttggcaa tccggtactg ttggtaaagc caccatggtc ttcacactcg aagatttcgt | 60 |
| tggggactgg cgacagacag ccggctacaa cctggaccaa gtccttgaac agggaggtgt | 120 |
| gtccagtttg tttcagaatc tcggggtgtc cgtaactccg atccaaagga ttgtcctgag | 180 |
| cggtgaaaat gggctgaaga tcgacatcca tgtcatcatc ccgtatgaag gtctgagcgg | 240 |
| cgaccaaatg ggccagatcg aaaaaatttt taaggtggtg taccctgtgg atgatcatca | 300 |
| ctttaaggtg atcctgcact atggcacact ggtaatcgac ggggttacgc cgaacatgat | 360 |
| cgactatttc ggacggccgt atgaaggcat cgccgtgttc gacggcaaaa agatcactgt | 420 |
| aacagggacc ctgtggaacg gcaacaaaat tatcgacgag cgcctgatca accccgacgg | 480 |
| ctccctgctg ttccgagtaa ccatcaacgg agtgaccggc tggcggctgt gcgaacgcat | 540 |
| tctggcgtaa | 550 |

The first transcription termination sequence T1 is operably ligated to downstream of the first reporter gene R1 so as to terminate the transcription of the first reporter gene R1. The first transcription termination sequence T1 is, for example, a poly(A) addition signal sequence of simian virus 40 (SV40), a poly(A) addition signal sequence of a bovine growth hormone gene, an artificially synthesized poly(A) addition signal sequence, or the like. However, the first transcription termination sequence T1 is not limited thereto, and as long as it has a function as a transcription termination sequence, another sequence, a modified base sequence of the above-described transcription termination sequence, or the like may be used.

It is preferable to use a base sequence of a bovine growth hormone transcription termination sequence or a base sequence of a SV40 transcription termination sequence, which is shown in Table 6 and Table 7.

TABLE 6

| Bovine growth hormone transcription termination sequence (first transcription termination sequence T1, SEQ ID NO: 6) | |
|---|---|
| gtttaaaccc gctgatcagc ctcgactgtg ccttctagtt gccagccatc tgttgtttgc | 60 |
| ccctcccccg tgccttcctt gaccctggaa ggtgccactc ccactgtcct ttcctaataa | 120 |
| aatgaggaaa ttgcatcgca ttgtctgagt aggtgtcatt ctattctggg gggtggggtg | 180 |
| gggcaggaca gcaaggggga ggattgggaa gacaatagca ggcatgct | 228 |

TABLE 7

| SV 40 transcription termination sequence (first transcription termination sequence T1, SEQ ID NO: 7) | |
|---|---|
| cagacatgat aagatacatt gatgagtttg gacaaaccac aactagaatg cagtgaaaaa | 60 |
| aatgctttat ttgtgaaatt tgtgatgcta ttgctttatt tgtaaccatt ataagctgca | 120 |
| ataaacaagt t | 131 |

The first vector 1 is, for example, a circular double-stranded DNA molecule. The first vector 1 is, for example, a plasmid vector.

The first vector 1 may contain any base sequence in addition to the above sequence. Such a base sequence may be, for example, a base sequence having a specific function, or a sequence having no function.

The base sequence having a function is, for example, an additional reporter gene expression unit, a drug resistance gene, a replication initiation protein expression unit, and/or a replication initiation sequence.

The drug resistance gene can be used, for example, for screening of cells into which the vector has been introduced. As the drug resistance gene, for example, an ampicillin resistance gene, a kanamycin resistance gene, a chloramphenicol resistance gene, a streptomycin resistance gene, a tetracycline resistance gene, a hygromycin resistance gene, a puromycin resistance gene, a blasticidin resistance gene, or the like can be used.

The replication initiation sequence is a sequence to which the replication initiation protein binds in order to initiate the replication of the first vector 1. When the first vector 1 is replicated, the reporter protein mass expressed from the first reporter gene R1 increases, and the activity of transposase can be measured with higher sensitivity. As the replication initiation sequence, for example, a replication initiation sequence derived from simian virus 40, Epstein-Barr virus, mouse polyomavirus, ColE1, or the like can be used.

The replication initiation protein may be originally present in a cell into which the first vector 1 is to be introduced, or may be introduced into the cell by a vector containing a replication initiation protein expression unit different from that of the first vector 1. The replication initiation protein may be expressed from the replication initiation protein expression unit, which may be provided in the first vector 1.

Second vector

The transposase activity measuring method using the first vector 1, is performed by using a vector set containing any one of the above-described first vectors 1, and a second vector. The second vector is described below.

As shown in an example in part (b) of FIG. 1, the second vector 3 includes at least a sequence for being cut 4 that can be cut out by transposase. The sequence for being cut 4 includes a 5'-side transposase recognition sequence ("5'-IR" in the drawing) 4a, a 3'-side transposase recognition sequence ("3'-IR" in the drawing) 4b, and a first enhancer sequence E1 disposed between the two recognition sequences.

These two recognition sequences are sequences that the transposase recognizes and binds to so as to cut out the sequence for being cut 4. The 5'-side transposase recognition sequence 4a and the 3'-side transposase recognition sequence 4b are, for example, inverted repeat sequences (IR), which include the same sequence in mutually opposite directions. The base sequence of the recognition sequence is selected according to the type of transposase whose activity is to be measured. Examples of the 5'-side transposase recognition sequence 4a and the 3'-side transposase recognition sequence 4b when the transposase is PiggyBac are shown in Tables 8 and 9 below, respectively.

TABLE 8

| 5'-IR of piggyBac (SEQ ID NO: 8) | |
|---|---|
| ttaaccctag aaagatagtc tgcgtaaaat tgacgcatgc attcttgaaa tattgctctc | 60 |
| tctttctaaa tagcgcgaat ccgtcgctgt gcatttagga catctcagtc gccgcttgga | 120 |
| gctcccgtga ggcgtgcttg tcaatgcggt aagtgtcact gattttgaac tataacgacc | 180 |
| gcgtgagtca aaatgacgca tgattatctt ttacgtgact tttaagattt aactcatacg | 240 |
| ataattatat tgttatttca tgttctactt acgtgataac ttattatata tatattttct | 300 |
| tgttatagat a | 311 |

TABLE 9

| 3'-IR of piggyBac (SEQ ID NO: 9) | |
|---|---|
| ttttgttact ttatagaaga aattttgagt ttttgttttt ttttaataaa taaataaaca | 60 |
| taaataaatt gtttgttgaa tttattatta gtatgtaagt gtaaatataa taaaacttaa | 120 |
| tatctattca aattaataaa taaacctcga tatacagacc gataaaacac atgcgtcaat | 180 |
| tttacgcatg attatcttta acgtacgtca caatatgatt atcttttcag ggttaa | 236 |

An example of the base sequence of either one of the 5'-side transposase recognition sequence 4a and the 3'-side transposase recognition sequence 4b when the transposase is SleepingBeauty, is shown in Table 10 below. The other may include, for example, an inverted repeat sequence of the sequence shown below.

TABLE 10

| SleepingBeauty recognition sequence (SEQ ID NO: 10) | |
|---|---|
| tatacagttg aagtcggaag tttacataca cytwagccaa atacatttaa actcactttt | 60 |
| tcacaattcc tgacatttaa tcctagtaaa aattccctgt cttaggtcag ttaggatcac | 120 |
| cactttattt taagaatgtg aaatatcaga ataatagtag agagaatgat gtktacakac | 180 |
| asdtcatttc agcttttatt tctttcatca cattyccagt gggtcagaag tgtacataca | 240 |
| cgvkct | 246 |

The first enhancer sequence E1 may be any known enhancer capable of promoting the activation of the first promoter sequence P1 and promoting the expression of a gene ligated to downstream thereof. The first enhancer sequence E1 can be selected according to, for example, the type of the first promoter sequence P1. As the first enhancer sequence E1, it is preferable to use, for example, a CMV enhancer, an SV40 enhancer, an RSV enhancer, a mouse retroviral terminal repeat (MLV LTR) enhancer, or the like. However, the first enhancer sequence E1 is not limited to the enhancer sequences listed above as long as the function as an enhancer is not lost, and may be obtained by substituting or deleting any base of the above-described enhancer sequence.

Table 11 shows an example of the base sequence of the enhancer sequence when the first promoter sequence P1 is a CMV promoter.

TABLE 11

| Enhancer sequence (SEQ ID NO: 11) | |
|---|---|
| gcgttacata acttacggca aatggcccgc ctggctgacc gcccaacgac ccccgcccat | 60 |
| tgacgtcaat aatgacgtat gttcccatag taacgccaat agggactttc cattgacgtc | 120 |
| aatgggtgga gtatttacgg taaactgccc acttggcagt acatcaagtg tatcatatgc | 180 |
| caagtacgcc ccctattgac gtcaatgacg gtaaatggcc cgcctggcat tatgcccagt | 240 |
| acatgacctt atgggactct cctacttggc agtacatcta cgtattagtc atcgctatta | 300 |
| ccatggt | 307 |

The second vector 3 may contain an arbitrary base sequence in addition to the above-described sequences. Such a base sequence may be, for example, a base sequence having a specific function, or a sequence having no function. The base sequence having a function is, for example, a reporter gene expression unit, a drug resistance gene, a replication initiation protein expression unit, and/or a replication initiation sequence.

The second vector 3 is, for example, a circular double-stranded DNA molecule. The second vector 3 is, for example, a plasmid vector.

Transposase activity measuring method

Figure 2:
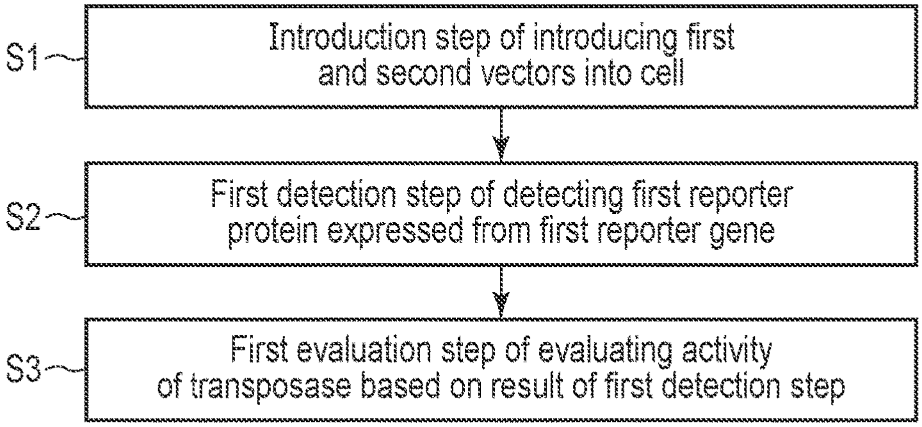
FIG. 2 is a flowchart showing an example of a transposase activity measuring method of a first embodiment.

A transposase activity measuring method using the first vector 1 and the second vector 3 is described below. The transposase activity measuring method includes, for example, the following steps shown in FIG. 2:

(S1) an introduction step of introducing the first vector and the second vector into a cell;

(S2) a first detection step of detecting a first reporter protein expressed from a first reporter gene; and (S3) a first evaluation step of evaluating the activity of a transposase from the result of detection of the first reporter protein.

An example of the method of the embodiment is described below in detail.

First, cells are prepared. The cells may be, for example, cells derived from humans, animals, or plants, or cells derived from microorganisms such as bacteria or fungi. The cells are preferably animal cells, more preferably mammalian cells, and most preferably human cells. The cells may be cells taken out of a living body, for example, cells separated from a body fluid such as blood, a tissue, a biopsy, or the like. The cells may be, for example, isolated cells, cultured cells, or established cells. Alternatively, the cells may be cells in a living body.

In a cell, there may be a transposase whose activity is to be measured. The transposase may be introduced, transcribed, and expressed in a cell, for example, in the form of a nucleic acid encoding it, for example, a DNA or an RNA. Alternatively, it may be in the form of a protein or a peptide introduced into a cell. Alternatively, it may be incorporated into the genome of a cell in advance, and expressed.

Next, the first vector 1 and the second vector 3 are introduced into the cell (introduction step S1). For example, when the cell is in a state of being taken out of a living body, the introduction step S1 can be performed by a known method such as a liposome method, a lipofection method, an electroporation method, a calcium phosphate co-precipitation method, a cationic polymer method, a microinjection method, a particle gun method, or a sonoporation method.

In particular, it is preferable to use a liposome method. In the liposome method, the first vector 1 and the second vector 3 are encapsulated in a liposome (lipid particle), and a composition or the like which contains it is brought into contact with a cell, so that, for example, the lipid particle is taken into the cell by endocytosis, and those encapsulated are released into the cell. Details of the lipid particles are described in the description of the following embodiment of a kit.

When the cell is a cell in a living body, the introduction can be performed by, for example, injecting or instilling a composition containing the first vector 1 and the second vector 3 into the living body. The composition may contain, for example, the lipid particles encapsulating the first vector 1 and the second vector 3.

When a transposase is introduced into a cell, the transposase may be introduced simultaneously with the introduction of the first vector 1 and the second vector 3, or either of these may be introduced earlier.

Figure 3:
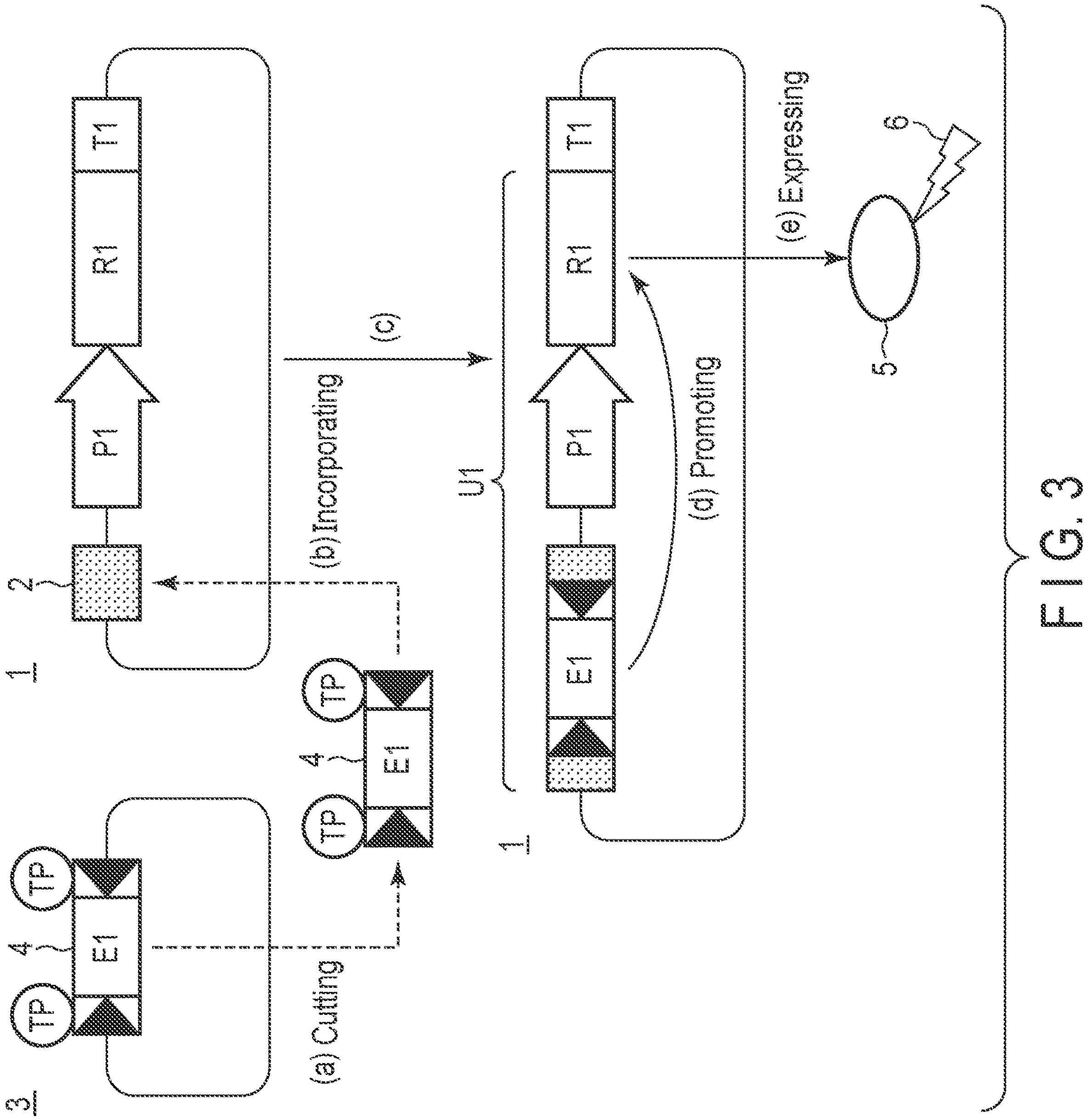
FIG. 3 is a diagram showing an example of the behavior of each vector after the introduction step of a first embodiment.

After the introduction step S1, for example, as shown in FIG. 3, the active transposase TP cuts out the sequence for being cut 4 from the second vector 3 (part (a) of FIG. 3). Next, the sequence for being cut 4 is introduced into the transposase target sequence 2 of the first vector 1 (part (b) of FIG. 3). That is, the sequence for being cut 4 is transferred. As a result, the first enhancer sequence E1 is incorporated into the first vector 1, and a first gene expression unit U1 containing the first enhancer sequence E1, the first promoter sequence P1, and the first reporter gene R1 is formed in the first vector 1 (part (c) of FIG. 3). The first enhancer sequence E1 promotes the expression of the first reporter gene R1 (part (d) of FIG. 3). As a result, the expression level of the first reporter protein 5 increases (part (e) of FIG. 3). The first reporter protein 5 generates a first signal 6.

The first signal 6 is a detectable signal obtained according to the type of the first reporter protein 5, and is, for example, fluorescence, chemiluminescence, bioluminescence, biochemiluminescence, coloration, or the like, or alternatively, presentation of a molecule such as a protein.

The first signal 6 is emitted from the first reporter protein 5 itself, or is generated by a reaction between the first reporter protein 5 and a specific substance (hereinafter, it is described as "first substance"), for example, an enzymatic reaction, binding, or the like. For example, when the first reporter protein 5 is an enzyme, the first substance is a substrate thereof. For example, when the first reporter protein 5 is luciferase, the first substance is luciferin.

Alternatively, the first signal 6 may be a signal derived from a further detection reagent (hereinafter, it is described as a "second substance") for detecting the presence of a substance generated by a reaction between the first reporter protein 5 and a specific substance.

Next, the first reporter protein 5 is detected (the first detection step S2). The detection of the first reporter protein 5 can be performed, for example, by detecting the first signal 6. The detection may be performed by using any known method selected according to the type of the first reporter protein 5 or the first signal 6.

Detection can be performed, for example, in a living cell. However, it may be performed in an extract obtained by extracting the first reporter protein 5 from the cell.

For example, when the first substance and/or the second substance is used, these substances can be added to the cell at the beginning of the first detection step S2. These substances may be added to the culture medium for the cell or may be introduced into the cell. Alternatively, it may be added to a reporter protein extract obtained from the cell.

When the first reporter protein 5 is a fluorescent protein, the first signal 6 is obtained as fluorescence generated from the fluorescent protein by irradiating the cell with excitation light. The fluorescence (the first signal 6) can be detected by visual observation, a microscope, a flow cytometer, image analysis software, a fluorometer, or the like.

When the first reporter protein 5 is luciferase, luciferin is added thereto so that the first signal 6 is obtained as chemiluminescence. The chemiluminescence (the first signal 6) can be detected by visual observation, a microscope, a flow cytometer, image analysis software, a luminometer, or the like.

When the first reporter protein 5 is β-galactosidase, a substrate such as 5-bromo-4-chloro-3-indolyl-β-D-galactopyranoside (X-Gal) or o-nitrophenyl-β-D-galactopyranoside (ONPG) is added, so that a first signal 6 is obtained as the absorbance of a cell solution or an extract. The absorbance (the first signal 6) can be detected by an absorptiometer, a spectrophotometer, a turbidimeter, or the like.

When the first reporter protein 5 is a nitric oxide synthase or a xanthine oxidase, active oxygen, which is generated by adding substrate, is obtained as the first signal 6. Active oxygen (the first signal 6) can be detected by an electron spin resonance apparatus (ESR apparatus) or the like.

When the first reporter protein 5 is a heavy metal binding protein, a heavy metal, which is bound to the reporter protein by adding detectable heavy metals, is obtained as the first signal 6. The heavy metal (the first signal 6) can be detected by a magnetic resonance imaging apparatus, a nuclear medicine diagnosis apparatus, an MRI imaging apparatus, or an X-ray computed tomography apparatus.

For example, since the intensity of the first signal 6 correlates with the expression level of the first reporter protein 5, the intensity of the expression of the first reporter protein 5 can be determined based on the intensity of the first signal 6. Alternatively, the first reporter protein 5 may be directly quantified.

Next, the activity of the transposase is evaluated from the result of detection of the first reporter protein 5 (the first evaluation step S3).

For example, when the first reporter protein 5 is highly expressed, it can be evaluated that the transposase TP at least has a good incorporating activity.

Here, when "the first reporter protein 5 is highly expressed" is described, it encompasses a case where the first reporter protein 5 (the first signal 6) is detected or its value equal to or more than a threshold value is obtained, a case where the expression level (the intensity of the first signal 6) of the first reporter protein 5 is increased, a case where the amount of an increase is equal to or more than a threshold value or more, and the like. When "having a good incorporating activity" is described, it encompasses having an incorporating activity and having a high incorporating activity.

When "increase" in the expression level (the intensity of the first signal 6) of the first reporter protein 5 is described, it encompasses, for example, an increase as compared to the value of the expression level (the intensity of the first signal 6) of the first reporter protein 5 before the first enhancer sequence E1 was incorporated into the first vector 1. The value of the expression level (the intensity of the first signal 6) of the first reporter protein 5 before the incorporation of the first enhancer sequence E1 may be 0, for example, depending on the type of promoter, or may be a smaller value than that after the incorporation of the first enhancer sequence E1. The value thereof before the incorporation of the first enhancer sequence E1 can be obtained, for example, by introducing the first vector 1 into a cell in advance, and performing detection before introducing the second vector 3 and/or the transposase TP. Alternatively, it may be a value obtained by the detection immediately after the first vector 1 and the second vector 3 (the transposase TP as necessary) are introduced, that is, before the cutting and the incorporation by the transposase TP are carried out. Alternatively, the intensity of the first signal 6 may be measured in advance in a cell into which first vector 1 is introduced and which does not contain the second vector 3 and/or the transposase TP, and the value may be used for comparison.

The threshold value may be, for example, a value of the expression level (the intensity of the first signal 6) of the first reporter protein 5, or the amount of an increase in the value, obtained when the measuring method of the embodiment is performed using a transposase TP that is known to have an incorporating activity.

In one embodiment, based on the expression level (the intensity of the first signal 6) of the first reporter protein 5, the degree of the incorporating activity of the transposase TP may be evaluated. The degree of incorporating activity is a ratio of transposases TP having an incorporating activity among the total transposases TP to be examined, or an amount of transposases TP having incorporating activity that are expressed or present in cells. For example, it is also possible to evaluate that the higher the expression level (the intensity of the first signal 6) of the first reporter protein 5, the greater the ratio or amount of the transposases TP having an incorporating activity.

Conversely, for example, when the first reporter protein 5 is poorly expressed, it can be evaluated that at least either the cutting activity or the incorporating activity of the transposases TP is poor.

Here, when "the first reporter protein 5 is poorly expressed" is described, it encompasses a case where the first reporter protein 5 (the first signal 6) is not detected or is less than the threshold value, or alternatively, a case where the expression level (the intensity of the first signal 6) of the first reporter protein 5 is not increased, a case where the amount of an increase is less than the threshold value, or a case where the amount of an increase is decreased.

When "having a poor activity" is described, it encompasses having no activity, and having a low activity.

As described above, the activity of the transposase TP can be evaluated by the first evaluation step S3. It is possible to at least find transposases TP with an incorporating activity.

The transposase activity measuring method may be performed using one device. The device includes, for example: a sample storage unit that stores cells; a liquid delivery unit that adds a composition containing the first vector 1 and the second vector 3, optionally the transposase TP, a first substance and/or a second substance used in the first detection step S2, and the like to the cells stored in the sample storage unit; a detection unit that detects the first signal 6 from the cells; an information processing unit including a program for calculating the presence or absence or the degree of the incorporating activity of the transposase TP from the information on the presence or absence or the intensity of the first signal 6 transmitted from the detection unit; and an output unit that outputs a result of calculation performed by the information processing unit.

According to the present method, it is not necessary, for example, to extract a nucleic acid and/or a reporter protein, thereby enabling to rapidly measure the activity of a transposase TP by a simple operation. In addition, it is possible to measure the activity of a transposase TP in a living cell without performing a step that may destroy a cell or denature or decompose a protein in a cell, such as extraction of a nucleic acid and/or a reporter protein. Therefore, the transposase TP and the cell whose activity is measured can also be used in an intact state for further steps.

The present method is performed, for example, on transposases whose activity is unknown regarding the presence or absence, or the degree thereof. For example, it may be used for measuring the activity of, for example, a self-synthesized transposase, a newly discovered or developed transposase, an existing transposase, or a transposase in DNA or RNA form or the like when the transposase is introduced into cells and/or expressed in cells, etc. For example, the present method can also be used for measurement of the activity of a commercially obtained transposase; measurement of the activity of a transposase in a particular process; measurement of the activity of a transposase in a novel process; or quality control of a product containing a transposase. Alternatively, when an introduction step using a transposase is performed as a part of a series of steps such as an experiment, it can also be used when it is desired to confirm whether or not these steps have been appropriately performed in order to proceed to the next step.

However, the application is not limited to these.

Cell separation method

According to a further embodiment, a cell separation method using the first vector 1 is provided. The cell separation method is a method for separating cells based on the activity of transposase.

Figure 4:
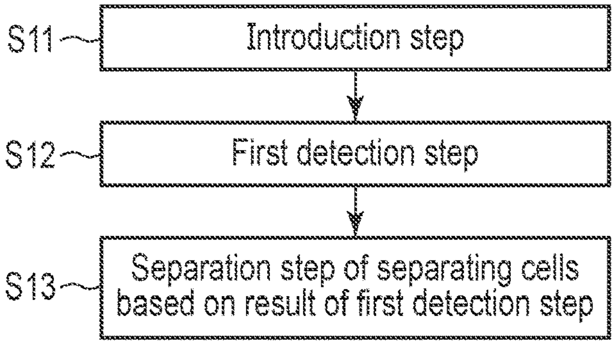
FIG. 4 is a flowchart showing an example of a cell separation method of a first embodiment.

As shown in FIG. 4, the cell separation method includes, for example, the following steps:

(S11) an introduction step of introducing the first vector and the second vector into a cell;

(S12) a first detection step of detecting the first reporter protein expressed from the first reporter gene; and (S13) a separation step of separating the cells based on the result of detection of the first reporter protein.

The introduction step S11 and the first detection step S12 can be performed similarly to the introduction step S1 and the first detection step S2 of the transposase activity measuring method.

The first reporter gene R1 of the first vector 1 used in the cell separation method is preferably a gene that has low cytotoxicity and whose reporter protein can be detected in living cells.

In the separation step S13, for example, cells in which the first reporter protein 5 is highly expressed in the first detection step S12 are regarded as cells containing the transposase TP having at least good incorporating activity, and are separated from other cells. Alternatively, it is also preferable to evaluate the degree of an incorporating activity from the detection result so as to separate cells having particularly high incorporating activity.

The separation may be performed by any known means. For example, a flow cytometry technique such as a cell sorter can be used. Alternatively, desired cells may be manually separated while the cells are observed under a microscope. In that case, a fine probe or the like capable of sucking and discharging cells can be used.

As a result of the separation step S13, cells containing the transposase TP having at least a good incorporating activity can be accurately and easily separated. In addition, since cells can be separated in a living state, the separated cells can be used in further steps such as analysis.

particle 7. Alternatively, as shown in part (b) of FIG. 5, the first vector 1 and the second vector 3 are separately contained in the lipid particles 7.

The material of the lipid membrane constituting the lipid particle 7 contains, for example, a phospholipid or a sphingolipid, such as diacylphosphatidylcholine, diacylphosphatidylethanolamine, ceramide, sphingomyelin, dihydrosphingomyelin, kephalin, or cerebroside, or a combination thereof. In particular, it is preferable to contain 1,2-dioleoyl-3-trimethvlammonium propane (DOTAP) and/or 1,2-dioleoyl-sn-glycero-3-phosphoethanolamine (DOPE), which adjusts the acid dissociation constant of the lipid particles 7.

Further, the material of the lipid particle 7 may contain: a biodegradable lipid (for example, compounds of Formula (1-01), Formula (1-02) and/or Formula (2-01) shown below, and the like); a lipid (for example, polyethylene glycol (PEG) dimyristoyl glycerol (DMG-PEG) or the like) which prevent the aggregation of the lipid particles 7; a component (for example, cholesterol or the like) that prevents leakage of an encapsulated substance from the lipid particles 7; a component for controlling the particle size of the lipid particles 7; a component for facilitating the fusion of the lipid particles 7 with the cells; and/or a component that facilitates the introduction of the encapsulated substance into the cells, or the like.

(I)

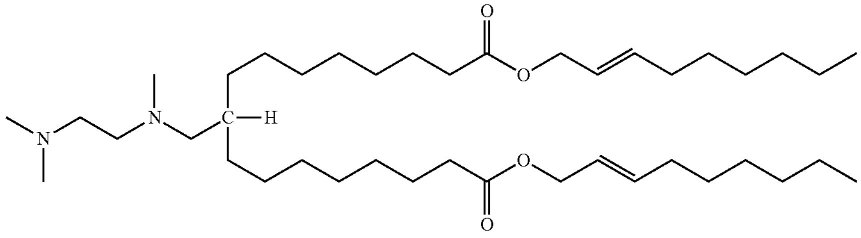

(II)

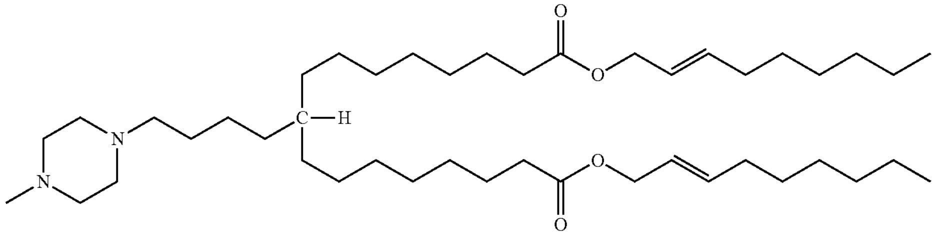

Kits

According to a further embodiment, there is also provided a kit that can be used in the transposase activity measuring method and the cell separation method. The kit includes at least a vector set including the first vector 1 and the second vector 3.

The vector set is provided, for example, as a composition contained in a solvent. As the solvent, for example, endotoxin-free water, PBS, TE buffer, or HEPES buffer can be used. The composition may further contain an excipient, a stabilizer, a diluent, and/or an auxiliary.

Figure 5:
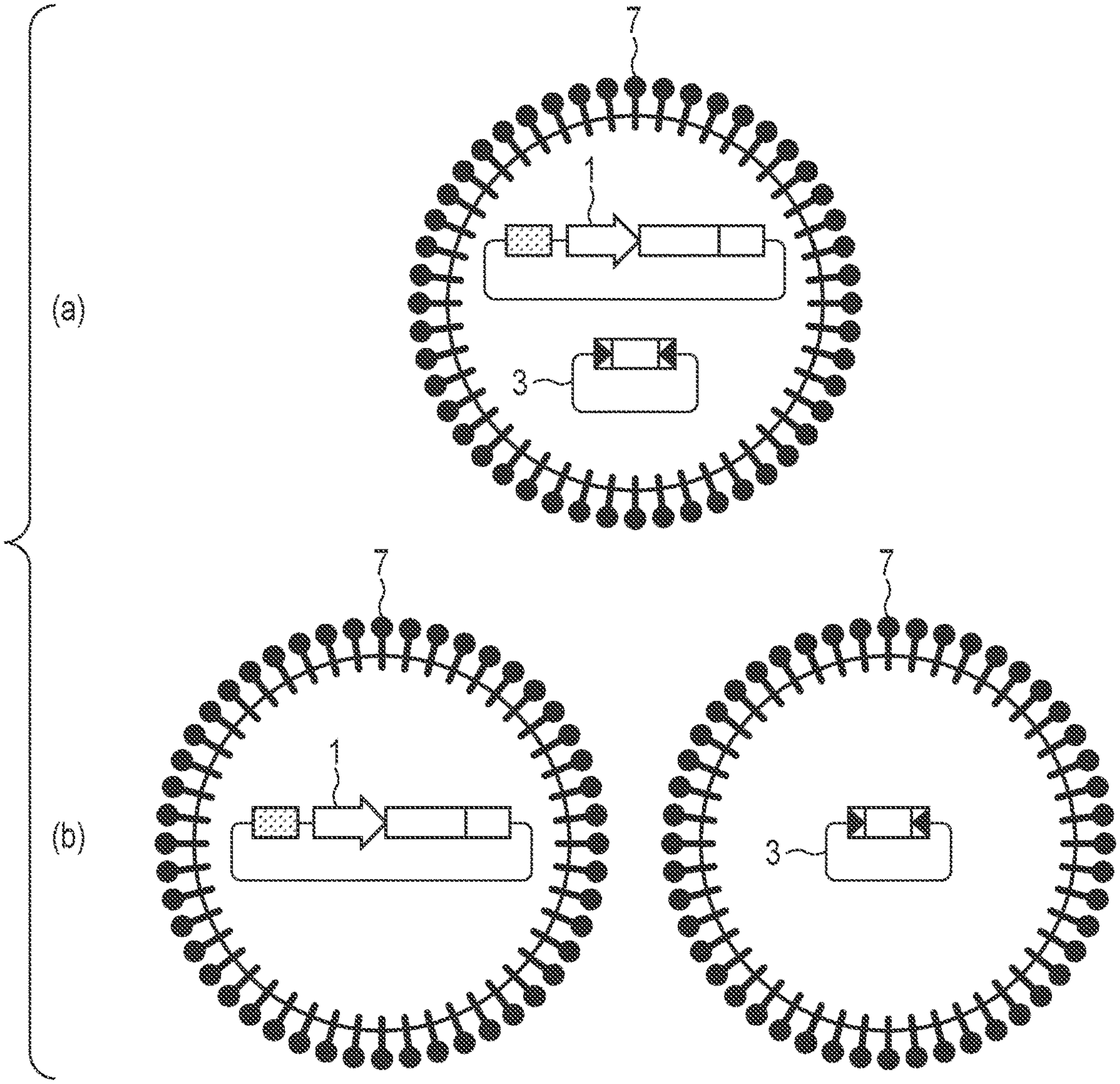
FIG. 5 shows cross-sectional views showing exemplary lipid particles of a first embodiment.

The vector set may be included in the kit in a state of being contained in lipid particles. The lipid particle will be described with reference to FIG. 5. As shown in FIG. 5, the lipid particle 7 is a hollow spherical lipid membrane. For example, as shown in part (a) of FIG. 5, the first vector 1 and the second vector 3 are contained together in the lipid particle 7. Alternatively, as shown in part (b) of FIG. 5, the first vector 1 and the second vector 3 are separately contained in the lipid particles 7.

The lipid particle 7 may be a monomolecular membrane, a double membrane, a triple membrane, or the like. In addition, the lipid particle 7 may be formed of a single-layer membrane, or may be formed of a multi-layer membrane.

The lipid particle 7 may contain additional components as necessary, in addition to the first vector 1 and the second vector 3. The additional component is, for example, a pH adjusting agent and/or an osmotic pressure adjusting agent. The pH adjusting agent is, for example, organic acids such as citric acid and salts thereof, etc. The osmotic pressure adjusting agent is a sugar, an amino acid, or the like.

The lipid particle 7 can be produced using a known method used when a small molecule is enclosed in the lipid particle 7, for example, Bangam's method, an organic solvent extraction method, a surfactant removal method, a freeze-thaw method, or the like. For example, a lipid mixture of the material of the lipid particles 7 contained in an organic solvent such as alcohol at a desired ratio, and an aqueous buffer containing a component to be incorporated, such as a vector are prepared, and the aqueous buffer is added to the lipid mixture. The obtained mixture is stirred and suspended to form lipid particles 7 containing the vector and the like.

The kit may further contain a reagent for detecting the first reporter protein 5. The reagent is, for example, the first substance and/or the second substance described in the description of the first detection step S2.

The vector set and the reagent are provided in a container, individually or in combination of any components.

In a first embodiment described above, when the first reporter protein 5 (the first signal 6) is highly expressed, it can also mean that the sequence for being cut 4 has been normally cut out of the second vector 3. Thus, when the transposase TP is at least evaluated to have a good incorporating activity, it is also possible to expect that the transposase TP also has a cutting activity. In the description of a second embodiment below, a method for more accurately measuring the cutting activity simultaneously with the incorporating activity will be described.

Second Embodiment

Second Vector as Vector for Measuring Transposase Cutting Activity

In a second embodiment, a second vector further has a configuration capable of measuring the cutting activity of a transposase. As shown in part (a) of FIG. 6, a second vector 8 according to a second embodiment includes: a second promoter sequence P2; a second reporter gene 5'-side fragment R2a and a second reporter gene 3'-side fragment R2b ligated to downstream of the second promoter sequence P2; a sequence for being cut 4 arranged between the second reporter gene 5'-side fragment R2a and the second reporter gene 3'-side fragment R2b; and a second transcription termination sequence T2 ligated to downstream of the second reporter gene 3'-side fragment R2b. The second vector 8 can be used in combination with a first vector 1, as in the first embodiment.

Each sequence will be described below.

The second promoter sequence P2 is provided so that, with its activity, the transcription of the gene ligated to downstream can be started. As the second promoter sequence P2, any promoter sequence listed in the description of the first promoter sequence P1 can be used. The second promoter sequence P2 may be the same as or different sequence from the first promoter sequence P1.

The second reporter gene 5'-side fragment R2a and the second reporter gene 3'-side fragment R2b each include a 5'-side sequence and a 3'-side sequence obtained by bisecting a base sequence encoding one reporter gene (the second reporter gene R2, not shown).

The second reporter gene R2, as being bisected, is in a state in which its reporter activity is inactivated. The lengths of the base sequences of the second reporter gene 5'-side fragment R2a and the second reporter gene 3'-side fragment R2b, that is, the divisional positions, are not limited as long as they are selected so that the activity of the second reporter gene R2 is inactivated, and the lengths of the two sequences may be the same as or different from each other.

As the second reporter gene R2, any of the reporter genes listed in the description of the first reporter gene R1 can be used. The second reporter gene R2 is preferably selected as being different from the first reporter gene R1. For example, the first reporter gene R1 and the second reporter gene R2 may be luciferase genes having substrates with different luminescent colors, respectively, fluorescent protein genes having different fluorescent colors, or the like.

Examples of the base sequences of the second reporter gene 5'-side fragment R2a and the second reporter gene 3'-side fragment R2b when the second reporter gene R2 is a firefly luciferase gene (Table 4) are shown in the following Tables 12 and 13, respectively.

TABLE 12

| Split luciferase gene 5' region (second reporter gene 5'-side fragment R2a, SEC ID NO: 12) | |
|---|---|
| atggaagacg ccaaaaacat aaagaaaggc ccgccgccat tctatccgct ggaagatgga | 60 |
| accgctggag agcaactgca taaggctatg aagagatacg ccctggttcc tggaacaatt | 120 |
| gcttttacag atgcacatat cgaggtggac atcacttacg ctgagtactt cgaaatgtcc | 180 |
| gttcggttgg cagaagctat gaaacgatat gggctgaata caaatcacag aatcgtcgta | 240 |
| tgcagtgaaa actctcttca attctttatg ccggtgttgg gcgcgttatt tatcggagtt | 300 |
| gcagttgcgc ccgcgaacga catttataat gaacgtgaat tgctcaacag tatgggcatt | 360 |
| tcgcagccta ccgtggtgtt cgtttccaaa aaggggttgc aaaaaatttt gaacgtgcaa | 420 |
| aaaaagctcc caatcatcca aaaaattatt atcstggatt ctaaaacgga ttaccaggga | 480 |
| tttcagtcga tgtacacgtt cgtcacatct catctacctc ccggtt | 526 |

TABLE 13

| Split luciferase gene 3' region (second reporter gene 3'-side fragment R2b, SEQ ID NO: 13) | |
|---|---|
| tgaatacgat tttgtgccag agtccttcga taggcacaag acaattgcac tgatcatgaa | 60 |
| ctcctctgga tctactggtc tgcctaaagg tgtcgctctg cctcatagaa ctgcctgcgt | 120 |
| gagattctcg catgccagag atcctatttt tggcaatcaa atcattccgg atactgcgat | 180 |

TABLE 13-continued

| Split luciferase gene 3' region (second reporter gene 3'-side fragment R2b, SEQ ID NO: 13) | |
|---|---|
| tttaagtgtt gttccattcc atcacggttt tggaatgttt actacactcg gatatttgat | 240 |
| atgtggattt cgagtcgtct taatgtatag atttcaagaa gacctgtttc tgaggagcct | 300 |
| tcaggattac aagattcaaa gtgcgctgct ggtgccaacc ctattctcct tcttcgccaa | 360 |
| aagcactctg attgacaaat acgatttatc taatttacac gaaattgctt ctggtggcgc | 420 |
| tcccctctct aaggaagtcg gggaagcggt tgccaagagg ttccatctgc caggtatcag | 480 |
| gcaaggatat gggctcactg agactacatc agctattctg attacacccg agggggatga | 540 |
| taaaccgggc gcggtcggta aagttgttcc attttttgaa gcgaaggttg tggatctgga | 600 |
| taccgggaaa acgctgggcg ttaatcaaag aggcgaactg tgtgtgagag gtcctatgat | 660 |
| tatgtccggt tatgtaaaca atccggaagc gaccaacgcc ttgattgaca aggatggatg | 720 |
| gctacattct ggagacatag cttactggga cgaacacgaa cacttcttca tcgttgaccg | 780 |
| cctgaagtct ctgattaagt acaaaggcta tcaggtggct cccgctgaat tggaatccat | 840 |
| cttgctccaa caccccaaca tcttcgacgc aggtgtcgca ggtcttcccg acgatgacgc | 900 |
| cggtgaactt cccgccgccg ttgttgtttt ggagcacgga aagacgatga cggaaaaaga | 960 |
| gatcgtggat tacgtcgcca gtcaagtaac aaccgcgaaa aagttgcgcg gaggagttgt | 1020 |
| gtttgtggac gaagtaccga aaggtcttac cggaaaactc gacgcaagaa aaatcagaga | 1080 |
| gatcctcata aaggccaaga agggcggaaa gatcgccgtg taa | 1123 |

The sequence for being cut 4 is the same as that of the first embodiment described above, and includes a 5'-side transposase recognition sequence 4a, a 3'-side transposase recognition sequence 4b, and a first enhancer sequence E1 arranged between these two recognition sequences.

The second reporter gene R2 sequence formed by cutting out the sequence for being cut 4 and ligating the second reporter gene 5'-side fragment R2a and the second reporter gene 3'-side fragment R2b may include a sequence other than the sequence derived from the reporter gene as long as the function as a reporter is not lost. The other sequence is, for example, a sequence consisting of nucleotides that are a multiple of 3 in number, and is preferably a sequence encoding 0 to 20 amino acids. For example, a trace sequence remaining after the cutting may be present between the second reporter gene 5'-side fragment R2a and the second reporter gene 3'-side fragment R2b. Trace sequences may, but need not, encode amino acids.

The second transcription termination sequence T2 is operably ligated to downstream of the second reporter gene 3'-side fragment R2b so as to terminate the transcription of the second reporter gene R2. As the second transcription termination sequence T2, any of the transcription termination sequences listed in the description of the first transcription termination sequence T1 can be used. The second transcription termination sequence T2 may be the same sequence as or a different sequence from the first transcription termination sequence T1.

The second vector 8 may contain any other base sequence similarly to the second vector 3 of the first embodiment. Such a base sequence is, for example, a base sequence such as a reporter gene expression unit having a specific function, a drug resistance gene, a replication initiation protein expression unit, and/or a replication initiation sequence, or alternatively, a sequence having no function.

Figure 6:
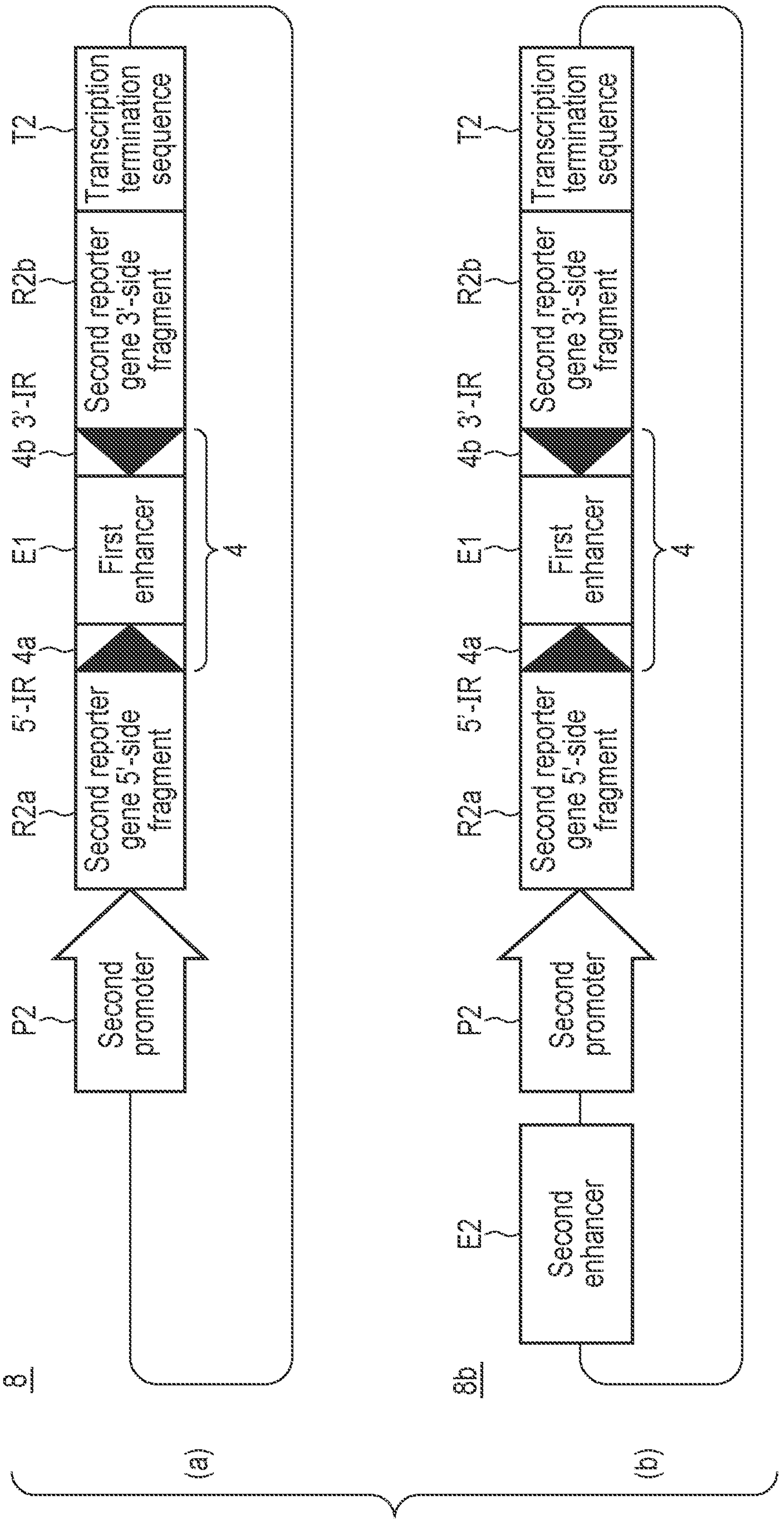
FIG. 6 shows examples of a second vector of a second embodiment.

In a further embodiment, as shown in part (b) of FIG. 6, the second vector 8b may further include a second enhancer sequence E2. The second enhancer sequence E2 is operably ligated to upstream of the second promoter sequence P2 so as to be capable of promoting the activation of the second promoter sequence P2 and promoting the expression of a gene ligated to downstream thereof. As the second enhancer sequence E2, any enhancer listed in the description of the first enhancer sequence E1 can be used. The second enhancer sequence E2 can be selected, for example, according to the type of the second promoter sequence P2. The second enhancer sequence E2 may be the same sequence as or a different sequence from the first enhancer sequence E1.

For example, when the second promoter sequence P2 enables the expression of a gene ligated to downstream by an enhancer, it is preferable to use the second enhancer sequence E2. However, when the second promoter sequence P2 is of a type that allows expression of a gene ligated to downstream thereof without an enhancer, it is not necessary to provide the second enhancer sequence E2.

Transposase activity measuring method

According to second embodiment, there is provided a method for measuring the activity of a transposase in a cell by using a vector set including the first vector 1 described in the first embodiment and the second vector 8.

Figure 7:
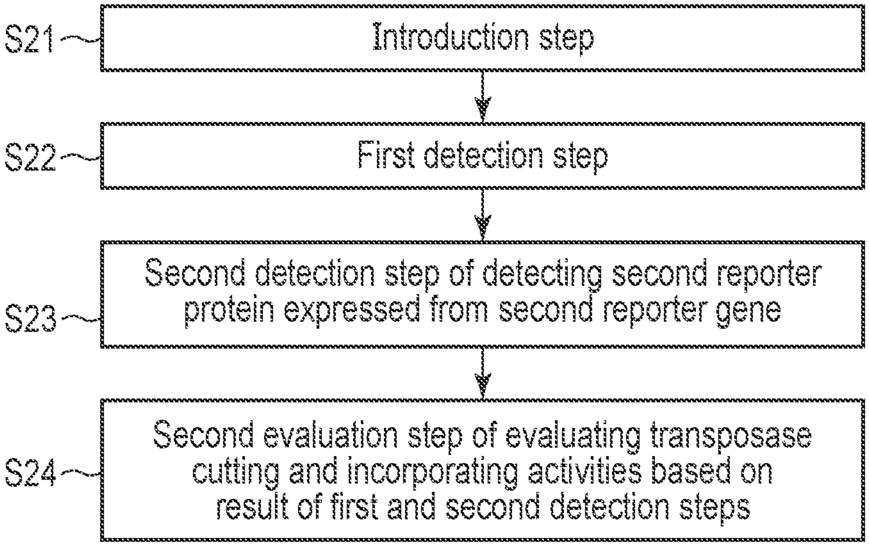
FIG. 7 is a flowchart showing an example of a transposase activity measuring method of a second embodiment.

The transposase activity measuring method includes, for example, the following steps shown in FIG. 7:

(S21) an introduction step of introducing the first vector and the second vector into a cell;

(S22) a first detection step of detecting the first reporter protein expressed from the first reporter gene;

(S23) a second detection step of detecting the second reporter protein expressed from the second reporter gene; and (S24) a second evaluation step of evaluating the activity of the transposase from the result of detection of the first reporter protein and the result of detection of the second reporter protein.

The introduction step S21 can be performed similarly to the introduction step S1 of the first embodiment except that the second vector 8 is used instead of the second vector 3.

The behavior of each vector after the introduction step S21 will be described with reference to FIG. 8. First, the sequence for being cut 4 is cut out of the second vector 8 by the active transposase TP (part (a) of FIG. 8). Next, the sequence for being cut 4 is incorporated into the transposase target sequence 2 of the first vector 1 (part (b) of FIG. 8). That is, the sequence for being cut 4 is transferred.

Figure 8:
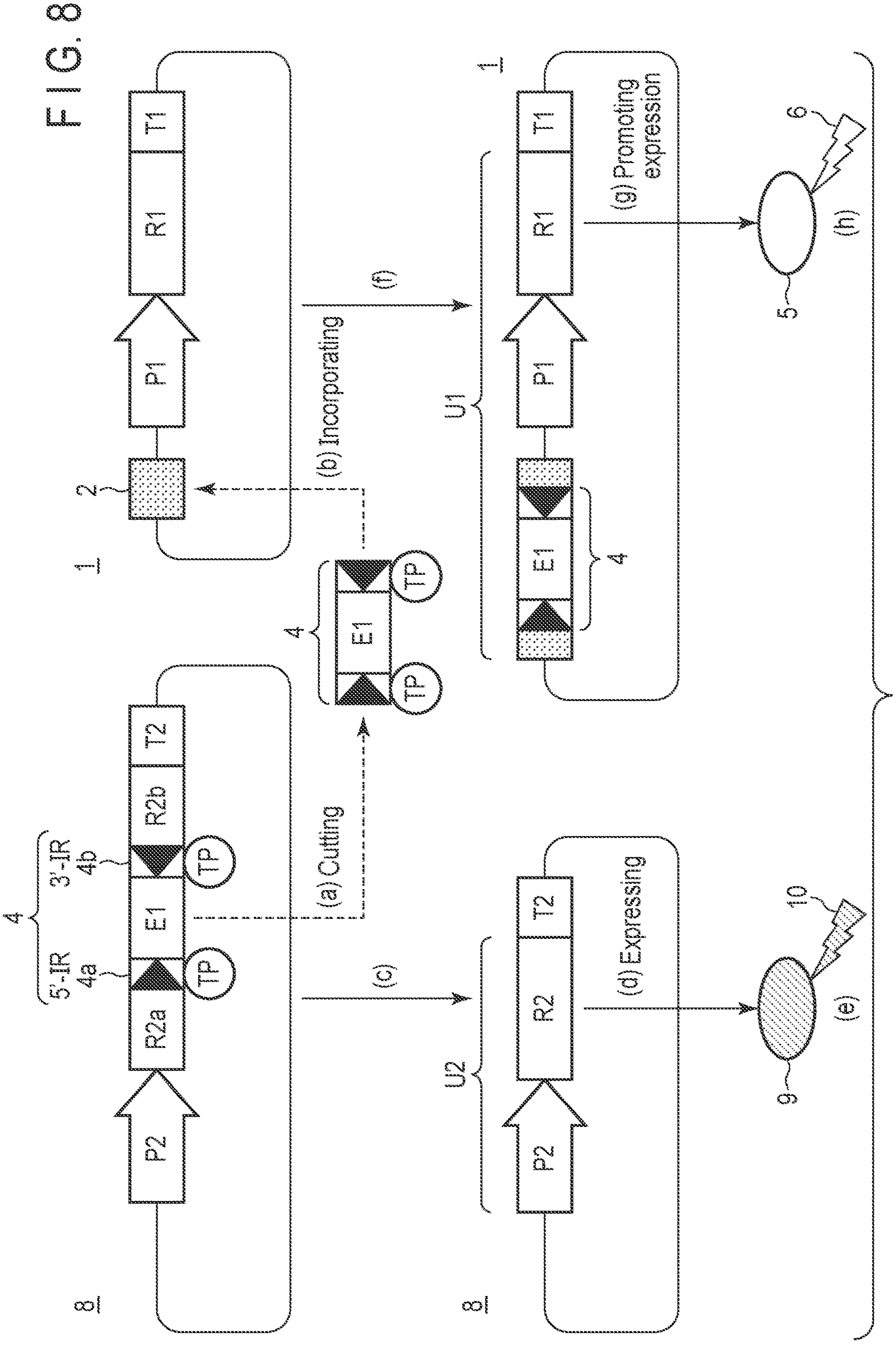
FIG. 8 is a diagram showing an example of the behavior of each vector after the introduction step of a second embodiment.

Thereafter, in the second vector 8, the second reporter gene 5'-side fragment R2a and the second reporter gene 3'-side fragment R2b are ligated to form the second reporter gene R2 (part (c) of FIG. 8). As a result, a second gene expression unit U2 including the second promoter sequence P2, the second reporter gene R2, and as necessary the second enhancer sequence E2 is formed in the second vector 8. Thereby, a second reporter protein 9 is expressed from the second reporter gene R2 (part (d) of FIG. 8). The second reporter protein 9 generates a second signal 10 (part (e) of FIG. 8).

On the other hand, in the first vector 1, as in a first embodiment, the first enhancer sequence E1 is incorporated to form the first gene expression unit U1 (part (f) of FIG. 8), and the expression of the first reporter gene R1 is promoted (part (g) of FIG. 8). Thereby, the expression level of the first reporter protein 5 increases. The first reporter protein 5 generates a first signal 6 (part (h) of FIG. 8).

Thus, when the transposase TP has both a cutting activity and an incorporating activity, the transfer of the first enhancer sequence E1 contained in the sequence for being cut 4 from the second vector 8 to the first vector 1 causes the second signal 10 and the first signal 6 to be obtained from the second vector 8 and the first vector 1, respectively.

On the other hand, when the cutting activity of the transposase TP is poor, the sequence for being cut 4 is not cut out, and the second reporter gene R2 remains inactivated. As a result, the second reporter protein 9 is poorly expressed. In this case, since the sequence for being cut 4 is not cut out, the first reporter protein 5 can be poorly expressed regardless of whether the incorporating activity of the transposase TP is good or not.

In addition, in the case of a transposase TP having a good cutting activity and a poor incorporating activity, the second reporter protein 9 is highly expressed, but the first reporter protein 5 can be poorly expressed.

Next, a first detection step S22 is performed. The first detection step S22 can be performed similarly to the first detection step S2 of the first embodiment.

Next, the second reporter protein 9 is detected (the second detection step S23). The detection of the second reporter protein 9 can be performed, for example, by detecting the second signal 10. The detection may be performed by using the method described in the first detection step S2, which is selected according to the type of the second reporter protein 9.

Either the first detection step S22 or the second detection step S23 may be performed earlier, or the both may be performed simultaneously. When the both steps are performed simultaneously, it is preferable to select the first promoter sequence P1 and the second promoter sequence P2 (if necessary, the first enhancer sequence E1 and the second enhancer sequence E2) so that the expression level of the second reporter gene R2 is higher than the expression level of the first reporter gene R1. This is to prevent the second signal 10 from being buried in the first signal 6 and being difficult to detect.

Next, the cutting activity and incorporating activity of the transposase are evaluated from the results of the first detection step S22 and the second detection step S23 (the second evaluation step S24).

The incorporating activity can be determined, for example, from the expression of the first reporter protein 5 (the first signal 6) as the method described in the first evaluation step S3.

On the other hand, when the second reporter protein 9 is highly expressed (the intensity of the second signal 10 is high), it can be determined that the cutting activity of the transposase TP is good.

Meanwhile, when the expression level of the second reporter protein 9 (the intensity of the second signal 10) is low, it indicates that normal cutting has not been performed, so that it can be determined that the cutting activity is poor.

From the above, when the expression level of the first reporter protein 5 is high and the incorporating activity is good, and at the same time, when the expression level of the second reporter protein 9 is high, it can be determined that the cutting activity of the transposase TP is also good. When both the activities are good as described above, the transposase TP to be analyzed has a high efficiency of incorporating a nucleic acid into a genome, and can be suitable for use in applications such as genome editing.

When the expression level of the first reporter protein 5 is low and the incorporating activity is poor, it can be determined that the cutting activity is good if the expression level of the second reporter protein 9 is high. Conversely, if the expression level of the second reporter protein 9 is low, it can be determined that the cutting activity is also poor.

As described above, by using the second vector 8, it is possible to simultaneously evaluate the cutting activity and the incorporating activity of the transposase TP in the same cell. According to the present method, the incorporating activity is measured by using a sequence cut out in the measurement of the cutting activity. This is in line with the working mechanism of transposase in gene incorporation.

Therefore, according to the present method, it is possible to measure the activity of a transposase more accurately than separately measuring the cutting activity and the incorporating activity.

Cell separation method

Figure 9:
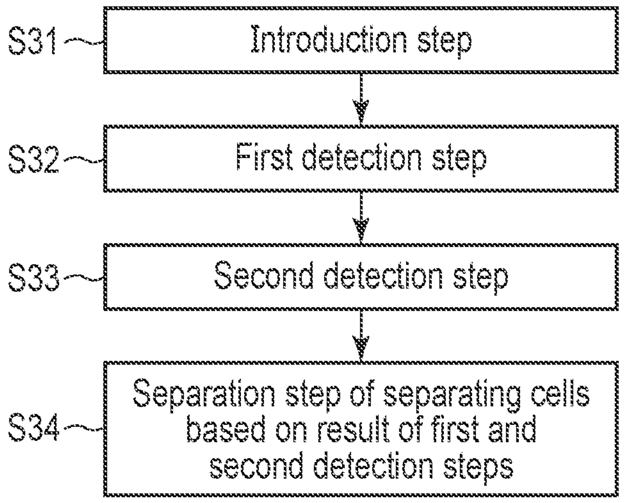
FIG. 9 is a flowchart showing an example of the cell separation method of a second embodiment.

The first vector 1 and the second vector 8 of second embodiment can also be used in a cell separation method. The cell separation method includes the following steps, for example, as shown in FIG. 9:

(S31) an introduction step of introducing the first vector 1 and the second vector into a cell;

(S32) a first detection step of detecting the first reporter protein expressed from the first reporter gene;

(S32) a second detection step of detecting the second reporter protein expressed from the second reporter gene; and (S34) a separation step of separating cells based on a result of detection of the first reporter protein and a result of detection of the second reporter protein.

The introduction step S31, the first detection step S32, and the second detection step S33 can be performed similarly to the introduction step S21, the first detection step S22, and the second detection step S23 of the transposase activity measuring method.

In the separation step S34, desired cells are separated on the basis of, for example, the expression level of the first reporter protein 5 and/or the expression level of the second reporter protein 9. In particular, cells in which both the first reporter protein 5 and the second reporter protein 9 are highly expressed are preferably separated from other cells. As a result, cells containing a transposase TP having a good cutting activity and an incorporating activity are obtained. Alternatively, it is also preferable to evaluate the degree of each activity from the detection result to separate cells having particularly high activities in both of the activities.

According to this method, a cell containing a transposase TP having good activities in both respects is easily obtained. Therefore, for example, the efficiency of the genome-edited cell production using this cell can be improved.

The first vector 1 and the second vector 8 of second embodiment can also be provided as a kit similar to that of the first embodiment. Such a kit may further contain a reagent for detecting the second reporter protein 9 expressed from the second reporter gene R2.

Third Embodiment

In the first embodiment and the second embodiment, an example has been shown in which the first enhancer sequence E1 is transferred from the sequence for being cut 4 of the second vectors 3 and 8 to the first vector 1 by the transposase TP. However, the sequence to be transferred is not limited to the first enhancer sequence E1. For example, if the expression level (the intensity of the first signal 6) of the first reporter protein 5 changes before and after the transfer, the activity of the transposase TP can be evaluated regardless of which sequence is transferred. In a third embodiment, an example in which a sequence to be transferred is selected from sequences other than the first enhancer sequence E1 in the vector set of the first embodiment will be described.

The sequence to be transferred is a sequence involved in expression of a first reporter gene R1, the sequence being selected from the base sequences of the first vector 1 described in the first embodiment. The sequence involved in the expression of the first reporter gene R1 is selected, for example, from among the sequences included in a first gene expression unit U1, and is, for example, an entire sequence of a first enhancer sequence E1, a first promoter sequence P1, or the first reporter gene R1, or a partial sequence thereof.

The sequence involved in the expression of the first reporter gene R1 is preferably a base sequence having a length of about 50 to about 9000 bases, and more preferably a base sequence having a length of about 50 to about 2000 bases.

A first vector 1 according to third embodiment includes a sequence in which a sequence selected as involved in the expression of the first reporter gene R1 (for example, any one of or a part of E1, P1, and R1 constituting the first gene expression unit U1) is substituted with a transposase target sequence 2. In other words, it has a configuration in which the transposase target sequence 2 is arranged instead of the sequence involved in the expression of the first reporter gene R1. In addition, a second vector 3 according to third embodiment has a configuration in which a sequence selected as a sequence involved in the expression of the first reporter gene R1 (for example, any one of or a part of E1, the first promoter sequence P1, and the first reporter gene R1 constituting the first gene expression unit U1) is arranged between a 5'-side transposase recognition sequence 4a and a 3'-side transposase recognition sequence 4b of the sequence for being cut 4.

Figure 10:
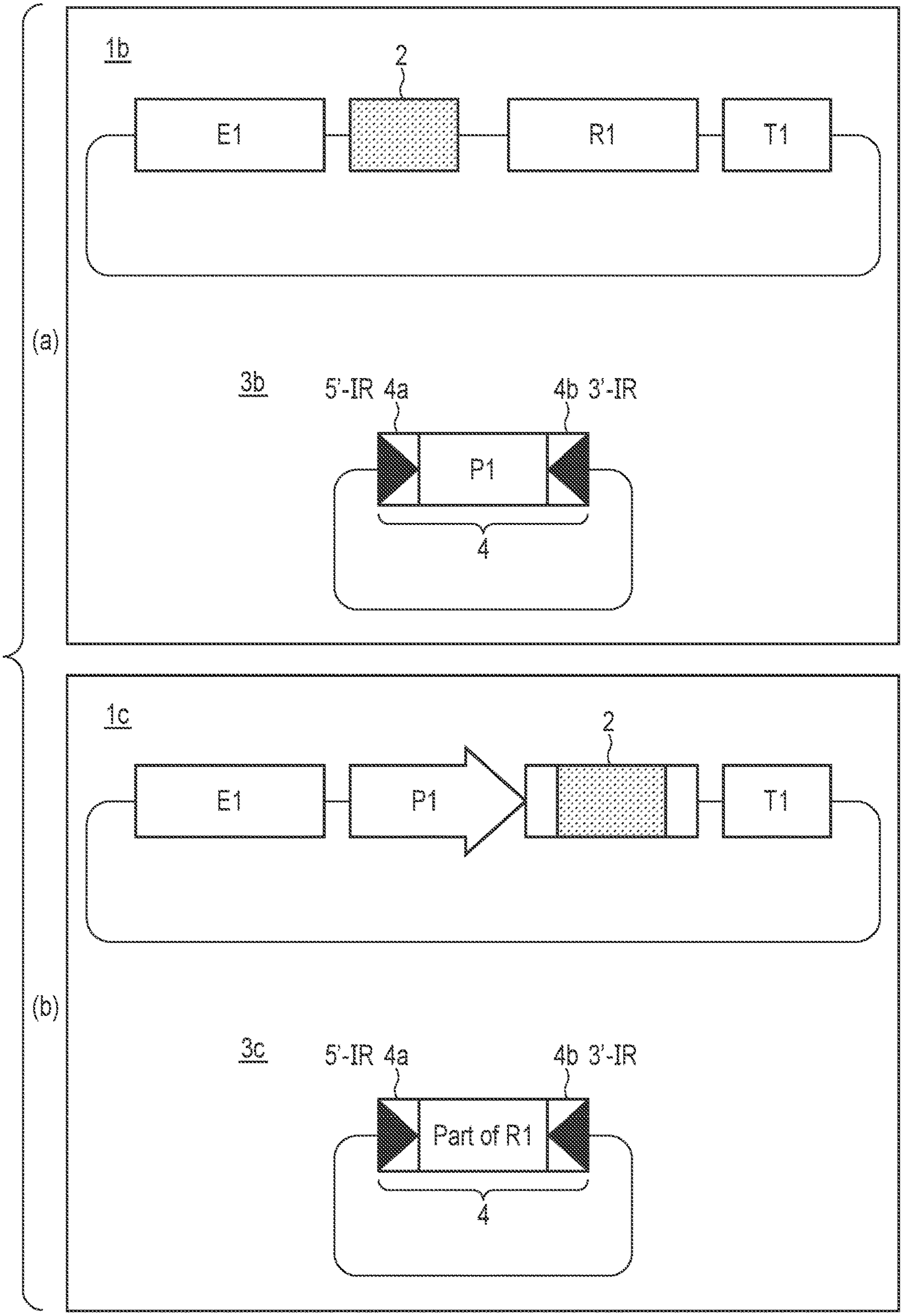
FIG. 10 is a diagram showing examples of a first vector and a second vector of a third embodiment.

FIG. 10 illustrates an example of the vector set according to third embodiment. Part (a) of FIG. 10 shows an example in which the sequence selected as the sequence involved in the expression of the first reporter gene R1 is the first promoter sequence P1. In this case, a first vector 1b includes the transposase target sequence 2 in a region where the first promoter sequence P1 is to be arranged in the first gene expression unit U1 formed after the transfer. A second vector 3b includes a first promoter sequence P1 between the 5'-side transposase recognition sequence 4a and the 3'-side transposase recognition sequence 4b of the sequence for being cut 4.

Part (b) of FIG. 10 shows an example in which the sequence selected as the sequence involved in the expression of the first reporter gene R1 is a partial sequence of the first reporter gene R1. In this case, a first vector 1c includes the transposase target sequence 2 in a part of the region where the first reporter gene R1 is to be arranged in the first gene expression unit U1 formed after the transfer. The second vector 3c includes a part of the first reporter gene R1 between the 5'-side transposase recognition sequence 4a and the 3'-side transposase recognition sequence 4b of the sequence for being cut 4.

The second vector according to third embodiment may have the same configuration as that of the second vector 8 according to the second embodiment. Such a second vector includes, for example, a sequence selected as a sequence involved in expression of the first reporter gene R1 in place of the first enhancer sequence E1 of the second vector 8 or 8b shown in part (a) of FIG. 6 or part (b) of FIG. 6.

An example in which a sequence other than the first enhancer sequence E1 is selected as the sequence to be transferred is described above, but the sequence to be transferred is preferably the first enhancer sequence E1. For example, when the first promoter sequence P1 or the first reporter gene R1 is selected, the first reporter protein 5 is basically not expressed from the first vector 1 before the transfer. However, when the first enhancer sequence E1 is used, the first reporter protein 5 can be expressed even before transfer, and detecting that makes it possible to confirm the introduction of the first vector 1 into cells before analysis. Therefore, the first embodiment and the second embodiment using the first enhancer sequence E1 may be more preferable than a third embodiment.

The vector set of a third embodiment can be used in a kit, a transposase activity measuring method, and a cell separation method similar to those of the first embodiment and the second embodiment.

Hereinafter, examples in which vector sets of the embodiments are produced and used will be described.

Example 1

Production of Vector for Measuring Transposase Cutting Activity

First, an artificial DNA (SEQ ID NO: 14) shown in Table 14, in which a multi-cloning sequence was arranged between 5'-IR (SEQ ID NO: 8) and 3'-IR (SEQ ID NO: 9), which are recognition sequences of piggyBac, was synthesized (available from BEX Co., Ltd.).

TABLE 14

| Artificial DNA (SEQ ID NO: 14) | |
|---|---|
| ccctagaaag atagtctgcg taaaattgac gcatgcattc ttgaaatatt gctctctctt | 60 |
| tctaaatagc gcgaatccgt cgctgtgcat ttacgacatc tcagtcgccg cttgcagctc | 120 |
| ccgtgaggcg tgcttgtcaa tgcggtaagt gtcactgatt ttgaactata acgaccgcgt | 180 |
| gagtcaaaat gacgcatgat tatcttttac gtgactttta agatttaact catacgataa | 240 |
| ttatattgtt atttcatgct ctacttacgt gataacttat tatatatata ttttcttgtt | 300 |
| atagatatct ggcctaactg gccggtacct gagctcgcta gcctcgagga tatcaagatc | 360 |
| tggcctcggc ggccaagctt ggcttttgtt actttataga agaaattttg agtttttgtt | 420 |
| tttttttaat aaataaataa acataaataa attgtttgtt gaatttatta ttagtatgta | 480 |
| agtgtaaata taataaaact taatatctat tcaaattaat aaataaacct cgatatacag | 540 |
| accgataaaa cacatgcgtc aattttacgc atgattatct ttaacgtacg tcacaatatg | 600 |
| attatctttc taggg | 615 |

Next, a vector (pCMV-Luc) in which a firefly luciferase expression unit including a cytomegalovirus (CMV) promoter sequence (SEQ ID NO: 2), a firefly luciferase gene derived from firefly (SEQ ID NO: 4), and a bovine growth hormone transcription termination sequence (SEQ ID NO: 6) was incorporated was prepared, and the artificial DNA (SEQ ID NO: 14) was incorporated therein such that the firefly luciferase gene was divided into two regions. The firefly luciferase gene was divided into a 5'-side region (SEQ ID NO: 12) and a 3'-side region (SEQ ID NO: 13). Thereby, a vector shown in Table 15 below: pCMV-LuIRuC (SEQ ID NO: 15) was obtained.

TABLE 15-1

| pCMV-LuIRuC (SEQ ID NO: 15) | |
|---|---|
| gacggatcgg gagatctccc gatcccctat ggtgcactct cagtacaatc tgctctgatc | 60 |
| ccgcatagtt aagccagtat ctgctccctg cttgtgtgtt ggaggtcgct aagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgccaata atgacgtatg ttcccatagt aacgccaata gggactttcc | 420 |
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| gtttaaactt aagcttggca ttccggtact gttggtaaag ccaccatgga agacgccaaa | 960 |
| aacataaaga aaggcccggc gccattctat ccgctggaag atggaaccgc tggagagcaa | 1020 |
| ctgcataagg ctatgaagag atacgccctg gttcctggaa caattgcttt tacagatgca | 1080 |
| catatcgagg tggacatcac ttacgctgag tacttcgaaa tgtccgttcg gttggcagaa | 1140 |
| gctatgaaac gatatgggct gaatacaaat cacagaatcg tcgtatgcag tgaaaactct | 1200 |
| cttcaattct ttatgccggt gttgggcgcg ttatttatcg gagttgcagt tgcgcccgcc | 1260 |

TABLE 15-1-continued

| pCMV-LuIRuC (SEQ ID NO: 15) |
|---|
| aacgacattt ataatgaacg tgaattgctc aacactatgg gcatttcgca gcctaccgtg 1320 |
| gtgttcgttt ccaaaaaggg gttgcaaaaa attttgaacg tgcaaaaaaa gctcccaatc 1380 |
| atccaaaaaa ttattatcat ggattctaaa acggattacc agggatttca gtcgatgtac 1440 |
| acgttcgtca catctcatct acctcccggt tttaacccta gaaagatagt ctgcgtaaaa 1500 |
| ttgacgcatg cattcttgaa atattgctct ctctttctaa atagcgcgaa tccgtcgctg 1560 |
| tgcatttagg acatctcagt cgccgcttgg agctcccgtg aggcgtgctt gtcaatgcgc 1620 |
| taagtgtcac tgattttgaa ctataacgac cgcgtgagtc aaaatgacgc atgattatct 1680 |
| tttacgtgac ttttaagatt taactcatac gataattata ttgttatttc atgttctact 1740 |
| tacgtgataa cttattatat atatattttc ttgttataga tatctggcct aactggccgg 1800 |
| tacctgagct cgctagcctc gaggatatca agatctggcc tcggcggcca agcttggctt 1860 |
| ttgttacttt atagaagaaa ttttgagttt ttgttttttt ttaataaata aataaacata 1920 |
| aataaattgt ttgttgaatt tattattagt atgtaagtgt aaatataata aaacttaata 1980 |
| tctattcaaa ttaataaata aacctcgata tacagaccga taaaacacat gcgtcaattt 2040 |
| tacgcatgat tatctttaac gtacgtcaca atatgattat ctttctaggg aatttgaata 2100 |
| cgattttgtg ccagagtcct tcgataggga caagacaatt gcactgatca tgaactcctc 2160 |
| tggatctact ggtctgccta aaggtgtcgc tctgcctcat agaactgcct gcgtgagatt 2220 |
| ctcgcatgcc agagatccta tttttggcaa tcaaatcatt ccggatactg cgattttaag 2280 |
| tgttgttcca ttccatcacg gttttggaat gtttactaca ctcggatatt tgatatgtgg 2340 |
| atttcgagtc gtcttaatgt atagatttga agaagagctg tttctgagga gccttcagga 2400 |
| ttacaagatt caaagtgcgc tgctggtgcc aaccctattc tccttcttcg ccaaaagcac 2460 |
| tctgattgac aaatacgatt tatctaattt acaccaaatt gcttctggtg gcgctcccct 2520 |
| ctctaaggaa gtcggggaag cggttgccaa gaggttccat ctgccaggta tcaggcaagg 2580 |
| atatgggctc actgagacta catcagctat tctgattaca cccgaggggg atgataaacc 2640 |
| gggcgcggtc ggtaaagttg ttccattttt tgaagcgaag gttgtggatc tggataccgc 2700 |
| gaaaacgctg ggcgttaatc aaagaggcga actgtgtgtg agaggtccta tgattatgtc 2760 |
| cggttatgta aacaatccgg aagcgaccaa cgccttgatt gacaaggatg gatggctaca 2820 |
| ttctggagac atagcttact gggacgaaga cgaacacttc ttcatcgttg accgcctgaa 2880 |
| gtctctgatt aagtacaaag gctatcaggt ggctcccgct gaattggaat ccatcttgct 2940 |
| ccaacacccc aacatcttcg acgcaggtgt cgcaggtctt cccgacgatg acgccggtga 3000 |
| acttcccgcc gccgttgttg ttttggagca cggaaagacg atgacggaaa aagagatcgt 3060 |
| ggattacgtc gccagtcaag taacaaccgc gaaaaagttg cgcggaggag ttgtgtttgt 3120 |
| ggacgaagta ccgaaaggtc ttaccggaaa actcgacgca agaaaaatca gagagatcct 3180 |
| cataaaggcc aagaagggcg gaaagatcgc cgtgtaattc tagagggccc gcggttcgaa 3240 |
| ggtaagccta tccctaaccc tctcctcggt ctcgattcta cgcgtaccgg tcatcatcac 3300 |
| catcaccatt gagtttaaac ccgctgatca gcctcgactg tgccttctag ttgccagcca 3360 |
| tctgttgttt gcccctcccc cctgccttcc ttgaccctgg aaggtgccac tcccactgtc 3420 |
| ctttcctaat aaaatgagga aattgcatcg cattgtctga gtaggtgtca ttctattctc 3480 |
| gggggtgggg tggggcagga cagcaagggg gaggattggg aagacaatag caggcatgct 3540 |
| ggggatgcgg tgggctctat ggcttctgag gcggaaagaa ccagctgggg ctctaggggg 3600 |

TABLE 15-1-continued

| pCMV-LuIRuC (SEQ ID NO: 15) | |
|---|---|
| tatccccacg cgccctgtag cggcgcatta agcgcggcgg gtgtggtggt tacgcgcagc | 3660 |
| gtgaccgcta cacttgccag cgccctagcg cccgctcctt tcgctttctt cccttccttt | 3720 |
| ctcgccacgt tcgccggctt tccccgtcaa gctctaaatc gggggctccc tttagggttc | 3780 |
| cgatttagtg ctttacggca cctcgacccc aaaaaacttg attagggtga tggttcacgt | 3840 |
| agtgggccat cgccctgata gacggttttt cgccctttga cgttggagtc cacgttcttt | 3900 |
| aatagtggac tcttgttcca aactggaaca acactcaacc ctatctcggt ctattctttt | 3960 |
| gatttataag ggattttgcc gatttcggcc tattggttaa aaaatgagct gatttaacaa | 4020 |
| aaatttaacg cgaattaatt ctgtggaatg tgtgtcagtt agggtgtgga aagtccccag | 4080 |
| gctccccagc aggcagaagt atgcaaagca tgcatctcaa ttagtcagca accaggtgtg | 4140 |
| gaaagtcccc aggctcccca gcaggcagaa gtatgcaaag catgcatctc aattagtcag | 4200 |
| caaccatagt cccgccccta actccgccca tcccgcccct aactccgccc agttccgccc | 4260 |
| attctccgcc ccatggctga ctaatttttt ttatttatgc agaggccgag gccgcctctg | 4320 |
| cctctgagct attccagaag tagtgaggag gcttttttgg aggcctaggc ttttgcaaaa | 4380 |
| agctcccggg agcttgtata tccattttcg gatctgatca gcacgtgcta cgagatttcg | 4440 |
| attccaccgc cgccttctat gaaaggttgg gcttcggaat cgttttccgg gacgccggct | 4500 |
| ggatgaccct ccagcgcggg gatctcatgc tggagttctt cgcccacccc aacttgttta | 4560 |
| ttgcagctta taatggttac aaataaagca atagcatcac aaatttcaca aataaagcat | 4620 |
| ttttttcact gcattctagt tgtggtttgt ccaaactcat caatgtatct tatcatgtct | 4680 |
| gtataccgtc gacctctagc tagagcttgg cgtaatcatg gtcatagctg tttcctgtgt | 4740 |
| gaaattgtta tccgctcaca attccacaca acatacgagc cggaagcata aagtgtaaag | 4800 |
| cctggggtgc ctaatgagtg agctaactca cattaattgc gttgcgctca ctgcccgctt | 4860 |
| tccagtcggg aaacctgtcg tgccagctgc attaatgaat cggccaacgc gcggggagag | 4920 |
| gcggtttgcg tattgggcgc tcttccgctt cctcgctcac tgactcgctg cgctcggtcg | 4980 |
| ttcggctgcg gcgagcggta tcagctcact caaaggcggt aatacggtta tccacagaat | 5040 |
| caggggataa cgcaggaaag aacatgtgag caaaaggcca gcaaaaggcc aggaaccgta | 5100 |
| aaaaggccgc gttgctggcg tttttccata ggctccgccc ccctgacgag catcacaaaa | 5160 |
| atcgacgctc aagtcagagg tggcgaaacc cgacaggact ataaagatac caggcgtttc | 5220 |
| cccctggaag ctccctcgtg cgctctcctg ttccgaccct gccgcttacc ggatacctgt | 5280 |
| ccgcctttct cccttcggga agcgtggcgc tttctcatag ctcacgctgt aggtatctca | 5340 |
| gttcggtgta ggtcgttcgc tccaagctgg gctgtgtgca cgaacccccc gttcagcccg | 5400 |
| accgctgcgc cttatccggt aactatcgtc ttgagtccaa cccggtaaga cacgacttat | 5460 |
| cgccactggc agcagccact ggtaacagga ttagcagagc gaggtatgta ggcggtgcta | 5520 |
| cagagttctt gaagtggtgg cctaactacg gctacactag aagaacagta tttggtatct | 5580 |
| gcgctctgct gaagccagtt accttcggaa aaagagttgg tagctcttga tccggcaaac | 5640 |
| aaaccaccgc tggtagcggt ggtttttttg tttgcaagca gcagattacg cgcagaaaaa | 5700 |
| aaggatctca agaagatcct ttgatctttt ctacggggtc tgacgctcag tggaacgaaa | 5760 |
| actcacgtta agggattttg gtcatgagat tatcaaaaag gatcttcacc tagatccttt | 5820 |
| taaattaaaa atgaagtttt aaatcaatct aaagtatata tgagtaaact tggtctgaca | 5880 |
| gttaccaatg cttaatcagt gaggcaccta tctcagcgat ctgtctattt cgttcatcca | 5940 |

TABLE 15-1-continued

| pCMV-LuIRuC (SEQ ID NO: 15) | |
|---|---|
| tagttgcctg actccccgtc gtgtagataa ctacgatacg ggagggctta ccatctggcc | 6000 |
| ccagtgctgc aatgataccg cgagacccac gctcaccggc tccagattta tcagcaataa | 6060 |
| accagccagc cggaagggcc gagcgcagaa gtggtcctgc aactttatcc gcctccatcc | 6120 |
| agtctattaa ttgttgccgg gaagctagag taagtagttc gccagttaat agtttgcgca | 6180 |
| acgttgttgc cattgctaca ggcatcgtgg tgtcacgctc gtcgtttggt atggcttcat | 6240 |
| tcagctccgg ttcccaacga tcaaggcgag ttacatgatc ccccatgttg tgcaaaaaac | 6300 |
| cggttagctc cttcggtcct ccgatcgttg tcagaagtaa gttggccgca gtgttatcac | 6360 |
| tcatggttat ggcagcactg cataattctc ttactgtcat gccatccgta agatgctttt | 6420 |
| ctgtgactgg tgagtactca accaagtcat tctgagaata gtgtatgcgg cgaccgagtt | 6480 |
| gctcttgccc ggcgtcaata cgggataata ccgcgccaca tagcagaact ttaaaagtgc | 6540 |
| tcatcattgg aaaacgttct tcggggcgaa aactctcaag gatcttaccg ctgttgagat | 6600 |
| ccagttcgat gtaacccact cctgcaccca actgatcttc agcatctttt actttcacca | 6660 |
| gcgtttctgg gtgagcaaaa acaggaaggc aaaatgccgc aaaaaaggga ataagggcga | 6720 |
| cacggaaatg ttgaatactc atactcttcc tttttcaata ttattgaagc atttatcagg | 6780 |
| gttattgtct catgagcgga tacatatttg aatgtattta gaaaaataaa caaatagggg | 6840 |
| ttccgcgcac atttccccga aaagtgccac ctgacgtc | 6878 |

Figure 11:
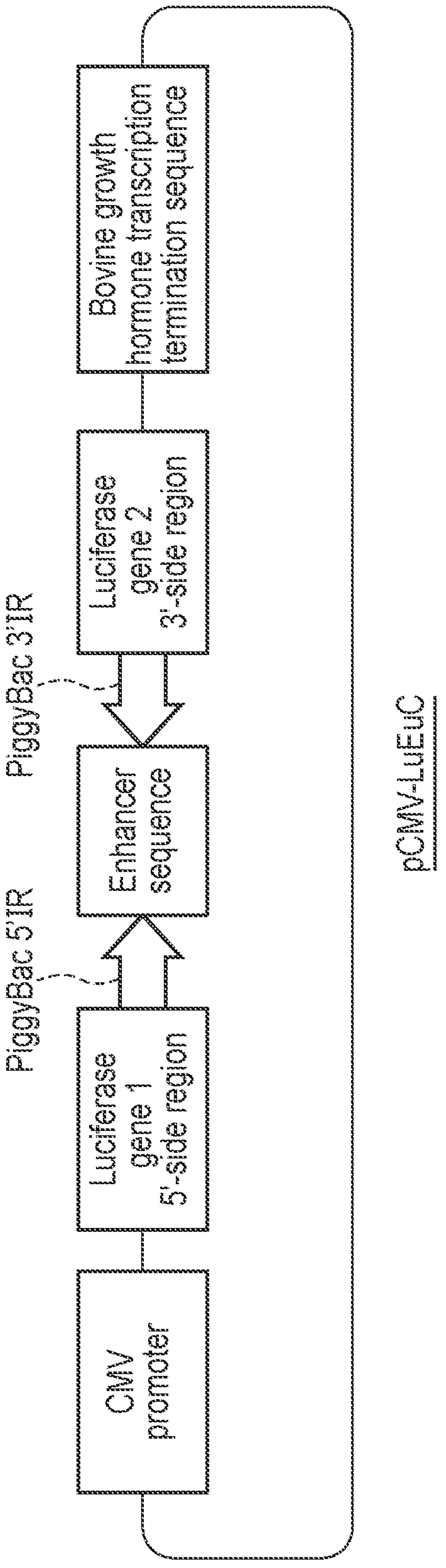
FIG. 11 shows a configuration of pCMV-LuEuC prepared in Example 1.

Next, an enhancer sequence (SEQ ID NO: 11) was incorporated into the multi-cloning sequence of the artificial DNA inserted into pCMV-LuIRuC. This enhancer sequence has a function of increasing the transcription level of a luciferase gene of a vector for transposase incorporating activity described in Example 2. As a result, a vector for measuring transposase cutting activity: pCMV-LuEuC (Table 16, SEQ ID NO: 16) shown in FIG. 11 was obtained.

TABLE 16

| pCMV-LuEuC (SEQ ID NO: 16) | |
|---|---|
| gacggatcgg gagatctccc gatcccctat ggtgcactct cagtacaatc tgctctgatg | 60 |
| ccgcatagtt aagccagtat ctgctccctg cttgtgtgtt ggaggtcgct gagtagtgcc | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata cggactttcc | 420 |
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcc | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| gtttaaactt aagcttggca ttccggtact gttggtaaag ccaccatgga agacgccaaa | 960 |
| aacataaaga aaggcccggc gccattctat ccgctggaag atggaaccgc tggagagcaa | 1020 |

TABLE 16-continued

| pCMV-LuEuC (SEQ ID NO: 16) |
|---|
| ctgcataagg ctatgaagag atacgccctg gttcctggaa caattgcttt tacagatgca 1080 |
| catatcgagg tggacatcac ttacgctgag tacttcgaaa tgtccgttcg gttggcagaa 1140 |
| gctatgaaac gatatgggct gaatacaaat cacagaatcg tcgtatgcag tgaaaactct 1200 |
| cttcaattct ttatgccggt gttgggcgcg ttatttatcg gagttgcagt tgcgcccgcc 1260 |
| aacgacattt ataatgaacg tgaattgctc aacagtatgg gcatttcgca gcctaccgtg 1320 |
| gtgttcgttt ccaaaaaggg gttgcaaaaa attttgaacg tgcaaaaaaa gctcccaatc 1380 |
| atccaaaaaa ttattatcat gcattctaaa acggattacc agggatttca gtcgatgtac 1440 |
| acgttcgtca catctcatct acctcccggt tttaacccta gaaagatagt ctgcgtaaaa 1500 |
| ttgacgcatg cattcttgaa atattgctct ctctttctaa atagcgcgaa tccgtcgctg 1560 |
| tgcatttagg acatctcagt cgccgcttgg agctcccgtg aggcgtgctt gtcaatgcgg 1620 |
| taagtgtcac tgattttgaa ctataacgac cgcgtgagtc aaaatgacgc atgattatct 1680 |
| tttacgtgac ttttaagatt taactcatac gataattata ttgttatttc atgttctact 1740 |
| tacgtgataa cttattatat atatattttc ttgttataga tatctggcct aactggccgg 1800 |
| taccgcgtta cataacttac gctaaatggc ccgcctggct gaccgcccaa cgacccccgc 1860 |
| ccattgacgt caataatgac gtatgttccc atagtaacgc caatagggac tttccattga 1920 |
| cgtcaatggg tggagtattt acggtaaact gcccacttgg cagtacatca agtgtatcat 1980 |
| atgccaagta cgccccctat tgacgtcaat gacggtaaat ggcccgcctg gcattatgcc 2040 |
| cagtacatga ccttatggga ctttcctact tggcagtaca tctacgtatt agtcatcgct 2100 |
| attaccatgg tctcgaggat atcaagatct ggcctcggcg gccaagcttg gcttttgtta 2160 |
| ctttatagaa gaaattttga gtttttgttt ttttttaata aataaataaa cataaataaa 2220 |
| ttgtttgttg aatttattat tagtatgtaa gtgtaaatat aataaaactt aatatctatt 2280 |
| caaattaata aataaacctc gatatacaga ccgataaaac acatgcgtca attttacgca 2340 |
| tgattatctt taacgtacgt cacaatatga ttatctttct agggttaatg aatacgattt 2400 |
| tgtgccagag tccttcgata gcgacaagac aattgcactg atcatgaact cctctggatc 2460 |
| tactggtctg cctaaaggtg tcgctctgcc tcatagaact gcctgcgtga gattctcgca 2520 |
| tgccagagat cctatttttg gcaatcaaat cattccggat actgcgattt taagtgttgt 2580 |
| tccattccat cacggttttg gaatgtttac tacactcgga tatttgatat gtggatttcg 2640 |
| agtcgtctta atgtatagat ttgaagaaga gctgtttctg aggagccttc aggattacaa 2700 |
| gattcaaagt gcgctgctgg tgccaaccct attctccttc ttcgccaaaa gcactctgat 2760 |
| tgacaaatac gatttatcta atttacacga aattgcttct ggtggcgctc ccctctctaa 2820 |
| ggaagtcggg gaagcggttg ccaagaggtt ccatctgcca ggtatcaggc aaggatatgg 2880 |
| gctcactgag actacatcag ctattctgat tacacccgag gggatgata aaccgggcgc 2940 |
| ggtcggtaaa gttgttccat tttttgaagc gaaggttgtg gatctggata ccgggaaaac 3000 |
| gctgggcgtt aatcaaagag gcgaactgtg tgtgagaggt cctatgatta tgtccggtta 3060 |
| tgtaaacaat ccggaagcga ccaacgcctt gattgacaag gatggatggc tacattctgg 3120 |
| agacatagct tactgggacg aagacgaaca cttcttcatc gttgaccgcc tgaagtctct 3180 |
| gattaagtac aaaggctatc aggtggctcc cgctgaattg gaatccatct tgctccaaca 3240 |
| ccccaacatc ttcgacgcag gtgtcgcagg tcttcccgac gatgacgccg gtgaacttcc 3300 |
| cgccgccgtt gttgttttgg agcacggaaa gacgacgacg gaaaaagaga tcgtggatta 3360 |

TABLE 16-continued

| pCMV-LuEuC (SEQ ID NO: 16) | |
|---|---|
| cgtcgccagt caagtaacaa ccgcgaaaaa gttgcgcgga ggagttgtgt ttgtggacga | 3420 |
| agtaccgaaa ggtcttaccg gaaaactcga cgcaagaaaa atcagagaga tcctcataaa | 3480 |
| ggccaagaag ggcggaaaga tcgccgtgta attctagagg gcccgcggtt cgaaggtaag | 3540 |
| cctatcccta accctctcct ccgtctcgat tctacgcgta ccggtcatca tcaccatcac | 3600 |
| cattgagttt aaacccgctg atcagcctcg actgtgcctt ctagttgcca gccatctgtt | 3660 |
| gtttgcccct cccccgtgcc ttccttgacc ctggaaggtg ccactcccac tgtcctttcc | 3720 |
| taataaaatg aggaaattgc atcgcattgt ctgagtaggt gtcattctat tctggggggt | 3780 |
| ggggtggggc aggacagcaa gggggaggat tgggaagaca atagcaggca tgctggggat | 3840 |
| gcggtgggct ctatggcttc tgaggcggaa agaaccagct ggggctctag ggggtatccc | 3900 |
| cacgcgccct gtagcggcgc attaagcgcg gcgggtgtgg tggttacgcg cagcgtgacc | 3960 |
| gctacacttg ccagcgccct agcgcccgct cctttcgctt tcttcccttc ctttctcgcc | 4020 |
| acgttcgccg gctttccccg tcaagctcta aatcgggggc tccctttagg gttccgattt | 4080 |
| agtgctttac ggcacctcga ccccaaaaaa cttgactagg gtgatggttc acgtagtggc | 4140 |
| ccatcgccct gatagacggt ttttcgccct ttgacgttgg agtccacgtt ctttaatagt | 4200 |
| ggactcttgt tccaaactgg aacaacactc aaccctatct cggtctattc ttttgattta | 4260 |
| taagggattt tgccgatttc ggcctattgg ttaaaaaatg agctgattta acaaaaattt | 4320 |
| aacgcgaatt aattctgtgg aatgtgtgtc agttagggtg tggaaagtcc ccaggctccc | 4380 |
| cagcaggcag aagtatgcaa agcatgcatc tcaattagtc agcaaccagg tgtggaaagt | 4440 |
| ccccaggctc cccagcaggc acaagtatgc aaagcatgca tctcaattag tcagcaacca | 4500 |
| tagtcccgcc cctaactccg cccatcccgc ccctaactcc gcccagttcc gcccattctc | 4560 |
| cgccccatgg ctgactaatt ttttttattt atgcagaggc cgaggccgcc tctgcctctc | 4620 |
| agctattcca gaagtagtga gcaggctttt ttggaggcct aggcttttgc aaaaagctcc | 4680 |
| cgggagcttg tatatccatt ttcggatctg atcaccacgt gctacgagat ttcgattcca | 4740 |
| ccgccgcctt ctatgaaagg ttgggcttcg gaatcgtttt ccgggacgcc ggctggatga | 4800 |
| tcctccagcg cggggatctc atgctggagt tcttcgccca ccccaacttg tttattgcag | 4860 |
| cttataatgg ttacaaataa agcaatagca tcacaaattt cacaaataaa gcattttttt | 4920 |
| cactgcattc tagttgtggt ttgtccaaac tcatcaatgt atcttatcat gtctgtatac | 4980 |
| cgtcgacctc tagctagagc ttggcgtaat catggtcata gctgtttcct gtgtgaaatt | 5040 |
| gttatccgct cacaattcca cacaacatac gagccggaag cataaagtgt aaagcctggg | 5100 |
| gtgcctaatg agtgagctaa ctcacattaa ttgcgttgcg ctcactgccc gctttccagt | 5160 |
| cgggaaacct gtcgtgccag ctgcattaat gaatcggcca acgcgcgggg agaggcggtt | 5220 |
| tgcgtattgg gcgctcttcc gcttcctcgc tcactgactc gctgcgctcg gtcgttcggc | 5280 |
| tgcggcgagc ggtatcagct cactcaaagg cggtaatacg gttatccaca gaatcagggg | 5340 |
| ataacgcagg aaagaacatg tgagcaaaag gccagcaaaa ggccaggaac cgtaaaaagg | 5400 |
| ccgcgttgct ggcgtttttc cataggctcc gcccccctga cgagcatcac aaaaatcgac | 5460 |
| gctcaagtca gaggtggcga aacccgacag gactataaag ataccaggcg tttccccctg | 5520 |
| gaagctccct cgtgcgctct cctgttccga ccctgccgct taccggatac ctgtccgcct | 5580 |
| ttctcccttc gggaagcgtg gcgctttctc atagctcacg ctgtaggtat ctcagttcgg | 5640 |
| tgtaggtcgt tcgctccaag ctgggctgtg tgcacgaacc ccccgttcag cccgaccgct | 5700 |

TABLE 16-continued

| pCMV-LuEuC (SEQ ID NO: 16) | |
|---|---|
| gcgccttatc cggtaactat cgtcttgagt ccaacccggt aagacacgac ttatcgccac | 5760 |
| tggcagcagc cactggtaac aggattagca gagcgaggta tgtaggcggt gctacagagt | 5820 |
| tcttgaagtg gtggcctaac tacggctaca ctagaagaac agtatttggt atctgcgctc | 5880 |
| tgctgaagcc agttaccttc ggaaaaagag ttggtagctc ttgatccggc aaacaaacca | 5940 |
| ccgctggtag cggtggtttt tttgtttgca agcagcagat tacgcgcaga aaaaaaggat | 6000 |
| ctcaagaaga tcctttgatc ttttctacgg ggtctgacgc tcagtggaac gaaaactcac | 6060 |
| gttaagggat tttggtcatg agattatcaa aaaggatctt cacctagatc cttttaaatt | 6120 |
| aaaaatgaag ttttaaatca atctaaagta tatatgagta aacttggtct gacagttacc | 6180 |
| aatgcttaat cagtgaggca cctatctcag cgatctgtct atttcgttca tccatagttg | 6240 |
| cctgactccc cgtcgtgtag ataactacga tacgggaggg cttaccatct ggccccagtc | 6300 |
| ctgcaatgat accgcgagac ccacgctcac cggctccaga tttatcagca ataaaccagc | 6360 |
| cagccggaag ggccgagcgc agaagtggtc ctgcaacttt atccgcctcc atccagtcta | 6420 |
| ttaattgttg ccgggaagct agagtaagta gttcgccagt taatagtttg cgcaacgttg | 6480 |
| ttgccattgc tacaggcatc gtggtgtcac gctcgtcgtt tggtatggct tcattcagct | 6540 |
| ccggttccca acgatcaagg cgagttacat gatcccccat gttgtgcaaa aaagcggtta | 6600 |
| gctccttcgg tcctccgatc gttgtcagaa gtaagttggc cgcagtgtta tcactcatgg | 6660 |
| ttatggcagc actgcataat tctcttactg tcatgccatc cgtaagatgc ttttctgtga | 6720 |
| ctggtgagta ctcaaccaag tcattctgag aatagtgtat gcggcgaccg agttgctctt | 6780 |
| gcccggcgtc aatacgggat aataccgcgc cacatagcag aactttaaaa gtgctcatca | 6840 |
| ttggaaaacg ttcttcgggg cgaaaactct caaggatctt accgctgttg agatccagtt | 6900 |
| cgatgtaacc cactcgtgca cccaactgat cttcagcatc ttttactttc accagcgttt | 6960 |
| ctgggtgagc aaaaacagga aggcaaaatg ccgcaaaaaa gggaataagg gcgacacgga | 7020 |
| aatgttgaat actcatactc ttcctttttc aatattattg aagcatttat cagggttatt | 7080 |
| gtctcatgag cggatacata tttgaatgta tttagaaaaa taaacaaata ggggttccgc | 7140 |
| gcacatttcc ccgaaaagtg ccacctgacg tc | 7172 |

Example 2

Production of Vector for Measuring Transposase Incorporating Activity

Figure 12:
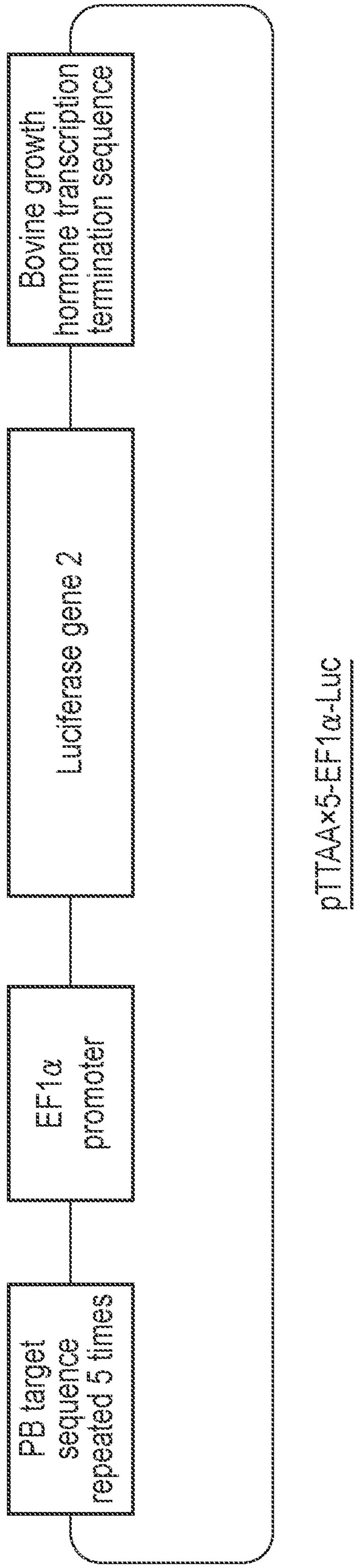
FIG. 12 shows a configuration of pTTAAx5-EF1a-Luc prepared in Example 2.

First, a vector (pEF1α-Luc) into which a luciferase expression unit including a promoter sequence (SEQ ID NO: 3) of a human polypeptide chain elongation factor gene (EF1α), a gene (SEQ ID NO: 5) of luciferase derived from Oplophorus gracilirostris (hereinafter, referred to as "OG luciferase"), and a bovine growth hormone transcription termination sequence (SEQ ID NO: 6) was incorporated was prepared. An artificial DNA (SEQ ID NO: 14) in which TTAA as a target sequence of piggyBac was repeated 5 times was incorporated into an upstream region of an EF1α promoter of pEF1α-Luc. As a result, a vector for measuring transposase incorporating activity: pTTAAx5-EF1α-Luc (Table 17, SEQ ID NO: 17) shown in FIG. 12 was obtained.

TABLE 17

| pTTAAx5-EF1α-Luc (SEQ ID NO: 17) | |
|---|---|
| accaatgctt aatcagtgag gcacctatct cagcgatctg tctatttcgt tcatccatac | 60 |
| ttgcctgact ccccgtcgtg tagataacta cgatacggga gggcttacca tctggcccca | 120 |
| gtgctgcaat gataccgcga gacccacgct caccggctcc agatttatca gcaataaacc | 180 |
| agccagccgg aagggccgag cgcagaagtg gtcctgcaac tttatccgcc tccatccagt | 240 |
| ctattaattg ttgccgggaa gctagagtaa gtagttcgcc agttaatagt ttgcgcaacg | 300 |

TABLE 17-continued

| pTTAAx5-EF1α-Luc (SEQ ID NO: 17) | |
|---|---|
| ttgttgccat tgctacaggc atcgtggtgt cacgctcgtc gtttggtatg gcttcattca | 360 |
| gctccggttc ccaacgatca aggcgagtta catgatcccc catgttgtgc aaaaaagcgg | 420 |
| ttagctcctt cggtcctccg atcgttgtca gaagtaagtt ggccgcagtg ttatcactca | 480 |
| tggttatggc agcactgcat aattctctta ctgtcatgcc atccgtaaga tgcttttctg | 540 |
| tgactggtga gtactcaacc aagtcattct gagaatagtg tatgcggcga ccgagttgct | 600 |
| cttgcccggc gtcaatacgg gataataccg cgccacatag cagaacttta aaagtgctca | 660 |
| tcattggaaa acgttcttcg gggcgaaaac tctcaaggat cttaccgctg ttgagatcca | 720 |
| gttcgatgta acccactcgt gcacccaact gatcttcagc atcttttact ttcaccagcc | 780 |
| tttctgggtg agcaaaaaca ggaaggcaaa atgccgcaaa aaagggaata agggcgacac | 840 |
| ggaaatgttg aatactcata ctcttccttt ttcaatatta ttgaagcatt tatcagggtt | 900 |
| attgtctcat gagcggatac atatttgaat gtattcagaa aaataaacaa ataggggttc | 960 |
| cgcgcacatt tccccgaaaa gtgccacctg acgtcgacgg atcgggagat ctcccgatcc | 1020 |
| cctatggtgc actctcagta caatctgctc tgatgccgca tagttaagcc agtatctgct | 1080 |
| ccctgcttgt gtgttggagg tcgctgagta gtgcgcgagc aaaatttaag ctacaacaac | 1140 |
| gcaaggcttg accgacaatt gcatgaagaa tctgcttagg gttaggcgtt ttgcgctgct | 1200 |
| tcgcgatttc tagacggagt actgtcctcc gaagacgctt aaagacgctt aaagacgctt | 1260 |
| aaagacgctt aaagacgctt aaagacgctc ggaggacagt actccgtctg gtaccagaaa | 1320 |
| cgtgaggctc cggtgcccgt cagtgggcag agcgcacatc gcccacagtc cccgagaagt | 1380 |
| tggggggagg ggtcggcaat tgaaccggtg cctagagaag gtggcgcggg gtaaactggc | 1440 |
| aaagtgatgt cgtgtactgg ctccgccttt ttcccgaggg tgggggagaa ccgtatataa | 1500 |
| gtgcagtagt cgccgtgaac gttctttttc gcaacgggtt tgccgccaga acacaggtaa | 1560 |
| gtgccgtgtg tggttcccgc gggcctggcc tctttacggg ttatggccct tgcgtgcctt | 1620 |
| gaattacttc cacgcccctg gctgcagtac gtgattcttg atcccgagct tcgggttgga | 1680 |
| agtgggtggg agagttcgag gccttgcgct taaggagccc cttcgcctcg tgcttgagtt | 1740 |
| gaggcctggc ttgggcgctg gcgccgccgc gtgcgaatct ggtggcacct tcgcgcctgt | 1800 |
| ctcgctgctt tcgataagtc tctagccatt taaaattttt gatgacctgc tgcgacgctt | 1860 |
| tttttctggc aagatagtct tgtaaatgcg ggccaagatc tgcacactgg tatttcggtt | 1920 |
| tttggggccg cgggcggcga cggggcccgt gcgtcccagc gcacatgttc ggcgaggcgg | 1980 |
| ggcctgcgag cgcggccacc gagaatcgga cgggcgtagt ctcaagctgg ccggcctgct | 2040 |
| ctggtgcctg gcctcgcgcc gccgtgtatc gccccgccct gggcggcaag gctggcccgg | 2100 |
| tcggcaccag ttgcgtgagc ggaaagatgg ccgcttcccg gccctgctgc agggagctca | 2160 |
| aaatggagga cgcggcgctc gcgagagcgg gcgggtgagt cacccacaca aaggaaaagc | 2220 |
| gcctttccgt cctcagccgt cgcttcatgt gactccacgg agtaccgggc gccgtccagg | 2280 |
| cacctcgatt agttctcgag cttttggagt acgtcgtctt taggttgggg ggaggggttt | 2340 |
| tatgcgatgg agtttcccca cactgagtgg gtggagactg aagttaggcc agcttggcac | 2400 |
| ttgatgtaat tctccttgga atttgccctt tttgagtttg gatcttggtt cattctcaag | 2460 |
| cctcagacag tggttcaaag tttttttctt ccatttcagg tgtcgtgaaa gctagcgttt | 2520 |
| aaacttaagc ttggcaatcc ggtactgttg gtaaagccac catggtcttc acactcgaag | 2580 |
| atttcgttgg ggactggcga cagacagccg gctacaacct ggaccaagtc cttgaacagg | 2640 |

TABLE 17-continued pTTAAx5-EF1α-Luc (SEQ ID NO: 17)

```
gaggtgcgtc cagtttgttt cagaatctcg ggtgtccgt aactccgatc caaaggattg    2700
tcctgagcgg tgaaaatggg ctgaagatcg acatccatgt catcatcccg tatgaaggtc    2760
tgagcggcga ccaaatgggc cagatcgaaa aaatttttaa ggtggtgtac cctgtggatg    2820
atcatcactt taaggtgatc ctgcactatg gcacactggt aatcgacggg gttacgccga    2880
acatgatcga ctatttcgga cggccgtatg aaggcatcgc cgtgttcgac ggcaaaaaga    2940
tcactgcaac agggaccctg tcgaacggca acaaaattat cgacgagcgc ctgatcaacc    3000
ccgacggctc cctgctgttc cgagtaacca tcaacggagt gaccggctgg cggctgtgcc    3060
aacgcattct ggcgtaaggc cgcgactcta gagggcccgc ggttcgaagg taagcctatc    3120
cctaaccctc tcctcggtct ccattctacg cgtaccggtc atcatcacca tcaccattga    3180
gtttaaaccc gctgatcagc ctcgactgtg ccttctagtt gccagccatc tgttgtttgc    3240
ccctcccccg tgccttcctt gaccctggaa ggtgccactc ccactgtcct ttcctaataa    3300
aatgaggaaa ttgcatcgca ttgtctgagt aggtgtcatt ctattctggg gggtggggtg    3360
gggcaggaca gcaaggggga ggattgggaa gacaatagca ggcatgctgg ggatgcggtg    3420
ggctctatgg cttctgaggc ggaaagaacc agctggggct ctagggggta tccccacgcg    3480
ccctgtagcg gcgcattaag cgcggcgggt gtggtggtta cgcgcagcgt gaccgctaca    3540
cttgccagcg ccctagcgcc cgctcctttc gctttcttcc cttcctttct cgccacgttc    3600
gccggctttc cccgtcaagc tctaaatcgg gggctccctt tagggttccg atttagtgct    3660
ttacggcacc tcgaccccaa aaaacttgat tagggtgatg gttcacgtag tgggccatcg    3720
ccctgataga cggtttttcg ccctttgacg ttggagtcca cgttctttaa tagtggactc    3780
ttgttccaaa ctggaacaac actcaaccct atctcggtct attcttttga tttataaggg    3840
attttgccga tttcggccta ttggttaaaa aatgagctga tttaacaaaa atttaacgcc    3900
aattaattct gtggaatgtg tgtcagttag ggtgtggaaa gtccccaggc tccccagcag    3960
gcagaagtat gcaaagcatg catctcaatt agtcagcaac caggtgtgga aagtccccag    4020
gctccccagc aggcagaagt atgcaaagca tgcatctcaa ttagtcagca accatagtcc    4080
cgcccctaac tccgcccatc ccgcccctaa ctccgcccag ttccgcccat tctccgcccc    4140
atggctgact aattttttt atttatgcag aggccgaggc cgcctctgcc tctgagctat    4200
tccagaagta gtgaggaggc ttttttggag gcctaggctt ttgcaaaaag ctcccgggag    4260
cttgtatatc cattttcgga tctgatcagc acgtgctacg agatttcgat tccaccgccg    4320
ccttctatga aaggttgggc ttcggaatcg ttttccggga cgccggctgg atgatcctcc    4380
agcgcgggga tctcatgctg gagttcttcg cccaccccaa cttgtttatt gcagcttata    4440
atggttacaa ataaagcaat agcatcacaa atttcacaaa taaagcattt ttttcactgc    4500
attctagttg tggtttgtcc aaactcatca atgtatctta tcatgtctgt ataccgtcga    4560
cctctagcta gagcttggcg taatcatggt catagctgtt tcctgtgtga aattgttatc    4620
cgctcacaat tccacacaac atacgagccg gaagcataaa gtgtaaagcc tggggtgcct    4680
aatgagtgag ctaactcaca ttaattgcgt tgcgctcact gcccgctttc cagtcgggaa    4740
acctgtcgtg ccagctgcat taatgaatcg gccaacgcgc ggggagaggc ggtttgcgta    4800
ttgggcgctc ttccgcttcc tcgctcactg actcgctgcg ctcggtcgtt cggctgcggc    4860
gagcggtatc agctcactca aaggcggtaa tacggttatc cacagaatca ggggataacg    4920
caggaaagaa catgtgagca aaaggccagc aaaaggccag gaaccgtaaa aaggccgcgt    4980
```

TABLE 17-continued

| pTTAAx5-EF1α-Luc (SEQ ID NO: 17) | |
|---|---|
| tgctggcgtt tttccatagg ctccgccccc ctgacgagca tcacaaaaat cgacgctcaa | 5040 |
| gtcagaggtg gcgaaacccg acaggactat aaagatacca ggcgtttccc cctggaagct | 5100 |
| ccctcgtgcg ctctcctgtt ccgaccctgc cgcttaccgg atacctgtcc gcctttctcc | 5160 |
| cttcgggaag cgtggcgctt tctcatagct cacgctgtag gtatctcagt tcggtgtagg | 5220 |
| tcgttcgctc caagctgggc tgtgtgcacg aaccccccgt tcagcccgac cgctgcgcct | 5280 |
| tatccggtaa ctatcgtctt gagtccaacc cggtaagaca cgacttatcg ccactggcag | 5340 |
| cagccactgg taacaggatt agcagagcga ggtatgtagg cggtgctaca gagttcttga | 5400 |
| agtggtggcc taactacggc tacactagaa gaacagtatt tggtatctgc gctctgctga | 5460 |
| agccagttac cttcggaaaa agagttggta gctcttgatc cggcaaacaa accaccgctg | 5520 |
| gtagcggtgg tttttttgtt tgcaagcagc agattacgcg cagaaaaaaa ggatctcaag | 5580 |
| aagatccttt gatcttttct acggggtctg acgctcagtg gaacgaaaac tcacgttaag | 5640 |
| ggattttggt catgagatta tcaaaaagga tcttcaccta gatcctttta aattaaaaat | 5700 |
| gaagttttaa atcaatctaa agtatatatg agtaaacttg gtctgacagt t | 5751 |

Example 3

Production of piggyBac mRNA

The piggyBac mRNA was synthesized using pGEM-GL-PB4 (available from BEX Co., Ltd.) as a template. CUGA (registered trademark) 7 in vitro transcription kit (NIPPON GENE Co., Ltd.) was used for synthesis. A Cap structure and a poly(A) structure were added to a untranslated region (UTR) and a 3'-UTR of RNA (Table 18, SEQ ID NO: 18) obtained by purifying this, respectively, so that it became an mRNA.

TABLE 18

| piggyBac mRNA (SEQ ID NO: 18) | |
|---|---|
| atgggtagtt ctttagacga tcagcatatc ctctctgctc ttctgcaaag cgatgacgac | 60 |
| cttgttggtg aggattctga cagtgaaata tcagatcacg taagtgaaga tgacgtccac | 120 |
| agcgatacag aagaagcgtt tatagatgag gtacatgaag tgcagccaac gtcaagcggt | 180 |
| agtgaaatat tagacgaaca aaatgttatt gaacaaccag gttcttcatt ggcttctaac | 240 |
| agaatcttga ccttgccaca gaggactatt agaggtaaga ataaacattg ttggtcaact | 300 |
| tcaaagtcca cgaggcgtag ccgagtctct gcactgaaca ttgtcagatc tcaaagaggt | 360 |
| ccgacgcgta tgtaccgcaa tatatatgac ccacttttat gcttcaaact attttttact | 420 |
| gatgagataa tttcggaaat tgtaaaatgg acaaatgctg agatatcatt gaaacgtcgc | 480 |
| gaatctatga caggtgctac atttcgtgac acgaatgaag atgaaatcta tgctttcttt | 540 |
| ggtattctgg taatgacagc agtgagaaaa gataaccaca tgtccacaga tgacctcttt | 600 |
| gatcgatctt tgtcaatggt gtacgtctct gtaatgagtc gtgatcgttt tgatttttc | 660 |
| atacgatgtc ttagaatgga tgacaaaagt atacggccca cacttcgaga aaacgatgta | 720 |
| tttactcctg ttagaaaaat atgggatctc tttatccatc agtgcataca aaattacact | 780 |
| ccaggggctc atttgaccat agatgaacag ttactcggtt ttagaggacg gtgtccgttt | 840 |
| aggatgtata tcccaaacaa gccaagtaag tatggaataa aaatcctcat gatgtgtgac | 900 |
| agtggtacga agtatatgat aaatggaatg ccttatttgg gaagaggaac acagaccaac | 960 |
| ggagtaccac tcggtgaata ctacgtgaag gagttatcaa agcctgtgca cggtagttgt | 1020 |
| cgtaatatta cgtgtgacaa ttggttcacc tcaatccctt tggcaaaaaa cttactacaa | 1080 |

TABLE 18-continued

| piggyBac mRNA (SEQ ID NO: 18) | |
|---|---|
| gaaccgtata agttaaccat tgtgggaacc gtgcgatcaa acaaacgcga gataccggaa | 1140 |
| gtactgaaaa acagtcgctc caggccagtg ggaacatcga tgttttgttt tgacggaccc | 1200 |
| cttactctcg tctcatataa accgaagcca gctaagatgg tatacttatt atcatcttgt | 1260 |
| gatgaggatg cttctatcaa cgaaagtacc ggtaaaccgc aaatggttat gtattataat | 1320 |
| caaactaaag gcggagtgga cacgctagac caaatgtgtt ctgtgatgac ctgcagtagc | 1380 |
| aagacgaata ggtggcctat ggcattattg tacggaatga taaacattgc ctgcataaat | 1440 |
| tcttttatta tatacagcca taatgtcagt agcaagggag aaaaggttca aagtcgcaaa | 1500 |
| aaatttatga gaaaccttta catgagcctg acgtcatcgt ttatgcgtaa gcgtttagaa | 1560 |
| gctcctactt tgaagagata tttgcgcgat aatatctcta atattttgcc aaatgaagtg | 1620 |
| cctggtacat cagatgacag tactgaagag ccagtaatga aaaaacgtac ttactgtact | 1680 |
| tactgcccct ctaaaataag gcgaaaggca aatgcatcgt gcaaaaaatg caaaaaagtt | 1740 |
| atttgtcgag agcataatat tgatatgtgc caaagttgtt tctga | 1785 |

The addition of the Cap structure and the poly(A) structure was performed with mScript™ mRNA Production System (available from CellScript, LLC.). The operations of the above experiments followed the protocol of each kit.

Example 4

Production of HyperpiggyBac mRNA

HyperpigyBac mRNA was synthesized using pGEM-GLTS-HyPB (available from BEX Co., Ltd.) as a template. CUGA (registered trademark) 7 in vitro transcription kit (NIPPON GENE Co., Ltd.) was used for synthesis. A Cap structure and a poly(A) structure were added to a 5' untranslated region (UTR) and a 3'-UTR of RNA (Table 19, SEQ ID NO: 19) obtained by purifying this, respectively, so that it became an mRNA.

TABLE 19

| Hyper piggyBac mRNA (SEQ ID NO: 19) | |
|---|---|
| augggcggca gaaagaagag aagacagaga agaacacccc ccgccggcac cagcgugagc | 60 |
| cugaagaaga agagaaaggu gcccccgcc uccucccucg augacgagca cauucugucc | 120 |
| gcucugcugc aguccgacga ugagcugguc ggagaagaca gcgauagcga ggugagcgac | 180 |
| cacgucuccg aggacgacgu ccaaagcgac acagaggagg ccuucaucga cgaggugcac | 240 |
| gaggugcagc cuaccagcag cggcuccgag auccuggacg agcagaacgu gaucgagcac | 300 |
| cccggcagcu cccuggccag caacaggauc cugacccugc cccagaggac caucaggggc | 360 |
| aagaacaagc acugcugguc caccuccaag cccaccaggc ggagcagggu guccgcccuc | 420 |
| aacaucguga gaagccagag gggccccacc aggaugagca ggaacaucua cgacccccug | 480 |
| cugugcuuca agcuguucuu caccgacgag aucaucagcg agaucgugaa guggaccaac | 540 |
| gccgagauca gccugaagag gcgggagagc augaccuccg ccaccuucag ggacaccaac | 600 |
| gaggacgaga ucuacgccuu cuucggcauc cuggugauga ccgccgugag gaaggacaac | 660 |
| cacaucagca ccgacgaccu guucgacaga ucccugagca ugguguacgu gagcgugauc | 720 |
| agcagcgaca gauucgacuu ccugaucaga ugccugagga uggacgacaa gagcaucagg | 780 |

TABLE 19-continued

| Hyper piggyBac mRNA (SEQ ID NO: 19) | |
|---|---|
| cccacccugc gggagaacga cguguucacc cccgugagaa agaucuggga ccuguucauc | 840 |
| caccagugca uccagaacua caccccuggc gcccaccuga ccaucgacga gcagcugcug | 900 |
| ggcuucaggg gcaggugccc cuucaggguc uauaucscca acaagcccag caaguacggc | 960 |
| aucaagaucc ugaugaugug cgacagcggc accaaguaca ugaucaacgg caugcccuac | 1020 |
| cugggcaggg gcacccagac caacggcgug ccccugggcg aguacuacgu gaaggagcuc | 1080 |
| uccaagcccg uccacggcag cugcagaaac aucaccugcg acaacugguu caccagcauc | 1140 |
| ccccuggcca agaaccugcu gcaggagccc uacaagcuga ccaucguggg caccgugaga | 1200 |
| agcaacaaga gagagauccc cgagguccug aagaacagca gguccaggcc cgugggcacc | 1260 |
| agcauguucu gcuucgacgg cccccugacc cuggugucuu acaagcccaa gcccgccaac | 1320 |
| augguguacc ugcuguccag cugcgacgag gacgccagca ucaacgagag caccggcaag | 1380 |
| ccccagaugg ugauguacua caaccagacc aagggcggcg uggacacccu ggaccagaug | 1440 |
| ugcagcguga ugaccugcag cagaaagacc aacagguggc ccauggcccu gcuguacggc | 1500 |
| augaucaaca ucgccugcau caacagcuuc aucaucuaca gccacaacgu gagcagcaag | 1560 |
| ggcgagaagg ugcagagccg gaaaaaguuc augcggaacc uguacauggg ccugaccucc | 1620 |
| agcuucauga ggaagaggcu ggaggccccc acccugaaga gauaccugag ggacaacauc | 1680 |
| agcaacaucc ugcccaaaga ggugcccggc accaccgacg acagcaccga ggagcccguc | 1740 |
| augaagaaga ggaccuacug caccuacugu cccaccaaga ucagaagaaa ggccagcgcc | 1800 |
| agcugcaaga aguguaagaa ggucaucugc cgggagcaca acaucgacau gugccagagc | 1860 |
| uguuucuga | 1869 |

The addition of the Cap structure and the poly(A) structure was performed with mScript™ mRNA Production System (available from CellScript, LLC.). The operations of the above experiments followed the protocol of each kit.

Example 5

Measurement of piggyBac Activity by pCMV-LuEuC and pTTAAx5-EF1α-Luc

Human T-cell leukemia cells (Jurkat, manufactured by ATCC (registered trademark)) cultured in a TexMACS medium (manufactured by Miltenyi Biotec) were collected by centrifugation, and then seeded on a 96-well plate at $5.0\times10^5$ cells/well. A vector for measuring transposase cutting activity (pCMV-LuEuC) produced in Example 1, a vector for measuring transposase incorporating activity (pTTAAx5-EF1α-Luc) produced in Example 2, and piggyBac mRNA prepared in Example 3 were encapsulated in lipid nanoparticles containing a cationic lipid, and the lipid nanoparticles were added to the wells so that the amounts of the vectors and mRNA to be added were as shown in Table 20. Thereafter, the culture plate was housed in an incubator, and the cells were cultured at 37° C. in a 5% $CO_2$ atmosphere.

TABLE 20

| | pCMV-LuEuC (μg) | pTTAA × 5-EF1α-Luc (μg) | piggyBac mRNA (μg) |
|---|---|---|---|
| piggyBac mRNA co-introduced | 1 | 1 | 1 |
| piggyBac mRNA no introduction | 1 | 1 | 0 |

After 48 hours from the addition of the lipid nanoparticles, the culture plate was taken out of the incubator, and 50 μL of a culture solution was collected in a 96 well plate. Using ONE-Glo™ Luciferase Assay System (available from Promega Corporation) and Nano-Glo (registered trademark) Luciferase Assay System (available from Promega Corporation), the luminescence intensities of firefly luciferase expressed from a firefly luciferase gene and OG luciferase expressed from an OG luciferase gene were measured with a luminometer (Infinite (registered trademark) F200PRO, available from Tecan Corporation). The measurement was performed according to the manuals attached to the kit and the luminometer.

Figure 13:
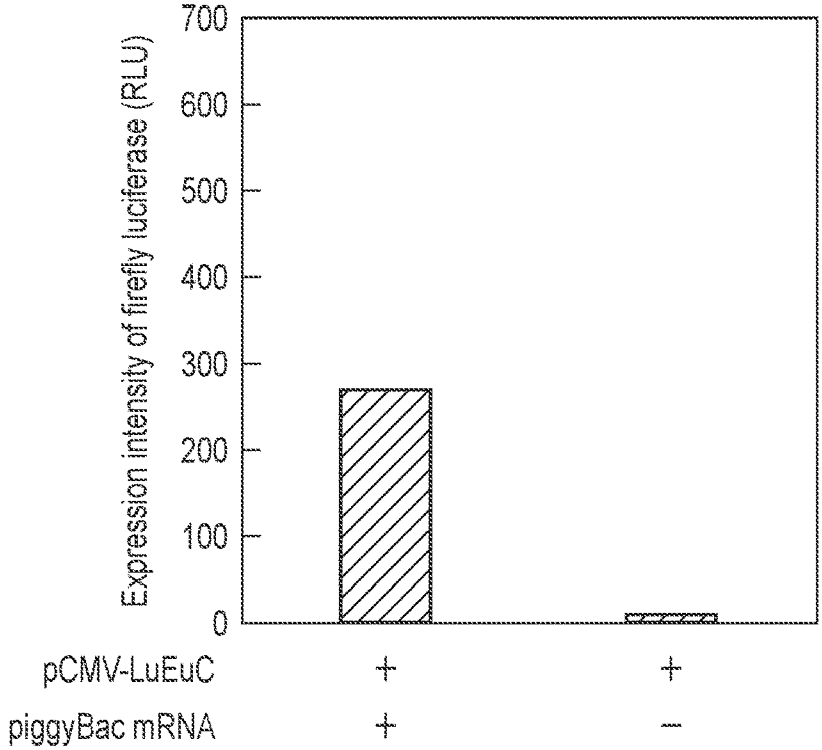
FIG. 13 is a graph showing experimental results of Example 5.

FIG. 13 shows the results of luminescence measurement of firefly luciferase. In Jurkat in which piggyBac mRNA was not introduced, an intensity of 10 RLU was obtained, whereas in Jurkat in which piggyBac mRNA and pCMV-LuEuC were co-introduced, a high luminescence intensity of 270 RLU, which is 27 times, was measured.

Figure 14:
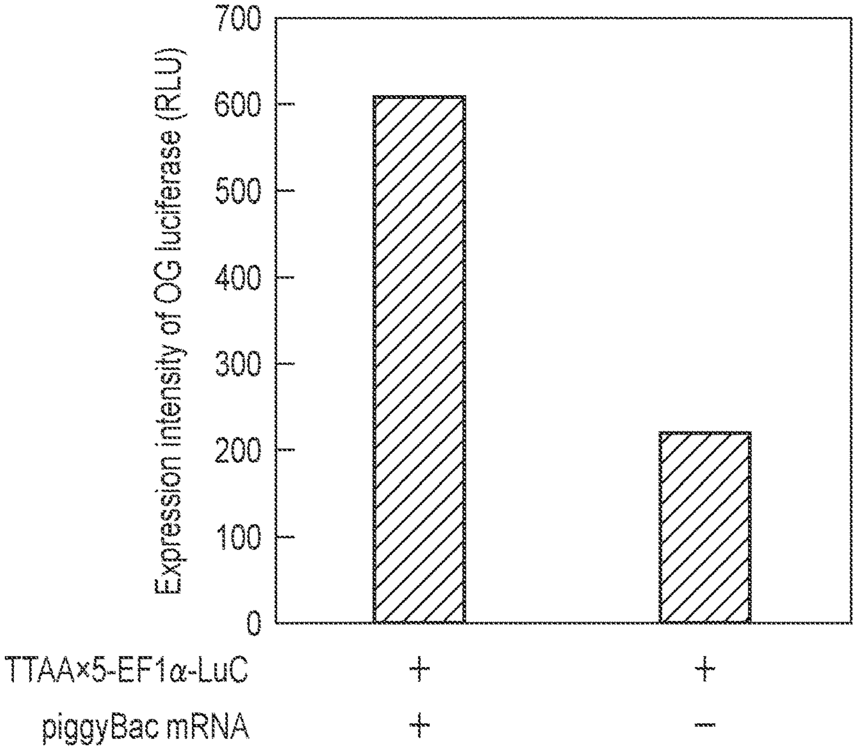
FIG. 14 is a graph showing experimental results of Example 5.

FIG. 14 shows the results of luminescence measurement of OG luciferase. In Jurkat in which piggyBac mRNA was not introduced, an intensity of 220 RLU was obtained, whereas in Jurkat in which piggyBac mRNA and pTTAAx5-EF1α-Luc were co-introduced, a high luminescence intensity of 608 RLU, which is 2.8 times, was measured.

The results of FIG. 13 show that piggyBac expressed from piggyBac mRNA cut out a region interposed between 5'-IR and 3'-IR of pCMV-LuEuC, and a firefly luciferase gene was formed to express firefly luciferase. In addition, the results of FIG. 14 show that the region cut out of pCMV-LuEuC by piggyBac was incorporated into the sequence in which TTAA in the upstream region of the promoter sequence of pTTAAx5EF1α-Luc was repeated 5 times, and the enhancer activated the EF1α promoter to increase the expression intensity of OG luciferase. Therefore, it was revealed that pCMV-LuEuC and pTTAAx5-EF1α-Luc effectively function as vectors for measuring the cutting activity and the incorporating activity of the transposase piggyBac, respectively.

Example 6

Measurement of piggyBac Activity and HyperpiggyBac Activity by pCMV-LuEuC and pTTAAx5-EF1α-Luc Human T-cell leukemia cells (Jurkat, manufactured by ATCC (registered trademark)) cultured in a TexMACS medium (manufactured by Miltenyi Biotec) were collected by centrifugation, and then seeded on a 96-well plate at $2.0\times10^5$ cells/well. A vector for measuring transposase cutting activity (pCMV-LuEuC) produced in Example 1, a vector for measuring transposase incorporating activity (pTTAAx5-EF1α-Luc) produced in Example 2, piggyBac mRNA prepared in Example 3, and HyperpiggyBac mRNA produced in Example 4 were encapsulated in lipid nanoparticles containing a cationic lipid, and the lipid nanoparticles were added to the wells so that the amounts of the vectors and mRNA to be added were as shown in Table 21.

Thereafter, the culture plate was housed in an incubator, and the cells were cultured at 37° C. in a 5% $Co_2$ atmosphere.

TABLE 21

| | pCMV-LuEuC (μg) | pTTAA × 5-EF1α-Luc (μg) | piggyBac mRNA (μg) | Hyper piggyBac mRNA (μg) |
|---|---|---|---|---|
| piggyBac mRNA no introduction | 0.4 | 0.4 | 0 | 0 |
| piggyBac mRNA co-introduced | 0.4 | 0.4 | 0.4 | 0 |
| Hyper piggyBac mRNA co-introduced | 0.4 | 0.4 | 0 | 0.4 |

After 48 hours from the addition of the lipid nanoparticles, the culture plate was taken out of the incubator, and 50 μL of a culture solution was collected in a 96 well plate. Using ONE-Glo™ Luciferase Assay System (available from Promega Corporation) and Nano-Glo (registered trademark) Luciferase Assay System (available from Promega Corporation), the luminescence intensities of firefly luciferase expressed from a firefly luciferase gene and OG luciferase expressed from an OG luciferase gene were measured with a luminometer (Infinite (registered trademark) F200PRO, available from Tecan Corporation). The measurement was performed according to the manuals attached to the kit and the luminometer.

Figure 15:
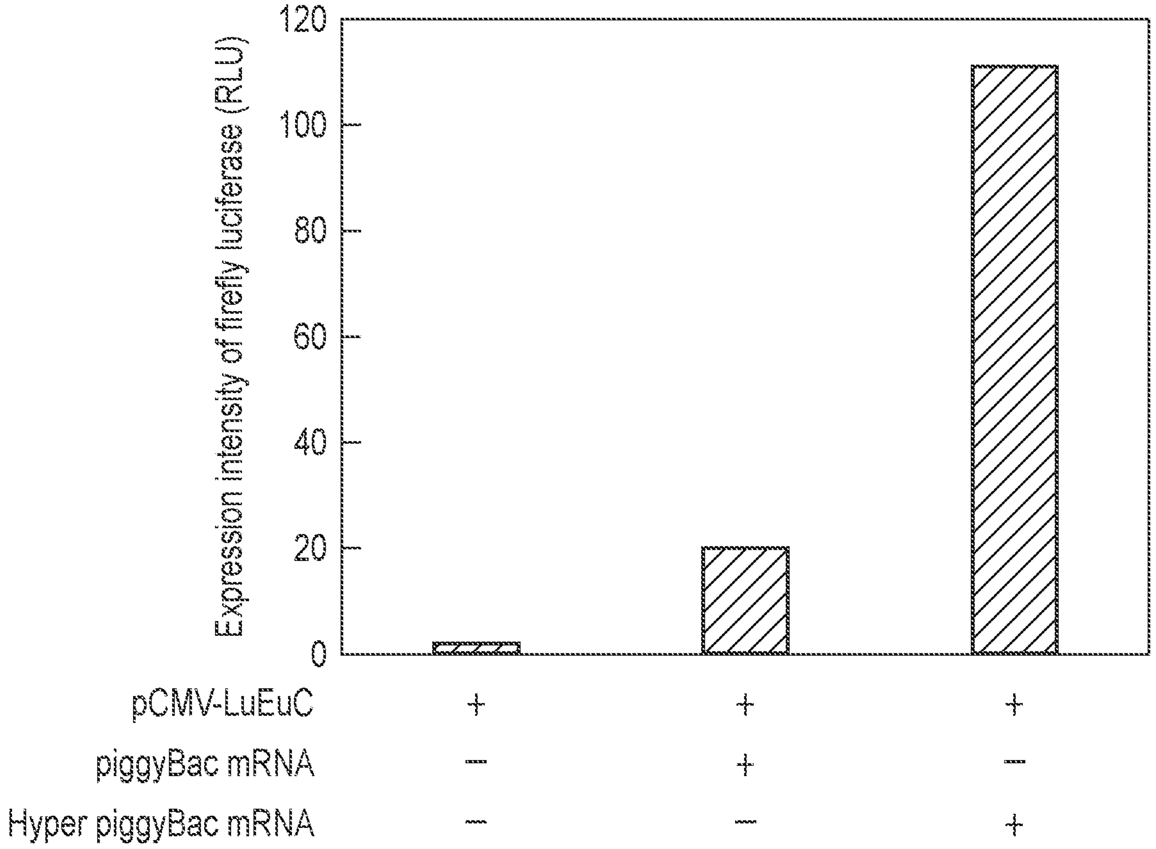
FIG. 15 is a graph showing experimental results of Example 6.

FIG. 15 shows the results of luminescence measurement of firefly luciferase. In Jurkat in which piggyBac mRNA and pCMV-LuEuC were co-introduced, an intensity of 20 RLU was obtained, whereas in Jurkat in which HyperpiggyBac and pCMV-LuEuC were co-introduced, a high luminescence intensity of 111 RLU, which is 5 times, was measured.

Figure 16:
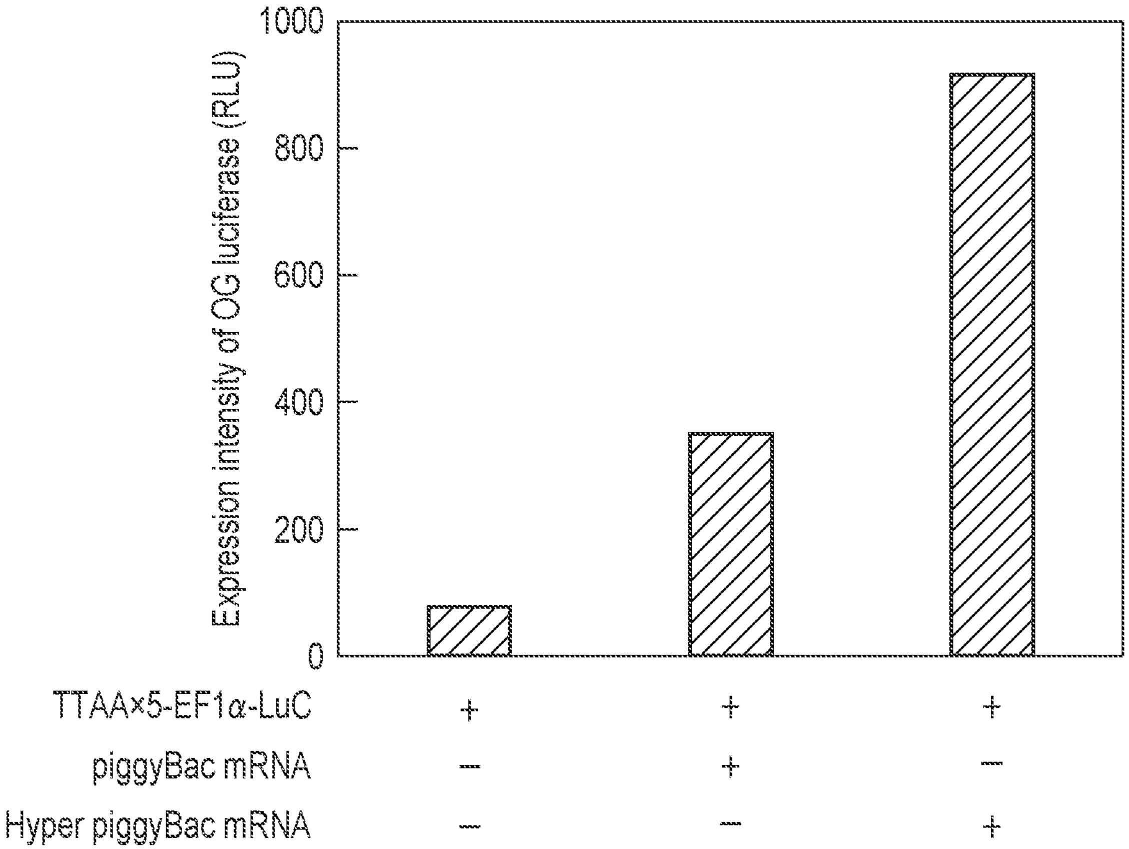
FIG. 16 is a graph showing experimental results of Example 6.

FIG. 16 shows the results of luminescence measurement of OG luciferase. In Jurkat in which piggyBac mRNA and pTTAAx5-EF1α-Luc were co-introduced, an intensity of 349 RLU was obtained, whereas in Jurkat in which HyperpiggyBac and pTTAAx5-EF1α-Luc were co-introduced, a high luminescence intensity of 914 RLU, which is 3 times, was measured.

The results of FIG. 15 showed that more firefly luciferase was expressed in Jurkat in which HyperpiggyBac expressed from HyperpiggyBac mRNA was co-introduced, as compared with the case where piggyBac expressed from piggyBac mRNA was co-introduced. In addition, the results of FIG. 16 showed that the increase in the expression level of OG luciferase was greater in Jurkat in which HyperpiggyBac expressed from HyperpiggyBac mRNA was co-introduced, as compared with the case where piggyBac expressed from piggyBac mRNA was co-introduced. Therefore, it was revealed that pCMV-LuEuC and pTTAAx5-EF1α-Luc effectively function as vectors for measuring the cutting activity and the incorporating activity of the transposase piggyBac, respectively.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A vector set comprising a first vector comprising a transposase target sequence, a first promoter sequence ligated downstream of the transposase target sequence, and a first reporter gene ligated downstream of the first promoter sequence; and a second vector comprising a second vector comprising, in order from its 5' end to its 3' end, a second promoter sequence, a 5'-side fragment of a second reporter gene, 5'-side of a transposase recognition sequence, a first enhancer sequence, 3'-side of the transposase recognition sequence, and a 3'-side fragment of the second reporter gene; and wherein the 5'-side fragment of the second reporter gene and the 3'-side fragment of the second reporter gene are obtained by dividing the second reporter gene into the 5'-side fragment and the 3'-side fragment.

2. The vector set according to claim 1, wherein the second reporter gene is inactivated because it is divided into the 5'-side fragment and the 3'-side fragment.

3. The vector set according to claim 1, wherein the first reporter gene and the second reporter gene are different from each other.

4. The vector set according to claim 1, wherein the second vector further comprises a second enhancer sequence ligated upstream of the second promoter sequence.

5. The vector set according to claim 1, wherein the 5'-side fragment of the second reporter gene comprises a sequence of SEQ ID NO: 12, and the 3'-side fragment of the second reporter gene comprises a sequence of SEQ ID NO: 13.

6. The vector set according to claim 1, wherein the transposase target sequence comprises a sequence of SEQ ID NO: 1.

7. The vector set according to claim 1, wherein the first enhancer sequence comprises a sequence of SEQ ID NO: 11.

8. The vector set according to claim 1, wherein the first promoter sequence comprises a sequence of SEQ ID NO: 3.

9. The vector set according to claim 1, wherein the first reporter gene comprises a sequence of SEQ ID NO: 5.

10. The vector set according to claim 1, wherein the 5'-side of the transposase recognition sequence and the 3'-side of the transposase recognition sequence comprise a sequence of SEQ ID NO: 8 and a sequence of SEQ ID NO: 9, respectively.

11. The vector set of claim 1, wherein the vector set is suitable for measuring an activity of a transposase;

the second vector further comprises a transposon sequence to be transposed by the transposase;

the 5'-side of the transposase recognition sequence is ligated to a 5'-side end of the transposon sequence; and the 3'-side of the transposase recognition sequence is ligated to a 3'-side end of the transposon sequence;

the transposon sequence contains the first enhancer sequence;

the 5'-side of the transposase recognition sequence is a repeat sequence for being bound to the transposase; and the 3'-side transposase of the recognition sequence is a repeat sequence for being bound to the transposase, is identical to the 5'-side of the transposase recognition sequence but is in a mutually opposite direction in the second vector relative to the 5'-side of the transposase recognition sequence.

12. A vector set comprising:

a first vector including a sequence of a gene expression unit that comprises, in order from its 5' end to its 3' end, 5' side of a first enhancer sequence, a transposase target sequence, 3' side of the first enhancer sequence, a first promoter sequence or in order from its 5' end to its 3' end, the first enhancer sequence, 5' side of the first promoter sequence, the transposase target sequence, 3' side of the first promoter sequence, and the first reporter gene; and a second vector, in order from its 5' end to its 3' end, including a 5'-side of a transposase recognition sequence, a sequence involved in expression of the first reporter gene, a 3'-side of the transposase recognition sequence, and a second promoter sequence.

13. The vector set of claim 12, wherein the second vector further comprises a transposon sequence to be transposed by the transposase;

the 5'-side of the transposase recognition sequence is ligated to a 5'-side end of the transposon sequence; and the 3'-side of the transposase recognition sequence is ligated to a 3'-side end of the transposon sequence;

the transposon sequence contains the sequence involved in expression of the first reporter gene;

the 5'-side of the transposase recognition sequence is a repeat sequence for being bound to the transposase; and the 3'-side of the transposase recognition sequence is a repeat sequence for being bound to the transposase, is identical to a 5'-side of the transposase recognition sequence but is in a mutually opposite direction in the second vector relative to the 5'-side of the transposase recognition sequence.

14. The vector set according to claim 12, wherein the second vector further comprises a second reporter gene such that the second vector comprises, in order from its 5' end to its 3' end, the second promoter sequence, 5' side fragment of the second reporter gene, the 5'-side of the transposase recognition sequence, the sequence involved in expression of the first reporter gene, the 3'-side of the transposase recognition sequence, and 3' side fragment of the second reporter gene.

15. The vector set according to claim 12, wherein the second vector further comprises a second enhancer sequence ligated upstream of the second promoter sequence.

16. A kit for measuring an activity of a transposase, the kit comprising the vector set of claim 1 and a reagent for detecting a first reporter protein expressed from the first reporter gene.

17. The kit according to claim 16, wherein the vector set is encapsulated in a lipid particle.

* * * * *